(12) United States Patent  
Levendowski et al.

(10) Patent No.: US 10,953,192 B2  
(45) Date of Patent: Mar. 23, 2021

(54) SYSTEMS AND METHODS FOR DETECTING AND MANAGING PHYSIOLOGICAL PATTERNS

(71) Applicant: Advanced Brain Monitoring, Inc., Carlsbad, CA (US)

(72) Inventors: Daniel J. Levendowski, Carlsbad, CA (US); Bratislav Veljkovic, Belgrade (RS); Amy Matthews, Encinitas, CA (US); Vladislav Velimirovic, Belgrade (RS); Elise Ramos Angel, Huntington Beach, CA (US); Christine Berka, Carlsbad, CA (US); Gene Davis, Oceanside, CA (US); Aleksandar Zoranovic, Belgrade (RS); Milenko Cvetinovic, Belgrade (RS); Philip R. Westbrook, Oceanside, CA (US)

(73) Assignee: ADVANCED BRAIN MONITORING, INC., Carlsbad, CA (US)

( * ) Notice: Subject to any disclaimer, the term of this patent is extended or adjusted under 35 U.S.C. 154(b) by 277 days.

(21) Appl. No.: 15/984,189

(22) Filed: May 18, 2018

(65) Prior Publication Data  
US 2018/0333558 A1    Nov. 22, 2018

Related U.S. Application Data

(60) Provisional application No. 62/508,221, filed on May 18, 2017, provisional application No. 62/620,236, filed on Jan. 22, 2018.

(51) Int. Cl.  
*A61M 21/02* (2006.01)  
*A61B 5/00* (2006.01)  
(Continued)

(52) U.S. Cl.  
CPC .............. *A61M 21/02* (2013.01); *A61B 5/11* (2013.01); *A61B 5/369* (2021.01); *A61B 5/389* (2021.01);  
(Continued)

(58) Field of Classification Search  
CPC ................ A61M 21/00; A61M 21/02; A61M 2021/0005; A61M 2021/0022;  
(Continued)

(56) References Cited

U.S. PATENT DOCUMENTS

| | | |
|---|---|---|
| 5,081,447 A | 1/1992 | Echols |
| 5,132,426 A | 7/1992 | Seltzer et al. |

(Continued)

FOREIGN PATENT DOCUMENTS

| | | |
|---|---|---|
| EP | 1741387 A1 | 1/2007 |
| JP | 2011-104338 A | 6/2011 |
| WO | 2013050912 A1 | 4/2013 |

OTHER PUBLICATIONS

Johansson. Neural network for photoplethysmographic respiratory rate monitoring. Med Biol Eng Comput. May 2003;41(3)242-8.

(Continued)

*Primary Examiner* — Carrie R Dorna  
(74) *Attorney, Agent, or Firm* — Procopio, Cory, Hargreaves & Savitch LLP

(57) ABSTRACT

Systems and methods for managing sleep quality of a patient, comprising: collecting physiological signal data of the patient using a data acquisition unit electrically coupled to at least one sensor affixed to the patient that generates the physiologic signal data; using one or more hardware processors executing instructions stored in a storage device: filtering the physiological signal data into a plurality of frequency bands corresponding to a plurality of power spectra waveforms; and characterizing an etiology of sleep  
(Continued)

quality of the patient based on a comparison of at least a first power spectra waveform of the plurality of power spectra waveforms against at least a second power spectra waveform of the plurality of power spectra waveforms, wherein the sleep quality of the patient is managed based on the characterized etiology of sleep.

20 Claims, 31 Drawing Sheets

(51) Int. Cl.
    *A61B 5/11*     (2006.01)
    *A61B 5/369*     (2021.01)
    *A61B 5/389*     (2021.01)
    *A61B 5/398*     (2021.01)
    *A61M 21/00*     (2006.01)

(52) U.S. Cl.
    CPC ............ *A61B 5/398* (2021.01); *A61B 5/4094* (2013.01); *A61B 5/4815* (2013.01); *A61B 5/4818* (2013.01); *A61M 2021/0022* (2013.01); *A61M 2021/0027* (2013.01); *A61M 2021/0044* (2013.01); *A61M 2021/0066* (2013.01); *A61M 2021/0077* (2013.01); *A61M 2205/3303* (2013.01); *A61M 2205/3375* (2013.01); *A61M 2205/3561* (2013.01); *A61M 2205/3592* (2013.01); *A61M 2205/505* (2013.01); *A61M 2230/10* (2013.01); *A61M 2230/14* (2013.01); *A61M 2230/40* (2013.01); *A61M 2230/60* (2013.01); *A61M 2230/63* (2013.01)

(58) Field of Classification Search
    CPC .. A61M 2021/0027; A61M 2021/0044; A61M 2021/0066; A61M 2021/0077; A61B 5/0146; A61B 5/048
    See application file for complete search history.

(56) References Cited

U.S. PATENT DOCUMENTS

| | | | |
|---|---|---|---|
| 5,381,801 A | 1/1995 | McShane et al. | |
| 5,447,161 A | 9/1995 | Blazek et al. | |
| 5,474,082 A | 12/1995 | Junker | |
| 5,479,934 A | 1/1996 | Imran | |
| 5,507,716 A | 4/1996 | LaBerge et al. | |
| 5,692,517 A | 12/1997 | Junker | |
| 6,272,378 B1 | 8/2001 | Baumgart-Schmitt | |
| 6,416,471 B1 | 7/2002 | Kumar et al. | |
| 6,454,708 B1 | 9/2002 | Ferguson et al. | |
| 6,600,949 B1 | 7/2003 | Turcott | |
| 6,641,571 B2 | 11/2003 | Redmond et al. | |
| 6,654,626 B2 | 11/2003 | Devlin et al. | |
| 6,811,538 B2 | 11/2004 | Westbrook et al. | |
| 6,970,792 B1 | 11/2005 | Diab | |
| 7,041,049 B1 | 5/2006 | Raniere | |
| 7,081,095 B2 | 7/2006 | Lynn et al. | |
| 7,117,028 B2 | 10/2006 | Bardy | |
| 7,118,534 B2 | 10/2006 | Ward et al. | |
| 7,311,666 B2 | 12/2007 | Stupp et al. | |
| 7,691,067 B2 | 4/2010 | Westbrook et al. | |
| 7,717,848 B2 | 5/2010 | Heruth et al. | |
| 8,069,852 B2 | 12/2011 | Burton et al. | |
| 8,355,769 B2 | 1/2013 | Levendowski et al. | |
| 8,639,313 B2 | 1/2014 | Westbrook et al. | |
| 8,649,855 B2 | 2/2014 | Bier et al. | |
| 8,838,226 B2 | 9/2014 | Bibian et al. | |
| 2002/0165462 A1 | 11/2002 | Westbrook et al. | |
| 2002/0169384 A1 | 11/2002 | Kowallik et al. | |
| 2002/0184050 A1 | 12/2002 | Papageorge | |
| 2002/0188205 A1 | 12/2002 | Mills | |
| 2004/0002742 A1 | 1/2004 | Florio | |
| 2004/0015337 A1 | 1/2004 | Thomas et al. | |
| 2004/0163648 A1 | 8/2004 | Burton | |
| 2005/0085738 A1 | 4/2005 | Stahmann et al. | |
| 2005/0131288 A1 | 6/2005 | Turner et al. | |
| 2005/0143617 A1 | 6/2005 | Auphan | |
| 2005/0234313 A1 | 10/2005 | Rowlandson et al. | |
| 2005/0283039 A1 | 12/2005 | Cornel | |
| 2006/0100538 A1 | 5/2006 | Genger et al. | |
| 2006/0106275 A1 | 5/2006 | Raniere | |
| 2006/0235315 A1 | 10/2006 | Akselrod et al. | |
| 2006/0241708 A1 | 10/2006 | Boute | |
| 2007/0021979 A1 | 1/2007 | Cosentino et al. | |
| 2007/0208269 A1 | 9/2007 | Mumford et al. | |
| 2007/0214013 A1 | 9/2007 | Silverman | |
| 2007/0249952 A1 | 10/2007 | Rubin et al. | |
| 2007/0282177 A1 | 12/2007 | Pilz | |
| 2008/0234785 A1 | 9/2008 | Nakayama et al. | |
| 2008/0319277 A1 | 12/2008 | Bradley | |
| 2009/0030489 A1 | 1/2009 | Asvadi et al. | |
| 2009/0198145 A1 | 8/2009 | Chow | |
| 2009/0207028 A1 | 8/2009 | Kubey et al. | |
| 2009/0240119 A1 | 9/2009 | Schwaibold et al. | |
| 2010/0131028 A1 | 5/2010 | Hsu et al. | |
| 2010/0204550 A1 | 8/2010 | Heneghan et al. | |
| 2011/0098593 A1 | 4/2011 | Low et al. | |
| 2012/0161783 A1 | 6/2012 | Berka et al. | |
| 2012/0296156 A1* | 11/2012 | Auphan ............... | A47C 21/003 |
| | | | 600/28 |
| 2013/0131464 A1 | 5/2013 | Westbrook et al. | |
| 2014/0222101 A1 | 8/2014 | Miesel et al. | |
| 2014/0316230 A1 | 10/2014 | Denison et al. | |
| 2014/0323900 A1 | 10/2014 | Bibian et al. | |
| 2015/0257674 A1 | 9/2015 | Jordan et al. | |
| 2016/0066703 A1* | 3/2016 | Chen ..................... | A61G 7/015 |
| | | | 5/613 |

OTHER PUBLICATIONS

Kaw et al. Unrecognized Sleep Apnea in the Surgical Patient: Implications for the Perioperative Setting. Chest, 2006. 129(1): p. 198-205.

Keifer et al. Sleep Disruption and Increased Apneas after Pontine Microinjection of Morphine. Anesthesiology, 1992. 77(5): p. 973-82.

Kheterpal et al. Prediction and Outcomes of Impossible Mask Ventilation, Anesthesiology, vol. 110, No. 4, Apr. 2009, pp. 891-897.

Knill et al. Anesthesia with Abdominal Surgery Leads to intense REM Sleep during the First Postoperative Week. Anesthesiology, 1990. 73(1): p. 52-61.

Kushida et al. Technical protocol for the use of esophageal manometry in the diagnosis of sleep-related breathing disorders. Sleep Med 3(2002) 163-173.

Leonard et al. An algorithm for the detection of individual breaths from the pulse oximeter waveform. J Clin Monit Comput. Dec. 2004;18(5-6):309-12.

Li et al. Study of the prevention and control of delirium in ventilated patients by simulating blockage of circadian rhythm with sedative in the intensive care unit. 2016; 28(1):50-6.

Lickteig et al. Risks of OSA and Anesthesia, Sleep Review, Jan./Feb. 2003, 5 pages.

Loadsman et al. Anaesthesia and sleep apnoea. British Journal of Anaesthesia, 2001. 86(2): p. 254-266.

Lofsky. Sleep apnea and narcotic postoperative pain medication: a morbidity and mortality risk. Anesthesia Patient Safety Foundation Newsletter Summer 2002:24-25.

Magder. How to use central venous pressure measurements. Curr Opin Crit Care., Jun. 2005;11(3):264-70.

Mannheimer et al. The influence of large subcutaneous blood vessels on pulse oximetry. J Clin Monitor Comput 18:179-188, 2004.

Marshall et al. Focal and/or lateralized polymorphic delta activity; Association with either 'normal' or 'nonfocal' computed tomographic scans. Arch Neurol 1988; 45(10: 33-35.

(56) References Cited

OTHER PUBLICATIONS

Nakajima et al. Monitoring the heart and respiratory rates by photoplethysmography using a digital filtering technique. Med Eng Phys 1996 1 8(5) 365-372.
Neligan et al. Continuous Positive Airway Pressure via the Boussignac System Immediately after Extubation Improves Lung Function in Morbidly Obese Patients with Obstructive Sleep Apnea Undergoing Laparoscopic Bariactric Surgery, Anesthesiology, vol. 110, No. 4, Apr. 2009, pp. 878-884.
Nilsson et al. Macrocirculation is not the sole determinant of respiratory induced variations in the reflection mode photoplethysmographic signal. Physiol Meas. Nov. 2003; 24(4):925-37.
Nilsson et al. Monitoring of respiratory rate in postoperative care using a new photoplethysmographic technique. J Clin Monit Comput. 2000; 16(4):309-15.
Nilsson et al. Respiration can be monitored by photoplethysmography with high sensitivity and specificity regardless of anaesthesia and ventilatory mode. Acta Anaesthesiol Scand. Sep. 2005; 49(8): 1157-62.
Nilsson et al. Respiratory variations in the reflection mode photoplethysmographic signal. Relationships to peripheral venous pressure. Med Biol Comput. May 2003;41(3):249-54.
Nilsson et al., Age and gender do not influence the ability to detect respiration by photoplethysmography. J Clin Monit Comput. Dec. 2006; 20(6), pp. 431-6. Epub Oct. 11, 2006.
Nozawa et al. A simplified electroencephalogram monitoring system in the emergency room. Pediatr Emerg Care 2017; epub doi. 10.1097/PEC.00000001033.
Oliver et al. Predicting effective continuous positive airway pressure. Chest, 2000. 117(4): p. 1061-4.
Orr et al. Sleep disturbances after open heart surgery. Am J Cardiol, 1977. 39(2): p. 196-201.
Pembrook. High Risk for Sleep Apnear Found in Pain Patients on Opioids, Issue: Jun. 2006, vol. 32:06, 3 pages.
Pilcher et al. High central venous pressure is associated with prolonged mechanical ventilation and increased mortality after lung transplantation. J Thorac Cardiovasc Surg. 2005;129(4):912-8.
Pitson et al. Value of beat-to-beat blood pressure changes, detected by pulse transit time, in the management of obstructive sleep apnea/hypopnea syndrome. Eur Respir J 1998:12:685-692.
Piva et al. Neuroinflammation in sepsis: sepsis associated delirium. Cardiovasc Hematol Disord Drug Targets 2015; 15(1):10-18.
Praline et al. Emergent EEG is helpful in clinical care practice. Clin Neurophysiol 2007; 118(10):2149-55.
Rai et al. Continuous EEG predictors of outcomes in patients with altered sensorium. Seizure 2013; 22(8):656-61.
Ramachandran et al. A Meta-analysis of Clinical Screening Tests for Obstructive Sleep Apnea, Anesthesiology, Vo. 110., No. 4, Apr. 2009, pp. 928-939.
Reeder et al. Late postoperative nocturnal dips in oxygen saturation in patients undergoing major abdominal vascular surgery. Predictive value of pre-operative overnight pulse oximetry. Anaesthesia, 1992. 47(2): p. 110-5.
Reeder et al. Postoperative hypoxaemia after major abdominal vascular surgery. Sr J Anaesth, 1992. 68(1): p. 23-6.
Reeder et al. Postoperative obstructive sleep apnoea. Haemodynamic effects of treatment with nasal CPAP. Anaesthesia, 1991. 46(10): p. 849-53.
Remmers et al. Pathogenesis of upper airway occlusion during sleep. J Appl Physiol.: Respirat. Environ. Exercise Physiol., 1978. 44(6): p. 931-8.
Rock et al. Preoperative assessment pulmonary. Anesthesiology Clinics of North America, 2004.22(1): p. 77-91.
Rosenberg et al. Postoperative episodic oxygen desaturation in the sleep apnoea syndrome. Acta Anaesthesiol Scand, 1991. 35(4): p. 368-9.
Rosenberg et al. Circadian variation in unexpected postoperative death. Br J Surg, 1992. 79(12): p. 1300-2.

Rosenberg et al. Late postoperative nocturnal episodic hypoxaemia and associated sleep pattern. Br J Anaesth, 1994. 72(2): p. 145-50.
Rosenberg-Adamsen et al. Postoperative sleep disturbances: mechanisms and clinical implications. Br J Anaesth, 1996. 76(4): p. 552-9.
Sabers et al. The diagnosis of obstructive sleep apnea as a risk factor for unanticipated admissions in outpatient surgery. Anesth Analg. May 2003;96(5)1328-35.
Sasse et al. Timing of Changes in Oxyhemoglobin Saturation Resulting from Breath Holding. Sleep Medicine, 2006. 7 (S2): p. S46-7.
Semmler et al. Sepsis causes neuroinflammation an concomitant decrease is cerebral metabolism. J Inflammation 2008; 5:38. DOI 10.1186/1742-2094-5-38.
Shah et al. Can disrupted sleep affect mortality in the mechanically ventilated critically ill? Meeting of the American Thoracic Society, May 2016, San Francisco, CA. S/A.
Shepard et al. Effects of changes in central venous pressure on upper airway size in patients with obstructive sleep apnea. Am J Respir Crit Care Med. Jan. 1996;153 (1):250-4.
Stam et al. Dynamics underlying rhythmic and non-rhythmic variants of abnormal waking delta activity. Int J Psychophysiol 1999; 34(1):5-20.
Standards and Practice Committee of the American Sleep Disorders Association. ASDA Standards of Practice, Practice Parameters for the Use of Portable Recording in the Assessment of Obstructive Sleep Apnea . . . Sleep, 1994 17(4), p. 372-377.
Teng. The effect of contacting force on photoplethysmographic signals. Physiol Meas. Oct. 2004;25 (5):1323-35.
Van Dellen et al. Local polymorphic delta activity in cortical lesions causes global decreases in functional connectivity. Neuroimage 2013;83:524-32.
Vanderheyden et al. Sleep alterations following exposure to stress predict fear-associated memory impairments in a rodent model of PTSD. Exp Br Research 2015; 233(8):2335-46.
International Search Report and Written Opinion for corresponding PCT application No. PCT/US2018/033530, dated Dec. 14, 2018, in 15 pages.
Examination Report dated Nov. 14, 2019 for related EP Patent Application No. 10754067.6, in 8 pages.
Verbrugghe et al. Neurally adjusted ventilatory assist: a ventilation tool or a ventilation toy? Respir Care 2011; 56 (3):327-35.
Waldemar et al. Alae nasi activation (nasal flaring) decreases nasal resistance in preterm infants. Pediatrics vol. 72, Issue 3, pp. 338-343, 1983.
Watemberg et al. Clinical and radiological correlates of frontal intermittent rhythmic delta activity. J Clin Neurophysiol 2002; 19(6):535-9.
Watson et al. Atypical sleep in ventilated patients; empirical electroencephalography findings and the path toward revised ICU sleep scoring criteria Crit Care Med 2013; 41(8):1958-67.
Watson et al. Delirium: is sleep important? Rest Pract Res Clin Anaesthesiol 2012; 26(3):355-66.
Watson et al. Presence of electroencephalogram burst suppression in sedated, critically ill patients is associated with increased mortality. Crit Care Med 2008; 36(12):3171-7.
Westbrook et al. Description and Validation of the Apnea Risk Evaluation System: A Novel Method to Diagnose Sleep Apnea-Hypopnea in the Home. Chest, 2005. 128(4): p. 2166-75.
Westbrook et al. Predicting Effective Continuous Positive Airway Pressure (CPAP) based on Laboratory Titration and Auto-titrating CPAP, 8th World Congress on OSA. Sleep Medicine. vol. 7, Suppl. 2. 2006.2 pages.
Westbrook et al. Predicting Treatment Outcomes for Oral Appliance Therapy for Sleep Apnea using Pretreatment In-home Sleep Studies, 8th World Congress on OSA. Sleep Medicine. vol. 7, Suppl. 2. 2006. p. 1-2.
Westbrook et al. Validation of an Apnea Risk Evaluation Questionnaire. In American Thoracic Society International Conference. 2005. San Diego, CA. 2 pages.
Wilson et al. Can Assessment for Obstructive Sleep Apnea Help Predict Postadenotonsillectomy Respiratory Complications, Anesthesiology, vol. 96, No. 2, Feb. 2002, pp. 313-322.

(56) References Cited

OTHER PUBLICATIONS

Wyckoff et al. Validation of a wireless dry electrode system for electroencephalography. J Neuroeng Rehabil 2015; 12:95.
Young et al. Epidemiology of Obstructive Sleep Apnea: A Population Health Perspective. Am J Respir Crit Care Med, 2002. 165(9): p. 1217-39.
Young et al. The electroencephalogram in sepsis-associated encephalopathy. J Clin Neurophysiol 1992; 9:145-52.
Zampieri et al. Sepsis-associated encephalopathy: not just delirium. Clinics 2011; 66(10):1825-1831.
Zhang et al. EEG patterns from acute to chronic stroke phases in focal cerebral ischemic rats: correlations with functional recovery. Physiol Meas 2013; 34(4):423-35.
A Report by the American Society of Anesthesiologists Task Force on Perioperative Management of Patients with Obstructive Sleep Apnea, Practice Guidelines for the Perioperative Management of Patients with Obstructive Sleep Apnea. Anesthesiology, 2006. 104(5): p. 1081-1093.
Accolla et al. Clinical correlates of frontal intermittent rhythmic delta activity (FIRDA). Clin Neurolphysiol 2011; 122 (1): 27-31.
Alemohammad, M. et al. Pressure measurements during cardiac surgery—internal jugular vs. central venous. Middle East J Anestesiol. 2005; 18(2):357-65.
Andresen et al. Burst suppression in processed electroencephalography as a predictor of postcoma delirium in mechanically ventilated ICU patients. Crit Care Med 2014; 42(10):2244-51.
Argod et al. Comparison of Esophageal Pressure with Pulse Transit Time as a measure of respiratory effort for scoring obstructive nonapneic respiratory events. Am J Respir Crit Care Med vol. 162 (2000) 87-93.
Aurell et al. Sleep in the surgical intensive care unit: continuous polygraphic recording of sleep in nine patients receiving postoperative care. Sr Med J (Clin Res Ed), 1985. 290(6474): p. 1029-32.
Benumof. Obesity, sleep apnea, the airway, and anesthesia. Current Opinion in Anaesthesiology, 2004. 17(1): p. 21-30.
Benumof. Obstructive sleep apnea in the adult obese patient: implications for airway management. Anesthesiology Clinics of North America, 2002. 20(4): p. 789-811.
Berry et al. THE AASM manual for scoring of sleep and associated events: rules, terminology and technical specifications, version 2.0, www.aasmnet.org. Darien, IL: American Academy of Sleep Medicine, 2012.
Boesen et al. Sleep and delirium in unsedated patients in the intensive care unit. Acta Anaesthesiol Scand 2016; 60 (1):59-68.
Bosma et al. Patient-ventilator interaction and sleep in mechanically ventilated patients: pressure support versus proportional assist ventilation. Crit Care Med 2007; 35(4):1048-54.
Brown. Intermittent Hypoxia and the Practice of Anesthesia. Anesthesiology. 2009 110(4). p. 922-9.
Cabello et al. Sleep quality in mechanically ventilated patients; comparison of three ventilatory modes. Crit Care Med 2008; 36(6):1749-55.
Cannesson et al. Relation between respiratory variations in pulse oximetry plethysmographic waveform amplitude and arterial pulse pressure in ventilated patients. Crit Care. Oct. 5, 2005;9(5):R562-8. Epub Aug. 23, 2005.
Catley et al., Pronounced, episodic oxygen desaturation in the postoperative period: its association with ventilatory pattern and analgesic regimen. Anesthesiology, 1985. 63(1): p. 20-8.
Chung et al., A Systemic Review of Obstructive Sleep Apnea and Its Implications for Anesthesiologists, Ambulatory Anesthesiology, vol. 107, No. 5, Nov. 2008, pp. 1543-1563.
Cox et al. Measurement of central venous pressure from a peripheral intravenous catheter in the lower extremity. South Med J. Jul. 2005;98(7):698-702.
Cronin et al., Opioid inhibition of rapid eye movement sleep by a specific mu receptor agonist. Br J Anaesth, 1995. 74(2): p. 188-92.
Delisle et al. Sleep quality in mechanically ventilated patients: comparison between NAVA and PSV modes. Ann Intensive Care 2011; 28(1):42.

Den Herder et al. Risks of General Anaesthesia in People with Obstructive Sleep Apnoea, BMJ, vol. 329, Oct. 23, 2004, pp. 955-959 and 1 cover sheet.
Dericioglu et al. Frontal intermittent rhythmic delta activity (FIRDA) in the neurological intensive care. Clin EEG Neurosci 2017; DOI 10.1177/1550059416688108 epub.
Deutscher et al. OSA protocol promotes safer care. Anesthesia Patient Safety Foundation Newsletter 2002-2003: p. 58-60.
Ellis et al. Some aspects of sleep research in surgical stress. J Psychosom Res, 1976. 20(4): p. 303-8.
Farre et al. Noninvasive monitoring of respiratory mechanics during sleep. Eur Respir J. Dec. 2004;24(6):1052-60.
Finkel et al. Obstructive Sleep Apnea: The Silent Pandemic. In ASA Annual Meeting. 2006. Chicago, IL.: 1 page.
Finkel et al. The Silent Perioperative Pandemic. Sleep Review, 2006. 7(4): p. 56-60.
Firosh et al. Emergent EEG is helpful in neurology critical care practice. Clin Neurophysiol 2005; 116(10:2454-9.
Foo et al. Estimation of breathing interval from the photoplethysmographic signals in children. Physiol Meas. Dec. 2005;26(6):1049-58. Epub Oct. 31, 2005.
Foo et al. Use of pulse transit time to distinguish respiratory events from tidal breathing in sleeping children. Chest 2005; 128; 3013-3019.
Freedman et al. Abnormal sleep/wake cycles and the effect of environmental noise on sleep disruption in the Intensive care unit. Am J Respir Crit Care Med 2001; 163(2):451-7.
Fuhrmann et al. Challenges of sleep in the ICU: The significance of sedatives in sleep architecture. Meeting of the American Thoracic Society, May 2016, San Francisco, CA. S/A.
Furbass et al. Monitoring burst suppression in critically ill patients: Multi-center evaluation of a novel method. Clin Neurophysiol 2016; 127(4):2038-46.
Gali et al. Management Plan to Reduce Risks in Perioperative Care of Patients with Presumed Obstructive Sleep Apnea Syndrome, JCSM Journal of Clinical Sleep Medicine, vol. 3, No. 6, 2007, pp. 582-588.
Gali. Identification of Patients at Risk for Postoperative Respiratory Complications Using a Preoperative Obstructive Sleep Apnea Screening Tool and Postanesthesia Care Assessment. Anesthesiology. 2009 110(4). p. 869-77.
Gaspard et al. Similarities of lateralized rhythmic delta activity to periodic lateralized epileptiform discharges in critically ill patients. JAMA Neurol 2013; 70(10)1288-95.
Genese et al. The influence of sepsis on sleep architecture in the intensive care unit. Meeting of the Society of Critical Care Medicine. Feb. 2016, Orlando, FL S/A, D/T.
Gentil et al. Enhancement of postoperative desaturation in heavy snorers. Anesth Analg, 1995. 81(2): p. 389-92.
Gisolf et al. Human cerebral venous outflow pathway depends on posture and central venous pressure. J Physiol 560.1 (2004) 317-327.
Gupta et al. Postoperative complications in patients with obstructive sleep apnea syndrome undergoing hip or knee replacement: a case-control study. Mayo Clinic Proceedings, 2001. 76: p. 897-905.
Haba-Rubio et al. Obstructive sleep apnea syndrome: effect of respiratory events and arousal on pulse wave amplitude measured by photoplethysmography in NREM sleep. Sleep Breath (2005) 9: 73-81.
Hug et al. Surface EMG to assess and quantify upper airway dilators activity during non-invasive ventilation. Respir Physiol Neurobiol 2011; 178(2):341-5.
Iacobone et al. Sepsis-associated encephalopathy and its differential diagnosis. Crit Care Med 2009; 37(10): S331-336.
International Search Report and Written Opinion for PCT/US2009/059836 dated May 13, 2010.
International Search Report and Written Opinion for PCT/US2010/027679 dated Oct. 19, 2010, 11 pages.
International Search Report/Written Opinion issued in PCTUS2007071242 dated Mar. 13, 2008, 11 pages.
Isono. Obstructive Sleep Apnea of Obese Adults, Anesthesiology, vol. 110, No. 4, Apr. 2009, pp. 908-921.

(56) References Cited

OTHER PUBLICATIONS

Jia et al. Design of a wireless EEG system for point-of-care applications. Proc IEEE Annu Northeast Bioeng Conf 2013; 78-79.

Johansson et al. Estimation of respiratory volumes from the photoplethysmographic signal. Part I: Experimental results. Med Biol Eng Comput. Jan. 1999;37(1):42-7.

Johansson et al. Influence of tidal volume and thoraco-abdominal separation on the respiratory induced variation of the photoplethysmogram. J Clin Monit Comput. 2000;16(8):575-81.

Johansson et al.. Estimation of respiratory volumes from the photoplethysmographic signal. Part 2: A model study. Med Biol Eng Comput. Jan. 1999;37(1):48-53.

Extended European Search Report for corresponding EP Patent Application No. 18802747.8, dated Feb. 8, 2021, in 7 pages.

\* cited by examiner

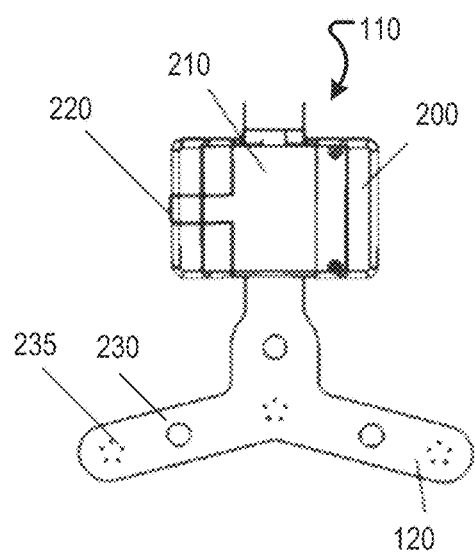
FIG. 2A
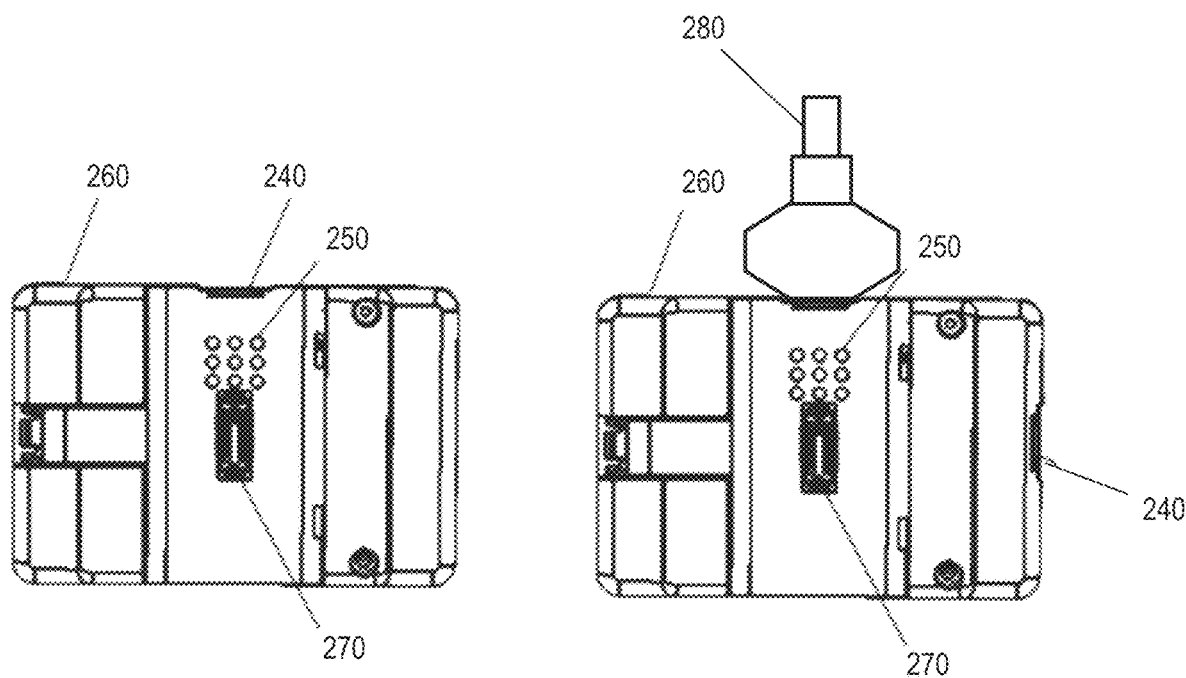
FIG. 2B
FIG. 2C

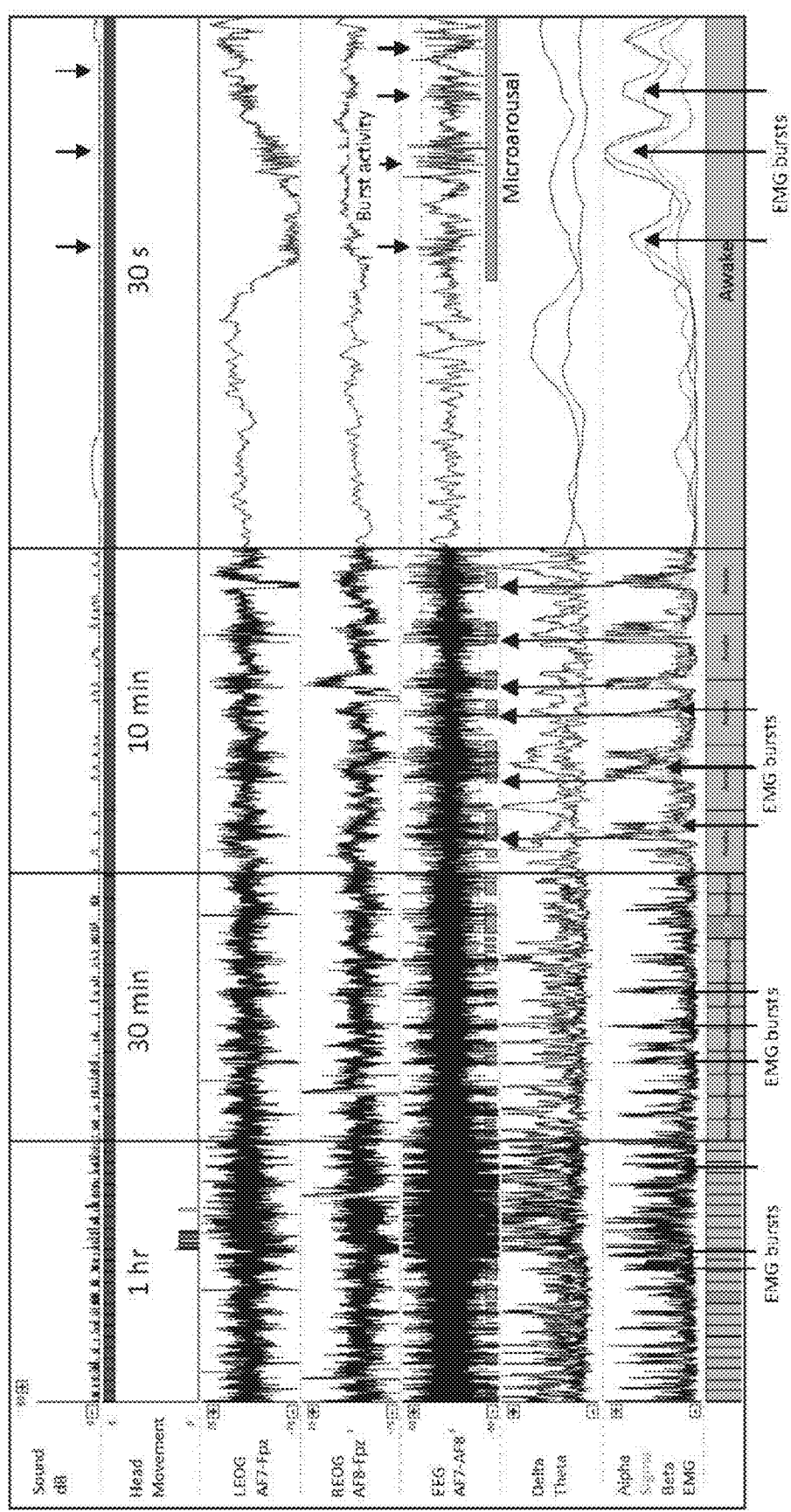

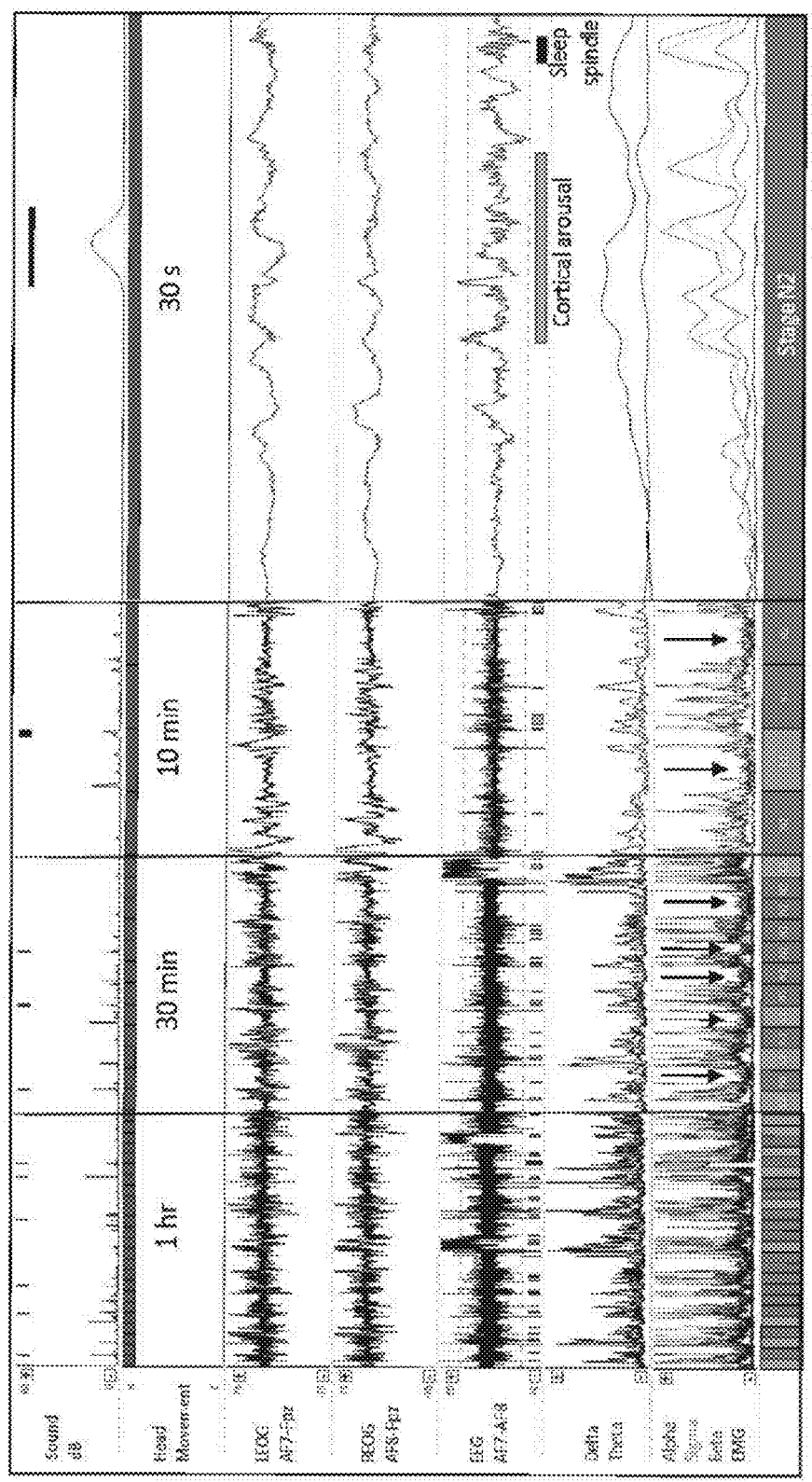

SYSTEMS AND METHODS FOR DETECTING AND MANAGING PHYSIOLOGICAL PATTERNS

CROSS-REFERENCE TO RELATED APPLICATIONS

This application claims priority to U.S. Provisional Patent App. No. 62/508,221, filed on May 18, 2017, and titled "DETECTING AND MANAGING NORMAL AND ABNORMAL NEUROPHYSIOLOGICAL PATTERNS," and U.S. Provisional Patent App. No. 62/620,236, filed on Jan. 22, 2018, and titled "DETECTING AND MANAGING NORMAL AND ABNORMAL NEUROPHYSIOLOGICAL PATTERNS," both of which are incorporated herein by reference in their entireties.

BACKGROUND

Field of the Invention

The embodiments described herein are generally directed to the field of monitoring sleep architecture and more specifically to systems and methods for monitoring and detecting abnormal physiological signal patterns.

Description of the Related Art

Sleep is important to our physical and mental health. The quality and quantity of sleep we obtain impacts our risk for development of chronic diseases, neurodegeneration and mood disorders, and influences the speed of recovery from a hospitalized illness. The electroencephalography (EEG) is commonly used to characterize sleep traditional criteria for staging of epochs of selected time scale (e.g., 30 seconds) into awake; stage N1, NREM (sometimes referred to either N2, N3); or rapid eye movement (REM) sleep. Sleep in intensive care units (ICU), emergency rooms, or other hospital environments may be difficult due to the environmental noise and other factors, resulting in sleep-wake cycle (circadian) disruptions. For example, when the circadian rhythm is disrupted, patients may sleep intermittently during the day and night, rather than having their sleep consolidated during nocturnal hours. This disruption may impair recovery times or lead to additional aliments. Continuous monitoring may then needed to measure the total amount and timing of sleep obtained in a 24-hr cycle. Detecting objective signs of sleep in hospital environments for applying visual scoring techniques to EEG traces may be complicated in part due to disruption of the circadian rhythms. Further complicating the accurate measurement of sleep in the ICU are atypical EEG patterns that inhibited the application of the standard sleep staging rules to EEG signals acquired from ICU patients.

A conventional approach for improving sleep quality for ICU patients is to induce more normal sleep-wake cycles through administration of sedatives according to circadian time (e.g., higher dosage at night). Optimizing ICU sleep around the circadian rhythm can decrease the duration of mechanical ventilation, intubation time, and the length of ICU stay. It can also decrease the amount of sedative drugs used during the day, and reduce the incidence of delirium.

Another cause of sleep disruption in the ICU may be mechanical ventilation, in part as, a result of ineffective patient-ventilator interactions. Patient ventilatory asynchrony impacts as many as 25% of mechanically ventilated patients in the ICU, and contributes to sleep fragmentation, higher sedation levels, delirium, lung injury, prolonged mechanical ventilation and mortality. Sleep architecture may be highly abnormal in mechanically ventilated patients, with decreased REM time and high sleep fragmentation and that three optional types of ventilatory modes may not influence the arousals awakenings or have an ineffective effect. Conversely, patient ventilator discordance may cause sleep disruption, and that proportional assist ventilation may be more efficacious than pressure support ventilation. Neutrally adjusted ventilatory assist (NAVA) may contribute to improved REM sleep, less fragmented sleep, and more effective effort as compared to pressure support ventilation in non-sedated patients. However, NAVA involves insertion of a nasogastric tube mounted with electrode rings to measure the electrical activity of the diaphragm so to obtain a signal that can used to assess dyssynchrony. As an alternative to insertion of a catheter, surface EMG processing may assist in assessing inspiratory drive during mechanical ventilation.

EEG monitoring has primarily focused on the identification of epilepticus waveform/seizure activity, burst suppression, and/or coma-like patterns in the brains electrical activity. Traditionally, long term EEG monitoring (e.g., 24-hour), as opposed to short term monitoring (2-4 hours), has been necessary to identify patients with non-convulsive seizures and periodic epileptiform discharges. The assessment of sleep in the ICU has only been conducted on a research basis due in part to the difficulty of visually staging sleep. The visual characteristics of abnormal large amplitude slow waves which appear during both sleep and awake in the ICU and can be incorrectly assigned stage N3 due to the signal shape. Both polymorphic delta activity and frontal intermittent rhythmic delta activity were detected in ICU EEG measurements.

It is believed that polymorphic delta activity reflecting low-level random inputs to cortical networks, while frontal intermittent rhythmic delta activity (FIRDA) reflected limited-cycle oscillations due to increased excitation. There may be strong relationship between polymorphic delta activity and abnormal cerebral white matter associated with seizures, ischemia/stroke and other causes. Polymorphic delta activity may reflect disturbed neural activity within the full functionality of the brain network. Additionally, cardiac output in stroke patients may be contributed to the generation of FIRDA. Asymmetric FIRDA may also be related to brain lesions and FIRDA may be associated with high risk acute non-convulsive seizure activity. FIRDA has been detected principally in awake patients and occurred in patients with chronic systemic illness.

Burst suppression is another common EEG pattern in ICU patients. Burst suppression in the EEG may be an independent predictor of increased risk of patient death at 6 months. Time in burst suppression during coma may also be an independent predictor of prevalence and time to resolution of post-coma delirium.

Sepsis-associated encephalopathy (SAE) may result from direct cellular damage to the brain, mitochondrial and endothelial dysfunction, neurotransmission disturbances and derangements of calcium homeostasis in the brain tissue. SAE mechanisms may be highly complex, resulting from both inflammatory and non-inflammatory processes that affect all brain cells and induce blood-brain barrier breakdown, dysfunction of intracellular metabolism, brain cell death, and brain injuries. The diagnosis of SAE relies on application of exclusion criteria that can lead to specific neurologic tests, including an EEG.

In some cases SAE may precede the cardinal finding of sepsis, a condition which accounts for up to 50% of the deaths in the ICU. EEG patterns of low-voltage mixed-frequency waves with intermittent amounts of theta and delta waveform activity may be apparent when a patient's eyes are both open and closed, up to 8 hours prior to patients demonstrating clinical signs of sepsis. Triphasic waves and suppression are two EEG patterns that can be found in patients with the most severe form of sepsis. Additional patterns of SAE have been described as diffuse delta waves (<4 Hz) and generalized burst suppression pattern (alternating diffuse reductions in voltage with burst of higher voltage waves). Sepsis-related brain dysfunction may also include sepsis-associated delirium (SAD), suggesting SAE is an early feature of the infection, and abnormal EEG may assist the clinician in defining the severity of SAD. Furthermore, decreased EEG alpha activity has been identified as a biomarker of septic encephalopathy in rats, and may not include the comparison to relative power or the beneficial inclusion of relative or absolute delta, theta, beta, or gamma power.

Patients with mental confusion, or altered wakefulness, may benefit from an evaluation of EEG for detection of non-convulsive seizure activity. At least four conditions have been identified that may benefit from emergency room EEG: evaluation of consciousness or prolonged impairment of consciousness, and/or suspected subclinical or subtle seizure activity, or seizure activity during administration of muscle relaxants for endotracheal intubation. Other conditions may also benefit.

Monitoring burst suppressions may be automated using clustering pattern recognition techniques, for example, for patients in an induced coma. The ratio between alpha and delta activity may be applied to differentiate polymorphic delta activity in the acute and chronic stroke phases of rats. The alpha/sigma ratio may be associated with mortality, sedatives and sepsis. Sepsis may also be associated with an abnormal delta/theta ratio.

A pattern of persistent rhythmic waves or persistent high-amplitude slow waves (<2 Hz) may be obtained with two bipolar left and right leads.

A number of EEG recording systems have been developed. For example, a wireless device has been developed that acquires using dry electrode from a limited montage (Fz, C3, Cz, C4 and Pz). As another example, an EEG system includes an elastic head strap, electrodes and a wireless transmitter, able to acquire EEG from the central and temporal regions. In another example, a wireless EEG acquisition device is provided that is intended for point-of-care applications (e.g., emergency room). An image detection system detects delirium. Many devices have applied bilateral brain monitoring for sedation or anesthesia monitoring. A wireless recorder/monitor has been affixed to the head or forehead of a patient that provides the capability to monitor sleep architecture and continuity.

However, EEG is not routinely monitored in hospitalized patients or patients admitted to the ICU. This is because a trained EEG technician is needed to apply the full montage, continuous EEG acquisition system. Additionally, these conventional EEG acquisition systems are large and expensive, and thus further limit routine monitoring on all patients as a precaution. Another limitation of conventional EEG is that an EEG technician and/or neurologist is needed to monitor the signals in real time to detect abnormal patterns.

SUMMARY

Systems and method for management of sleep quality of a patient are provided herein.

In an embodiment, a method for managing sleep quality of a patient in, for example, a hospital environment such as an emergency room or intensive care unit is provided. The method comprises collecting physiological signal data of the patient using a data acquisition unit electrically coupled to at least one sensor affixed to the patient that generates the physiologic signal data. The method also comprises, using one or more hardware processors executing instructions stored in a storage device, filtering the physiological signal data into a plurality of frequency bands corresponding to a plurality of power spectra waveforms; and characterizing an etiology of sleep quality of the patient based on a comparison of at least a first power spectra waveform of the plurality of power spectra waveforms against at least a second power spectra waveform of the plurality of power spectra waveforms, wherein the sleep quality of the patient is managed based on the characterized etiology of sleep.

In another embodiment, a system for managing sleep quality of a patient is provided. The system comprises a data acquisition unit electrically coupled to at least one sensor affixed to the patient. The data acquisition unit collects physiological signal data of the patient generated by the at least on sensor. The system also comprises at least one hardware processor, and a storage device coupled to the at least one hardware processor and the data acquisition unit. The storage device stores instructions that, when executed by the at least one hardware, are operable to filter the physiological signal data into a plurality of frequency bands corresponding to a plurality of power spectra waveforms, and characterize an etiology of sleep quality of the patient based on a comparison of at least a first power spectra waveform of the plurality of power spectra waveforms against at least a second power spectra waveform of the plurality of power spectra waveforms, wherein the sleep quality of the patient is managed based on the characterized etiology of sleep.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 2A-2C illustrates example enclosures of data acquisition units and interface with the sensor strap according to various embodiments;

FIGS. 9A-11C include data illustrating an example characterizations of acquired physiological signal patterns according to embodiments herein;

FIGS. 20A-20D include data of an example of physiological signal patterns EMG burst patterns indicative of ventilator distress or central sleep apnea associated arousals, in accordance with embodiments herein;

FIGS. 21A-23B include data of examples of physiological signal patterns of abnormal burst suppression, in accordance with embodiments herein;

DETAILED DESCRIPTION

Figure 1:
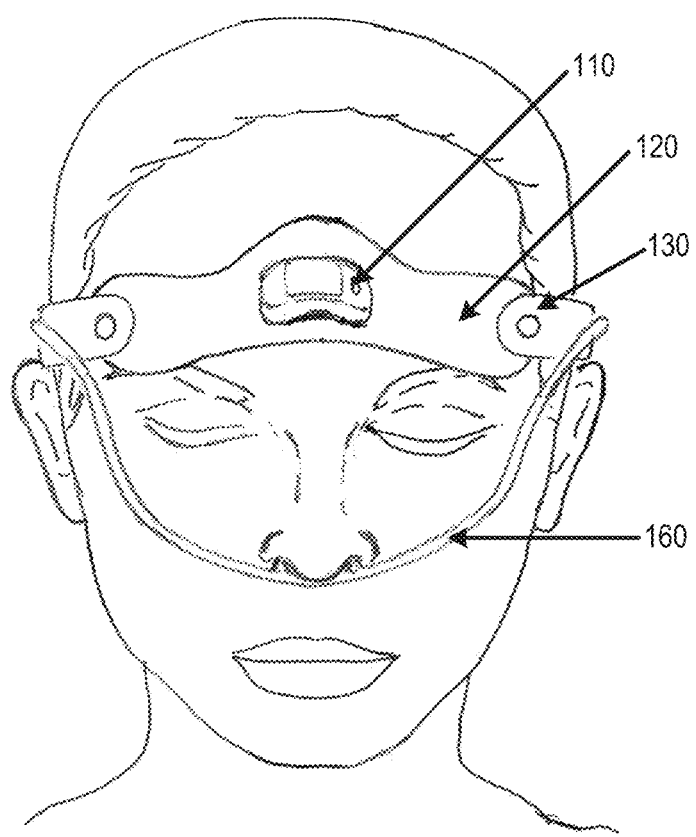
FIG. 1 illustrates a patient with a data acquisition system including a data acquisition unit according to an embodiment.

After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

The described systems and methods are based on the acquisition and analysis of neurophysiological signals (also referred to herein as "physiological signals"). In some embodiments, the systems and methods described herein may provide for real-time monitoring of sleep architecture. In various embodiments, the systems and methods may provide for human and/or automated recognition of distinctive physiological signal characteristics that may be used to trigger interventions. Such interventions may be executed via human interaction and/or automated via computer or systems. Several embodiments utilize a data acquisition unit (DAU) that acquires and/or transmits physiological signals from which of a quality of sleep of a patient may be monitored and/or identified. These signals may be presented in a graphic user interface in order to characterize the signals and quantify the patients sleep. Alternatively, the signals may be characterized through processing techniques to identify and detect distinctive signal patterns indicative of abnormal conditions and/or sleep architecture. Such characterization may be beneficial in hospitalized patients to monitor and stage the patients sleep patterns to improve recovery time and care.

The described systems and methods combine automated detection of signal patterns with presentation techniques that may allow caregivers with limited neurophysiological training or expertise to detect and differentiate normal and abnormal physiological signal patterns. In an embodiment a DAU can be adapted for use as a periodic or continuous monitoring of physiologic signals. Various embodiments of the methods described herein extract elements of normal and abnormal physiological signal patterns for use in directing patient care. In one embodiment the pattern detection includes quantification of sleep architecture and sleep continuity for accurate detection of etiological sleep/wake (e.g., etiology of sleep quality) in patients hospitalized, medicated, and/or critically ill. The systems and methods also can include monitoring quantity of sleep, patterns of disruptions that will result in poor sleep quality, impact of interventions and/or medications, and effectively managing abnormal neurological activity. Descriptions of additional means for detection of patterns of normal brain wave activity and abnormal brain wave activity associated with poor outcomes, sepsis, or mortality is provided. Various embodiments utilize a unique graphical user interface that improves presentation of both the physiological signals and extracted features, while also displaying power spectral characteristics derived from the neurophysiological signals (e.g., EEG, EOG, ECG, etc.). Another aspect is that different signal feature characteristics can be viewed on different time scales selected to optimize visual detection of the targeted signal patterns. These feature characteristics can be monitored either offline or in real time, and that current or previously acquired data can be readily accessed and reviewed.

Various embodiments herein provide for the analysis and/or presentation of the physiological signals, sleep/wake, and power spectra as a screening tool by users (e.g., non-experts and/or experts) that provide for improved detection of abnormal signal patterns. Such abnormal signal patterns may include, but are not limited to, burst suppression and non-convulsive epileptiform activity, which may necessitate patients being placed on conventional (10-20 montage), continuous EEG monitoring. Further, the approaches described herein for remote or offsite viewing that can also be applied to analyze and transmit the data signals obtained from the continuous EEG monitoring system. The capability of experts to review the studies of different patients from different hospitals, and from both screening and continuous monitoring systems will improve the health and wellbeing of a greater number of patients, and improve the productivity of the experts.

As used herein, a "patient" may be a person from which physiological signal data is collected therefrom, for example, using the systems and devices described herein. Furthermore, as used herein a "user" may be any person or device that reviews, analysis, processes, evaluates, or otherwise interactions with collected data representative of psychological signals. For example, in some embodiments, a user may be a health-care provider, medical personnel, hospital employee, or the like. In another embodiment, alternatively or in combination, a user may refer to a nurse, doctor, and/or specialist (e.g., an expert) of any given medical field. In yet another embodiment, a user may refer to a computer device and/or mobile device configured to process the collected data and perform some action in response thereto.

FIG. 1 illustrates a patient with the data acquisition system including a data acquisition unit (DAU) 110 and a sensor strap 120. The data acquisition system can be used to collect and store physiological signals from a user while the user is sleeping in order to assess sleep quality, for example, an etiology of sleep. According to an embodiment, the data acquisition system can connect to an external computer system that is configured to process the data collected by the data acquisition system (see FIG. 5 described below). In some embodiments, the data acquisition system can be configured to perform at least some analysis on the data collected before the data is downloaded to the external computer system. The data acquisition system may be substantially similar to the systems and devices described in detail in, for example, U.S. Pat. Nos. 8,355,769 and 8,639,313, both of which are incorporated herein by reference. Embodiments described therein provide systems and method to acquire and/or transmit physiological signals used to assess sleep architecture and sleep continuity. For example, a DAU is described that can be used to acquire a number of physiological signals from the forehead including electroencephalographic (EEG), electrooculargraphic (EOG) and electromyographic (EMG) signals, head movement and position obtained with a 3D accelerometer, pulse rate, and snoring sounds measured with an acoustic microphone. Such implementations included concomitant monitoring of respiratory patterns for the assessment of sleep and breathing abnormality.

Referring again to FIG. 1, an embodiment of the data acquisition system is illustrated comprising a headband 130, a sensor strap 120, an optional nasal cannula 160, and a headband 130. In some embodiments, a top strap and/or nasal mask (not shown) may be optional. Furthermore, FIG. 1 illustrates the DAU 110 mounted directly over the sensor strap 120 when affixed to the forehead, however in some embodiments the DAU 110 may be positioned further up on the head. Either implementation is able to acquire signal data from the frontoplanar sites of the patient's forehead. While example embodiments are illustrated herein, one skilled in the art will appreciate that the components of the data acquisition system may be arranged in any combination of arrangements shown in FIG. 1.

DAU 110 can be worn above the forehead of the patient and/or attached to the sensor strap 120 during sleep to collect physiological signal data. In the embodiment illustrated in FIG. 1, the DAU 110 is integrated or coupled with a sensor strap 120 and a nasal pneumotachometer (now shown). An embodiment of the sensor strap 120 is described below in connection with FIG. 2A. A headband 130 encircles the rear of the patient's head to hold the data acquisition system in place. A top strap may also extend over the back of the patient's head where it joins the headband 130 for additional stability. Sensor strap 120 can be coupled to headband 130 to hold the sensor strap 120 in place over the user's forehead.

According to an embodiment, the headband 130 and/or the top strap can be adjusted in size to accommodate users having different sized heads. In some embodiments, can be removed and replaced with different sized headbands and top straps to accommodate different users. Furthermore, the headband and top straps can be designed to be one-time-use components for sanitary purposes that can be removed while allowing the data acquisition unit and/or other components of the apparatus to be used by another user.

In an embodiment, the DAU 110 includes physiological acquisition and storage circuitry configured to assess sleep quality or record data for use in assessing sleep quality. As described below, the assessment of sleep quality includes performing concurrent measurements of a plurality of categories of signal data, including but not limited to: (1) signal data related to sleep states, and (2) signal data related to the type of sleep disruption. DAU 110 is configured to perform the concurrent measurements of the sleep data, record these measurements, and in some embodiments, analyze and process the recorded data. In various embodiments, the sensor strap 120 may be configured to acquire signal data from less than a full montage (e.g., 10-20 montage) of the conventional EEG monitoring systems. For example, the sensor strap 120 may acquire signals from the full 10-20 montage system sites of AF7, AF8 and Fpz. The DAU 110 and sensor strap 120 can be used to implement the methods or as part of the systems described in, for example, FIGS. 4-31. According to some embodiments, DAU 110 can be positioned near the top of the head of the user or positioned over the forehead of the user (as illustrated in FIG. 1). The position of the DAU 110 can be based in part on the type of assessment to be performed and the types of sensor data used to make that type of assessment.

According to an embodiment, sensor strap 120 may be removable, and in some embodiments, sensor strap 120 can also be disposable. For example, the sensor strap 120 can be configured to be electronically coupled to the DAU 110 using a socket connection or other type of connection that allows the sensor strap 120 to be removed and replaced. This can allow the sensor strap to be replaced for sanitary purposes (as well as the top strap and/or the headband, as described above) to allow the DAU 110 to be used again with another user. In an embodiment, the sensor strap 120 can be a one-time-use strip that is provided in a sealed sterile package. In some embodiments, elements of sensor strap 120 can be disposable, while some components are reusable. For example, the sensor strap 120 may include disposable EEG sensors and a reusable the pulse/oximetry sensor.

According to an embodiment, sensor strap 120 can also include an adhesive backing that helps to facilitate and maintain placement of the sensor strap 120 on the user's forehead region by removeably adhering to the user's skin. In one embodiment, the sensor strap 120 can comprise adhesive backed foam. The adhesive backing can also help to maintain sensor contact with the user's skin for those sensors that require skin contact. According to some embodiments, conductive sensors included in the sensor strap 120 can have a conductive gel placed over theses sensors. FIG. 2A, described below, illustrates some example of the types of sensors than be included in the sensor strap 120. The configuration of the sensor strap 120 facilitates use of the data acquisition system by users by making proper placement and attachment of sensors much easier than conventional systems. For example, some conventional EEG monitoring systems require that numerous electrodes be affixed to a patient's head. Proper placement of the electrodes is important. As a result, EEG data is often gathered in a clinical setting where the electrodes can be affixed to the patient by a clinician. When performing sleep studies, this can have a negative impact on the results of the study, because the user is removed from his or her normal sleeping environment and placed into an unfamiliar clinical setting. The sensor strap 120 used with the data acquisition systems disclosed herein facilitates home use of the device by making proper placement of the sensors easy for patients, thereby allowing users to gather data at home where they are likely to be more comfortable and more likely to experience sleep episodes that are more typically of their regular sleep episodes. Additionally, the sensor strap 120 used with the DAU disclosed herein facilitates hospital, emergency, ICU, out-patient, etc. use of the device by making proper placement of the sensor easy by caregivers that lack specific expertise in performing sleep studies, thereby allowing caregivers to gather data in emergency situations and/or out-side of specifically designated clinical environments where the patient may be more comfortable. Furthermore, this system permits the caregivers to easily and inexpensively monitor the sleep episodes of the patient in any given environment to improve recovery time.

FIGS. 2A-2C illustrate views of an enclosure of the DAU 110 and the interface with sensor strap 120 according to various embodiments. The DAU enclosure 200 includes a removable back cover 210 with a securing push tab 220 that holds the sensor strap 120 in place during use. Removal of the back cover exposes the micro-USB connector 240 and heat dissipating vent holes 250 which allow for data transfer and battery recharging. According to an embodiment, the connectors that allow the device to be connected to an external power source, such as alternating current power from the mains power, are not accessible when the system being worn by a user. In an embodiment, electrical pathways between the sensors and the electronics can be interfaced with one touch-proof connector for the ECG leads 260 and a connector 270 in the center of the enclosure 200 for the sensor strap.

In some embodiments the DAU 110 may comprise a nasal pressure transducer disposed within the DAU enclosure 200 (e.g., FIGS. 2A and 2B). Alternatively, in some embodiments, a nasal pressure transducer 280 may be affixed to the enclosure as illustrated in FIG. 2C and attached to the optional nasal cannula 160 of FIG. 1. One non-limiting advantage of the optionally affixed nasal pressure transducer 280 is that it may reduce the size and weight of the DAU 110 as well as reduce manufacture complexity and costs.

Figure 3:
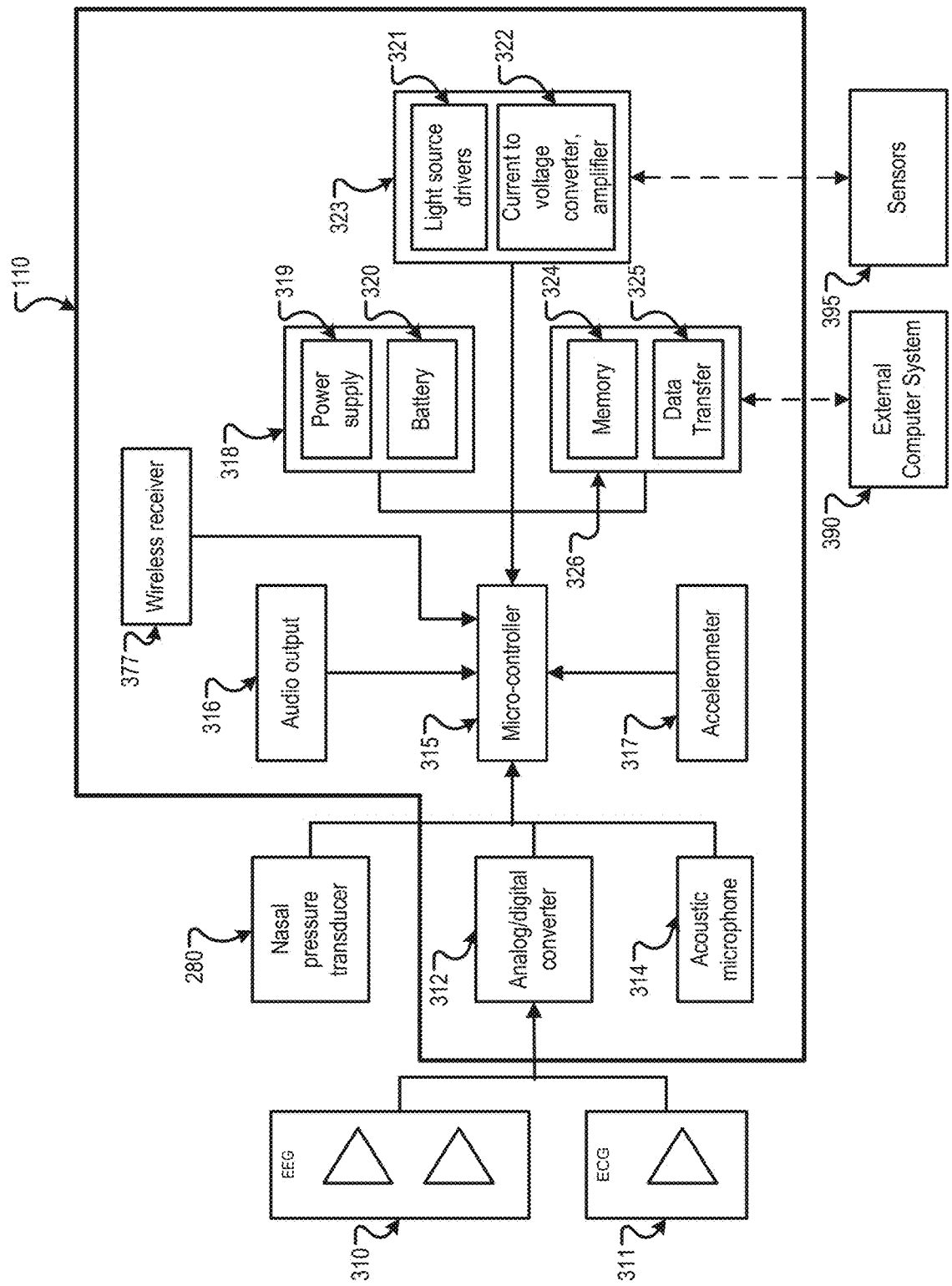
FIG. 3 is a block diagram identifying functional components and circuits of a data acquisition unit according to an embodiment.

FIG. 3 is a block diagram identifying functional components and circuits of a data acquisition apparatus for quantifying sleep quality according to an embodiment. In the illustrated embodiment, DAU 110 comprises an analog-to-digital converter 312, an acoustic microphone 314, a microcontroller 315, an audio output 316 (e.g., speaker), an accelerometer 317, a battery power component 318 (e.g., comprising a power supply 319 and/or battery 320), a sensor driving unit 323 (e.g., comprising an optical signal amplifier that includes digitally programmable potentiometers 321 and/or means to convert and amplify outputs from a photodiode 322), a data transfer module 326 (e.g., comprising a data storage device or memory 324 and/or data transfer interface 325), and/or a wireless transmitter, receiver, or transceiver 377. In addition, DAU 110 may be communicatively connected to a nasal pressure transducer 313, one or more EEG sensors 380, one or more ECG sensors 381, one or more other sensors 395 (e.g., via sensor driving unit 323), and/or an external computer system 390 (e.g., via data transfer module 326). It should be understood that, in alternative embodiments, DAU 110 may have fewer, more, or different components (e.g., different types or combinations of sensors, embedded sensors, no acoustic microphone 314, no audio output 316, no accelerometer 317, no sensor driving unit 323, etc.), as well as a different arrangement of components (e.g., an external power supply), than those illustrated in FIG. 3.

The analog-to-digital converter 312 may provide for amplifying and digitizing two channels of EEG/EOG data 310 for measuring sleep architecture and cortical arousals, and one channel of ECG data 311 to assess heart rate and autonomic/cortical arousals. According to other embodiments, any combination of EEG channels could be employed. However, a single channel of EEG can reduce the accuracy of the sleep stage measurement and more than two channels can increase the size of the DAU without significantly increasing detection accuracy. The use of two channels can significantly increase the system's ability to differentiate REM from NREM sleep on the basis of rapid conjugate eye movements that are characteristic of REM sleep and appear as large voltage deflections that are out of phase in the two EEG channels. According to an embodiment, the EEG/EOG data 310 and EEG data can be captured using electrodes integrated into sensor strap 120. FIG. 2A, which is described in detail above, provides an example embodiment of one possible configuration of the sensor strap 120 that includes EEG/EOG/EMG electrodes for gathering the EEG/EOG data 310 and the ECG data 311.

DAU 110 is configured to receive a signal from a nasal pressure transducer 313 to acquire airflow data. The airflow data can be used in identifying sleep disruptions, such as apnea. In an embodiment the dynamic range of the pressure transducer is set to optimize airflow resolution of (i.e., +/−2 cm/H20).

Acoustic microphone 314 can also be used to detect snoring and/or other audible symptoms that can be causing sleep disruption. DAU 110 includes an amplification circuit that receives and amplifies sound signals from acoustic microphone 314. In some embodiments, the acoustic microphone 314 can be integrated into the DAU 110, while in other embodiments, the acoustic microphone 314 can be included in the sensor strap 120 or affixed to the headband 130. In an embodiment, a high fidelity sound is sampled between 2 to 4 kilohertz to profile snoring pattern and to recognize the region of airway obstruction as well as assess nocturnal coughing and wheezing. Alternatively, in some embodiments, snoring sounds can be quantified by rectification, integration, and sampling at a reduced frequency (e.g., 10 Hz) or with sensors limited to qualitative measures (e.g., vibration).

The DAU 110 includes an accelerometer 317 that can measure a full range of head positions, including both sleep and wake conditions, as well as behavioral arousals defined by subtle head movements.

In the embodiment illustrated in FIG. 3, the DAU 110 includes a battery power component 318 that includes a rechargeable lithium polymer battery 320 and a power supply 319 and recharging circuitry for receiving power from an external source for recharging battery 320 and/or powering the DAU 110. The battery power component 318 allows the DAU 110 to operate without requiring the DAU 110 to be tethered to an external power cord or power supply, which could be inconvenient and uncomfortable for a user of the device. According to some embodiments, an external power supply can be used to power the device. According to other embodiments, battery 320 can be another type of battery 320 and in some embodiments battery 320 can be removable and replaceable.

A sensor driving unit 323 is included to provide a driving current to drive red and infrared light emitting diodes used in conjunction with sensors 395 to gather physiological data. The DAU 110 also includes an optical signal amplifier that includes digitally programmable potentiometers 321 and a means to convert and amplify outputs from a photodiode 322. According to an embodiment, the sensors 395 can be included in the sensor strap 120.

The DAU 110 can include a storage device, e.g., a memory 324 for data storage. In an embodiment, the memory 324 can comprise a removable Multimedia Memory or Secure Digital card or other types of removable persistent memory. In another embodiment, the memory 324 can comprise a fixed flash chip. According to an embodiment, a data transfer interface 325 is provided. According to an embodiment, the data transfer interface comprises a USB data transfer chip. In another embodiment, USB transfer capabilities can be incorporated into micro-controller 315.

According to an embodiment, firmware is stored in a memory 324 associated with micro-controller 315. According to an embodiment, the memory 324 is a flash memory. According to some embodiments, the firmware can be updated via data transfer interface 325. Furthermore, according to some embodiments, the memory 324 and can be part of a persistent memory.

In an embodiment, the firmware is configured to routinely sample and save signal data received by the DAU 110. According to an embodiment, filtering routines can be used to detect poor quality signal data and to notify the user via an audible signal generated using audio output 316 or via a piezo-electric buzzer. For example, if the user has misaligned the position of the sensor strap 120 on the forehead, the signals received from the sensor strap 120 may of poor quality. The DAU 110 can generate an audible alarm or vibrate if the sensor strap needs to be realigned.

In one embodiment, DAU 110 can include a wireless transmitter/receiver 377 for receiving data from peripheral sensors (i.e., wireless ECG sensors, finger pulse oximeter, respiratory effort bands, sensors measuring leg movements, etc.) and/or transmit signals to an external computer system 390 for real time monitoring of the data being acquired by the DAU 110. Data acquired from these sensors can be used to determine the user's sleep architecture and/or to identify sleep disruptions that can negatively impact sleep quality. In some embodiments, the wireless transmitter/receiver 377 can be integrated into data transfer module 326 of DAU 110.

According to an embodiment, micro-controller 315 can be based on an ARM 32-bit reduced instruction set computer (RISC) instruction set or equivalent architecture. Firmware can be configured to minimize the power requirements of the ARM chip when the DAU is being used in recording mode. The computational capacity of the ARM chip can provide the option for firmware to transform the signals during acquisition or prior to data download. For example, fast-Fourier transforms can be applied to a 512 samples/second EEG signal can quantify the high frequency power spectral densities of the EEG or EMG without requiring the large data files to be transferred off line to make this computation. Once high resolution power spectra are computed the EEG can be saved at 64 samples/second for purposes of visual inspection. Given the preference to obtain high fidelity sound signals, in some embodiments it would be beneficial the two-kilohertz signal can be pre-processed and down sampled to reduce data transfer time without compromising analytical power. This approach to down-sampling significantly reducing the size of and time to transfer data files from the DAU 110 to an external computer system 390 for analysis. In alternative embodiments, a lower-powered micro-controller is used when the DAU is used as a recorder. The micro-controller and also include features such as a temperature monitor, analog to digital converter, and/or the capability to transfer the data file in USB format to reduce the need for extra components.

Figure 4:
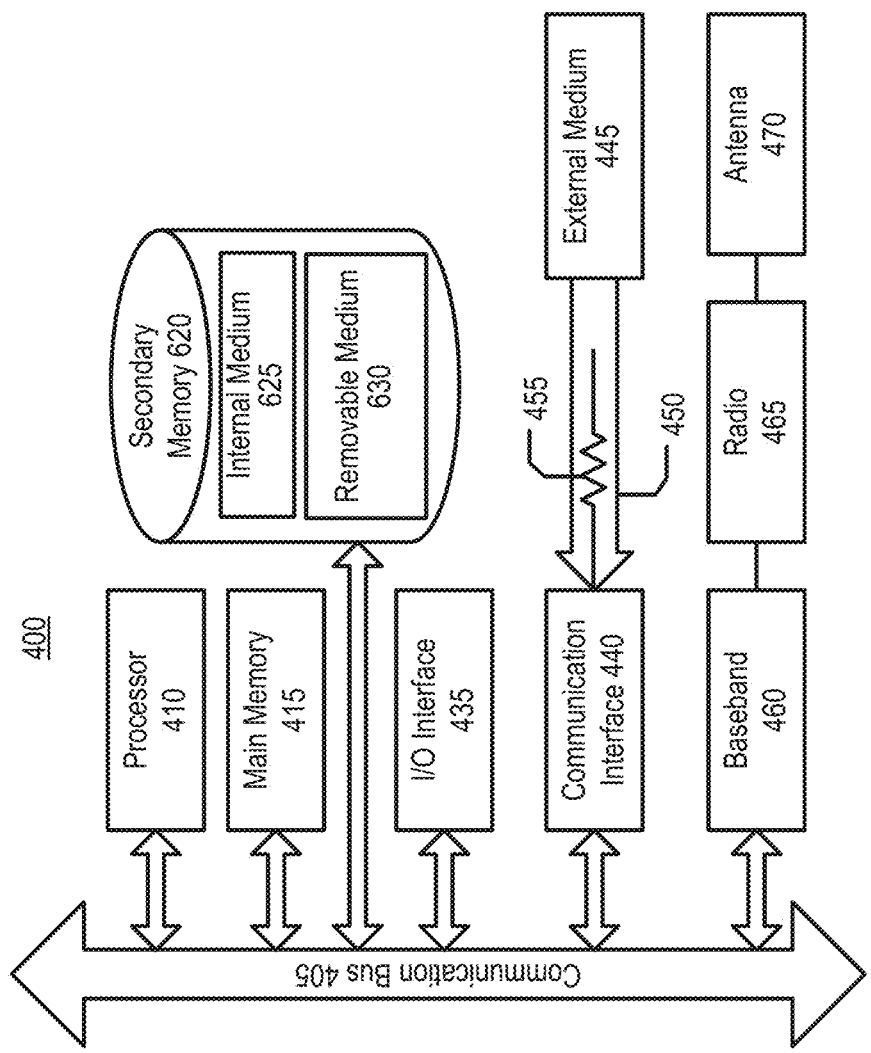
FIG. 4 illustrates an example processing device on which one or more of the processes described herein may be executed, according to an embodiment FIG. 5 schematically illustrates an integrated system for monitoring physiological signal patterns of one or more patients, in accordance with various embodiments.

FIG. 4 is a block diagram illustrating an example computer system 400 that may be used in connection with various embodiments described herein, according to an embodiment. For example, FIG. 4 illustrates an exemplary computer system that can be used in conjunction the DAU 110 according to an embodiment. In some embodiments, the computer system 400 may be implemented as external computer system 390 in, for example, an ICU, emergency room, hospital environments, out-patient environments, a user's home, or etc. In some embodiments, the external computer system 390 is a medical personnel's computer system 560 or mobile device 550. For example, medical personnel wishing to perform a sleep assessment on a patient can issue a DAU 110 to the patient. The DAU 110 can be used in any desired environment local to or remote from the medical personnel to capture sleep related data and return the DAU 110 to the medical personnel who can then download the data from the DAU 110 in order to assess the sleep quality of the patient. The system 400 may be used as or in conjunction with or as components of one or more of the mechanisms, processes, or devices described elsewhere herein, including those components illustrated in FIG. 6 below. As will be clear to those skilled in the art, alternative processor-enabled systems and/or architectures may also be used.

In addition, the computer system 400 may support or implement any other conventional or future method of user interaction. Such methods may include augmented reality (e.g., overlaying any of the visual elements described herein over a real-time image of the user's physical environment), virtual reality (e.g., providing a virtual universe in which the user can move and with which the user can interact using conventional virtual reality gear, such as a headset, hand paddles, etc.), and/or the like.

The system 400 preferably includes one or more processors, such as processor 410. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 410. Examples of processors which may be used with system 400 include, without limitation, the Pentium® processor, Core i7® processor, and Xeon® processor, all of which are available from Intel Corporation of Santa Clara, Calif.

The processor 410 is preferably connected to a communication bus 405. The communication bus 405 may include a data channel for facilitating information transfer between storage and other peripheral components of the system 400. The communication bus 405 further may provide a set of signals used for communication with the processor 410, including a data bus, address bus, and control bus (not shown). The communication bus 405 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 400 preferably includes storage devices, such as, a main memory 415 and an optional secondary memory 420. The main memory 415 provides storage of instructions and data for programs executing on the processor 410, such as one or more of the functions and/or methods discussed above. It should be understood that programs stored in the memory and executed by processor 410 may be written and/or compiled according to any suitable language, including without limitation C/C++, Java, JavaScript, Perl, Visual Basic, .NET, and the like. The main memory 415 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 420 may optionally include an internal memory 425 and/or a removable medium 430, for example a floppy disk drive, a magnetic tape drive, a compact disc (CD) drive, a digital versatile disc (DVD) drive, other optical drive, a flash memory drive, etc. The removable medium 430 is read from and/or written to in a well-known manner. Removable storage medium 430 may be, for example, a floppy disk, magnetic tape, CD, DVD, SD card, etc.

The removable storage medium 430 is a non-transitory computer-readable medium having stored thereon computer executable code (i.e., software) and/or data. The computer software or data stored on the removable storage medium 430 is read into the system 400 for execution by the processor 410.

In alternative embodiments, secondary memory 420 may include other similar means for allowing computer programs or other data or instructions to be loaded into the system 400. Such means may include, for example, an external storage medium 445 and an interface 440. Examples of external storage medium 445 may include an external hard disk drive or an external optical drive, or and external magneto-optical drive. External storage medium 445 may also be cloud storage.

Other examples of secondary memory 420 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 430 and communication interface 440 which allow software and data to be transferred from an external medium 445 to the system 400.

According an embodiment, the main memory 415 and/or secondary memory 420 may comprise a patient data store, a reporting data store, a disease management recommendations (e.g., recommendations and/or interventions) data store, and a comparative data data store. In an embodiment, the data stores can be relational databases or other types of persistent and searchable data stores in memory 415 of computer system 400. According to some embodiments, one or more of the data stores can be stored on an external server and can be accessed by external computer system 390 via a network connection.

The patient data store may store patient related data, e.g. a patient identifier and/or patient demographic information. Patient data store may also include information of related ailments, diseases, etc. indicative of the acute status of the patient. The patient data store may also include modified sleep staging rules as described in more detail below in connection to FIG. 12. Patient data from the patient data store can be used in the various assessments described herein for assessing the sleep quality of the user. The reporting data store can be used to store generated reports and can also include report templates that can be used to determine the format of the report and/or the types of analysis to be included in the reports. The disease management recommendations data store can be used to store various treatment recommendations and/or intervention parameters that can be included in patient reports based on the analysis of the data gathered by the DAU 110 and used to make adjustments to the patient's care. The comparative data data store can be used to store comparative data from healthy patients and/or patients with a chronic illness that causes sleep quality to degrade. The comparative patient data can be used, in part, to assess the sleep quality of a patient by providing a baseline of healthy and ill patients against which a user's data can be compared.

System 400 may include a communication interface 440. The communication interface 440 allows software and data to be transferred between system 400 and external devices (e.g. printers), networks, displays, or information sources. For example, computer software or executable code may be transferred to system 400 from a network server via communication interface 440. Examples of communication interface 440 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of system 400 with a network or another computing device.

Communication interface 440 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 440 are generally in the form of electrical communication signals 455. These signals 455 are preferably provided to communication interface 440 via a communication channel 450. In one embodiment, the communication channel 450 may be a wired or wireless network, or any variety of other communication links. Communication channel 450 carries signals 455 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 415 and/or the secondary memory 420. Computer programs can also be received via communication interface 440 and stored in the main memory 415 and/or the secondary memory 420. Such computer programs, when executed, enable the system 400 to perform the various functions of the present invention as previously described.

In this description, the term "computer readable medium" is used to refer to any non-transitory computer readable storage media used to provide computer executable code (e.g., software and computer programs) to the system 400. Examples of these media include main memory 415, secondary memory 420 (including internal memory 425, removable medium 430, and external storage medium 445), and any peripheral device communicatively coupled with communication interface 440 (including a network information server or other network device). These non-transitory computer readable mediums are means for providing executable code, programming instructions, and software to the system 400.

In an embodiment that is implemented using software, the software may be stored on a computer readable medium and loaded into the system 400 by way of removable medium 430, I/O interface 435, or communication interface 440. In such an embodiment, the software is loaded into the system 400 in the form of electrical communication signals. The software, when executed by the processor 410, preferably causes the processor 410 to perform the inventive features and functions previously described herein.

In an embodiment, I/O interface 435 provides an interface between one or more components of system 400 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 400 also includes optional wireless communication components that facilitate wireless communication over a voice and over a data network. The wireless communication components comprise an antenna system 470, a radio system 465 and a baseband system 460. In the system 400, radio frequency (RF) signals are transmitted and received over the air by the antenna system 470 under the management of the radio system 465.

In one embodiment, the antenna system 470 may comprise one or more antennae and one or more multiplexors (not shown) that perform a switching function to provide the antenna system 470 with transmit and receive signal paths. In the receive path, received RF signals can be coupled from a multiplexor to a low noise amplifier (not shown) that amplifies the received RF signal and sends the amplified signal to the radio system 465.

In alternative embodiments, the radio system 465 may comprise one or more radios that are configured to communicate over various frequencies. In one embodiment, the radio system 465 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 465 to the baseband system 460.

The baseband system 460 is also communicatively coupled with the processor 410. The processor 410 has access to data storage areas 415 and 420. The processor 410 is preferably configured to execute instructions (i.e., computer programs or software) that can be stored in the memory 415 or the secondary memory 420. Computer programs can also be received from the baseband processor 460 and stored in the data storage area 415 or in secondary memory 420, or executed upon receipt. Such computer programs, when executed, enable the system 400 to perform the various functions of the present invention as previously described. For example, data storage areas 415 may include various software modules (not shown).

According to an embodiment, DAU 110 can be configured to perform various processes on the data collected from the sensors and to download the processed data to computer system 400. According to some embodiments, the DAU 110 can capture and store data from the various sensors and the data is downloaded to computer system 400 for processing. As described above, the DAU 110 can include firmware that performs at least a portion of the processing of the signal data collected before the data is downloaded to the computer system 400.

According to an embodiment, the computer system 400 can be used to view data (e.g., via a display connected at I/O interface 435) collected and/or analyzed by DAU 110 and/or perform analysis and processing on the collected data. According to an embodiment, the computer system 400 can also generate reports based on the data collected by the DAU 110. In various embodiments, the computer system 400 may perform actions (e.g., interventions, feedback, stimulus, etc.) based on the analyzed data to control and/or steer the patient into a desired sleep state and/or away from or out of undesired sleep states, as described below in connection to FIGS. 6-28.

According to an embodiment, the DAU 110 can include software for downloading data captured by the DAU 110 and/or the sensors interfaced with the DAU 110 to a remote computer system (e.g., computer systems 390, 560 or mobile device 550 described below in connection with FIG. 5) via a network and/or cloud server 540. For example, in an embodiment, the DAU 110 can include software that periodically connects to external computer system 390 via a wireless interface, downloads data from the DAU 110 to the external computer system 390, and triggers a transfer of the data from the external computer system 390 to a remote computer system 560, such as a doctor's computer system or a web portal. In an embodiment, the remote computer system can be a web portal comprising one more remote servers that can collect and analyze data received from DAU units. For example, a doctor treating a patient can create an account on the web portal for that patient and associate the account with a particular DAU 110. The patent can then use the DAU 110 to capture data DAU 110 may perform one or more of the steps in the various processes described herein, including one or more of the steps in the processes illustrated in FIGS. 6-28 described below. In addition, external computer system 390 may perform other ones of the steps in these processes. For example, DAU 110 may perform steps corresponding to the collection of data, signal processing, etc., whereas external computer system 390 may perform steps corresponding to the analysis of the collected data (e.g., calculation of metrics, etc., based on the collected data) and the display of graphical user interfaces, reports, etc. related to the analysis (e.g., visual results of the analysis).

In some embodiments, DAU 110 can be integrated with one or more wireless sensors for measuring various physiological data that can be used to identify sleep disruptions. For example, sensor of the DAU 110 may comprises wireless sensors used to measure pulse/oximetry from the finger, a device that obtains electro-cardiographic signals (e.g., holter monitor), respiratory effort belt, and transducer to measure limb movements. However, in other embodiments other types of sensors for measuring physiological signal data can be used and different combinations of sensors can be used. The data from these sensors can be used to collected data used by the DAU 110 in the concurrent measurement of signal data related to sleep architecture and of signal data related to sleep disruptions.

As described above, DAU 110 can include a wireless transmitter/receiver 377 incorporated into the data transfer module 326 to receive data from peripheral sensors (i.e., wireless ECG sensors, finger pulse oximeter, respiratory effort bands, sensors measuring leg movements, etc.) and/or transmit signals to an external computer system 390 for real time monitoring of the data being acquired by the DAU 110. Data acquired from these sensors can be used to determine the user's sleep architecture and/or to identify sleep disruptions that can negatively impact sleep quality.

According to an embodiment, each of these wireless sensor sub-systems can have a separate power supply and data storage. The DAU 110 and the wireless sensor sub-systems can be integrated to align the data from the sensor sub-systems with the data generated by the DAU 110. For example, the data can be aligned by using a common time stamp on all data that can be used to determine when data was recorded by the DAU 110 and/or the sensor sub-systems. According to an embodiment, this integration can be achieved by configuring the DAU 110 or one of the sensor sub-systems to operate to serve as a master device that wirelessly transmits a time stamp that is received by the other integrated components of the system. Each of the components of the system can include a wireless receiver for receiving the timestamp information and be configured to use the timestamp information transmitted by the master device to synchronize an internal clock to that of the master device or to use the timestamp information transmitted from the master device to timestamp data generated by the receiving device. According to an alternative embodiment, the sensor sub-systems can be integrated with the DAU 110 by coupling the DAU 110 to the sensor sub-systems using a wire. In such a wired configuration, the DAU 110 and the sensor sub-systems can operate using a common power supply and use common data storage.

In an embodiment, central sympathetic arousals or variability in sympathetic activation can be measured with two dry electrodes (i.e., capable of acquiring the ECG signal through clothes). One benefit of recording ECG is to more accurately identify cardiac problems (e.g., cardiac dysrhythmia, etc.). Alternatively, sympathetic arousals can be detected with a pulse signal or peripheral arterial tone signal. The pulse signal can be obtained using a sensor located at the user's forehead or any other location (e.g., ear, finger, etc.) which obtains capillary blood flow and is appropriate for either reflectance or transmittance methodologies/technology.

According to an embodiment, electro-neuro-cardio-respiratory sensors used to assess sleep quality can be incorporated into the sensor strap 120. As described above, the sensor strap 120 can be removeably coupled to the DAU 110 via a socket connection on the DAU 110 that electrically couples traces included in the sensor strap 120 with the DAU 110.

As shown in FIG. 2A, the sensor strap 120 can be used to acquire physiological signals that can be used in the concurrent measurements related to sleep architecture and sleep disruptions that is performed by the DAU 110 according to an embodiment. The sensor strap 120 includes traces that create electrical circuit connections while holding the sensors against the user's forehead. Within the sensor strap 120, EEG/EOG/EMG electrodes 235 are optimally positioned to measure rapid eye movements, cortical arousals, sleep spindles, K-complexes and stage sleep. Sensors placed on the forehead may be capable of acquiring both the brain's electrical activity and eye movements. In one embodiment, the sensor strap 120 provides for at least one sensor to be placed off the forehead in a non-frontal region of the brain to improve the detection of alpha waves which are used to assess sleep onset and cortical arousals. According to an embodiment, the sensor strap 120 also provides the electrical pathway to drive the red and infrared light emitting diodes and photodiodes in the reflectance sensor 230. The reflectance sensor 230 can be used to generate signals for the calculation of oxyhemoglobin saturation and pulse rate of the user. From the reflectance sensor 230 inputs, a photoplethesmographic signal can be derived to measure respiratory effort via changes in forehead venous pressure.

In an embodiment, the number of sensors included in the sensor strap 120 is minimized and the connection between the sensors in the sensor strap 120 and the DAU 110 is a wireless connection. As a result, the sensor strap 120 can be configured for use on numerous sites, using various sensor combinations, and can be used with user's having different head sizes. In an embodiment, additional EEG sensors (e.g., electrodes) or connectors can be added to the sensor strap 120 to create the flexible interface to the electronic circuitry.

Furthermore, in some embodiments, inter-electrode spacing can be adjusted to accommodate adolescent and child head sizes. In some embodiments, headband 130 can be integrated into or affixed over the sensor strap 120 to increase ease of preparation. Rather than using individual EEG electrodes 235 and a comfort strip, the sensor strap 120 may comprise a sheet of adhesive foam in which the sensors are embedded and with conductive gel placed over the conductive sensors. The use of foam or alternative potting method ensures the light from the reflectance sensor is transmitted into the skin and not directly to the photodiode.

Figure 5:
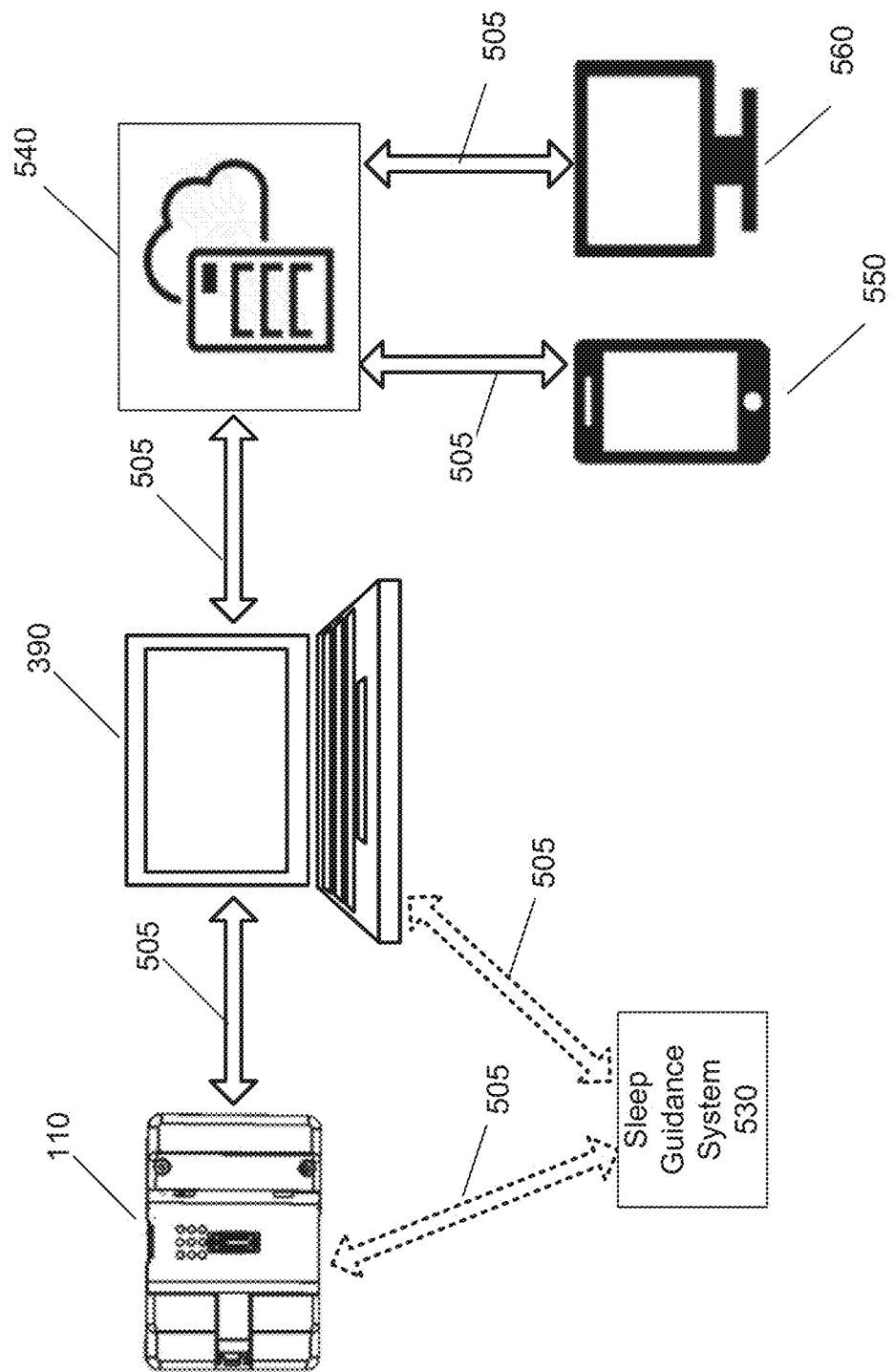

FIG. 5 schematically illustrates an integrated system for monitoring physiological signal patterns of one or more patients, in accordance with various embodiments. The integrated system of FIG. 5 comprises a DAU 110 communicatively coupled to an external computer system 390 via a communication interface 505 (e.g., a wired or wireless communication connection). The external computer system 390 may be communicatively coupled to a network and/or cloud server 540 (e.g., through a wired or wireless communication connection). FIG. 5 also illustrates mobile devices 550 and or other computer systems 560 that are coupled to and may access the cloud server 540 via a network and/or other wired or wireless communication connections. While FIG. 5 illustrates one of each of DAU 110, computers systems 390, 560, and mobile device 550, it will be appreciated that any number of DAUs may be connected to a single computer system 390 or multiple computer systems. Thus, in some embodiments, a plurality of DAUs may be communicatively coupled to one or more computer systems which may communicate patient data to the cloud server 540.

FIG. 5 illustrates remote, mobile and/or online access to patient physiological data. FIG. 5 depicts various devices for analysis, communication, and processing data from DAU 110, for example, computer systems 390, 560 and/or mobile device 550, according to various embodiments. Each of these devices may comprise one or more processors for executing instructions stored in a memory. Each device may correspond to a desktop computer, laptop computer, tablet, mobile device, or other apparatus comprising at least a processor, memory, and a display. In the illustrated embodiment, these device may comprise an acoustic microphone, a micro-controller, an audio output, a power source component (e.g., comprising a power supply and/or battery), a data transfer module (e.g., comprising a data storage medium and/or data transfer interface), wired network connection (e.g., a Ethernet port, telephone port, etc.), and/or a wireless transmitter, receiver, or transceiver (e.g., Bluetooth, Wi-Fi, ZigBee, 3G, 4G, 5G, LTE, RFID, NFC, etc.). In addition, computer system 390 may be communicatively connected to the DAU 110, cloud server 540, mobile device 550, and/or computer system 560 (e.g., via wired and/or wireless network connections) and vice versa. It should be understood that, in alternative embodiments, each device may have fewer, more, or different components, as well as a different arrangement of components.

In some embodiments, the system of FIG. 5 also may include a cloud server 540 in communication with one or more of the computer system 390, computer system 560, mobile device 550, and/or DAU 110. In some embodiments, the cloud server 540 may be part of a cloud computing architecture comprising servers (including processors for executing instructions) and data storage devices communicatively connected to mobile device (e.g., mobile device 550) and/or computers (e.g., computer systems 390 and 560) via a network (e.g., Internet, Intranet, etc.). In some embodiments, the connected device may comprise a client installed thereon for accessing and interacting with the cloud server 540. The cloud server 540 may perform steps corresponding to the analysis of the collected data and remotely store data from any one of the connected devices.

In some implementations of FIG. 5, the integrated system may provide for sharing of the patient's signal patterns. In some embodiments, sharing of the patient's signal patterns maybe done over a secure and/or private communication protocol. In an example embodiment, signals acquired with the DAU 110 can be transmitted via wired or communication interface 505 to a computer system 390 for processing and/or presentation. In various embodiments, the signals may be transferred using wireless technology (e.g., Bluetooth, Wi-Fi, LAN, etc.) to permit the DAU 110 and the computer system 390 to be physically untethered. As a result, the patient could be free to move. Wireless transmission may also provide users of the system the option to move the computer system 390, for example, outside the patient's room or about the environment, while still monitoring the signals from the DAU 110. In various embodiments, the wireless technology may permit centralized monitoring of multiple patients via multiple DAUs 110. Each of the multiple patients may be located in one or more different rooms and each may include a DAU 110 affixed to the patient. For example, the wireless transmission may permit a healthcare worker to monitor up to six patients from a central computer or site. Additionally, for example, the wireless transmission may permit a healthcare worker to monitor up to six separate rooms, each room occupied by one or more patients. In one embodiment, the computer system 390 can be affixed to a stand inside the patient's room. In one embodiment, the stand has a locking enclosure to secure the computer. While affixed to inside a first patient's room, the computer system 390 may be able to monitor additional patients located in other rooms via wireless communication. In any one of the embodiments described herein or in an alternative embodiment, the computer may be part of an integrated patient monitoring system, such as for example, a vital sign monitor or mechanical ventilator. Other monitoring systems are possible.

Various implementations of the systems described herein provide for the monitoring of physiological signals for detection of abnormal signal patterns and/or conditions (collectively referred to as "conditions") that may occur in patients. In some implementations, a patient may be in an intensive care unit (ICU) and the monitored condition may be at least in part a result of their acute status. For example, a DAU 110 may be affixed to a patient's forehead that is in the ICU and the computer system 390 may be disposed within the ICU or communicatively coupled to the DAU 110. The computer system 390 and/or other devices of FIG. 5 may receive physiological signals from the DAU to either display and/or identify single patterns. Example signal patterns and conditions are described below in connection to FIGS. 8-28. These conditions, however, may also be present in patients being admitted to the hospital or emergency room, and/or patients being nursed on the hospital floor. Thus, in various embodiments described herein, the absence and/or presence of one or more of these conditions can be useful to assist in identifying patients who could be transferred from the ICU to a stepdown unit, or identifying those in an acute state that requires increased monitoring or emergency care, e.g., typically delivered in the ICU. While certain example implementations of the systems of FIG. 5 are described within a hospital setting, it will be appreciated that the systems and methods herein are not to be limited to only these applications. The DAU 110 and/or integrated system of FIG. 5 may be implemented in any environment whereby a physiological signals of a patient may be collected and analyzed to improve sleep quality.

In some embodiments, wireless or wired acquisition, digitization and transmission of the physiological signals may reduce the likelihood of artifact contamination of neurophysiological signals. The capability to inspect EEG signals, and associate EEG with position, sound, and movement when abnormal power spectra are detected permits a user to further differentiate true neurological patterns from signal noise and/or interference. Once recognized, the impact of the interaction between a change in medication (e.g., dose amount and/or type of medication) and abnormal signal patterns can be assessed.

In various implementations, signal patterns detected by, for example, the DAU 110 may assist with recognizing the presence of conditions. The detected physiological signal patterns may be used by users (e.g., medical personnel) to improve or modify patient care. For example, in some embodiments, access to a visual display or other notification device (e.g., device outputting sound, vibrations, tactile feedback, light, etc.) of the detected signal patterns may be useful in recognizing and determining the presence of abnormal neurophysiological patterns. Users may then identify a physician and/or specialist who may be needed for consultation based, in part, on the presence of a determined abnormal pattern. For example, if abnormal neurological patterns are observed via the notifications or visual display (e.g., seizure, burst suppression, sepsis associated encephalopathy patterns, etc.), a neurologist may be consulted to recommend the type and dosage of anti-seizure mediation. As another example, alone or in combination, a pulmonologist may be consulted to help stabilize the mechanical ventilator if patterns of ventilatory distress are recognized. Either specialist may recognize patterns that suggest the need for modification to the type and dosage of a sedative. Access to the visual display of the signal patterns of the patient may assist specialists to provide guidance without necessarily having to be present at the patient's bedside or in the same building. While the embodiments herein are described in connection to a visual display, other forms of notifying a physician of the presence or absence of a condition may be used. For example, an auditory signals, tactile signals, etc. generated via a computer and/or mobile device in response to a detected abnormal signal pattern.

One non-limiting advantage of the systems and methods described herein is a capability to acquire and view physiological signal characteristics locally (e.g., in a hospital room), as well as simultaneously view the signal information remotely (e.g., by a user). In one embodiment, the DAU 110 may transmit the signals wirelessly (or over a wired connection) to a computer system 390 (or computer system 560 or mobile device 550). A user may be able to review the data signals using a graphical user interface (GUI), for example, as described in connection to FIG. 29-31 below. In another embodiment, the detected physiological signals may be simultaneously saved to the DAU 110 or external computer system 390 for subsequent download and transfer to a web-portal, where any user with authorized access can view the signals off-line from any location with internet access. This approach may be beneficial for in-depth analysis with interpretation for inclusion in the patient's medical record. This embodiment can be further enhanced with updates (e.g., periodically, intermittently, or on demand by a user) of the signals and process as the data is acquired. This may enable off line viewing of the patient's up to date or approximately current physiological information. Such embodiments may be beneficial to an expert who wishes to review data of an at-risk patient while enabling access to long periods of previously collected data, as well as accessing the current information. For one application, the expert may wish to compare the current data to a previous period of recorded data, for example, data collected while the patient is intubated and mechanically ventilated compared with data collected while extubated and not mechanically ventilated.

In another embodiment, the signals are transferred from the computer system 390 to a dedicated IP address or cloud server 540 where an expert can review an image of the collected signals streamed from the cloud server 540 to a computer system 560 or mobile device 550 in real time. In an alternative approach, software that characterizes and presents the signals locally may also be applied for remote real time viewing of the signal characterization described herewith. Either of the later two approaches will be optimal for an expert who is monitoring for epileptiform activity in real time.

When it is determined that a specialist needs to review the patient's signal patterns in accordance with the embodiments disclosed herein, such review could be conducted without the specialist having to physically interact with the computer system 390. In one embodiment, the computer system 390 may acquire and/or generate study files comprising patient data received from the DAU 110. The patient data, and signals therein, can be transferred to the cloud server 540 via a wired or wireless connection. In some embodiments the transfer may be done using Wi-Fi or other wireless communication protocol. The Wi-Fi connection may be a secure connection in some embodiments. In another embodiment, alone or in combination, the computer system 390 is connected to a local area network that provides internet access to the cloud server 540. The cloud server 540 may comprise a one or more processors coupled to a storage device, data store, or database for storing the patient data remote from the DAU 110 and/or computer system 390. The cloud server 540 may be operating over the internet or an intranet. Thus, the cloud server 540 may be a local cloud server 540 for operations within a given hospital or location.

The storage device of the cloud server 540 may store patient data that can be reviewed by personnel authorized to access the cloud. For example, access to the cloud server 540 may be restricted to physicians or caregivers employed by the hospital or any subset of persons having access to the patient. In some embodiment, access to the cloud server 540 may be done via a mobile device 550 (e.g., tablet or smart phone) or a computer system 560. For example, an authorized user may access the cloud server 540 via a cloud client installed on the mobile device 550 and/or computer system 560 by entering verified credentials (e.g., password, biometrics, etc.) that are capable of authenticating a user. In another example, the mobile device 550 and/or computer system 560 may be authorized for access to cloud server 540, in which case the user may not need to enter authorization information. Use of the mobile device 550 would be useful in certain situations, for example, where the personnel reviewing the patient data is on call and away from the patient. A detected abnormal signal pattern or condition could trigger an intervention notification that is transmitted to the on call personnel that may be received on, e.g., mobile device 550 regardless of physical location (as will be described in greater detail below in connection to FIGS. 6 and 7). Presentation of the signal patterns on a large screen, for example, as may be included with computer system 560 may be useful when the reviewer is making annotations or edits, and entering report comments. In various embodiments, the signal data from DAU 110 and/or from the computer system 390 can be transmitted to the cloud server 540 at periodic intervals (e.g., 3 or 5 minutes). This approach may provide remote replication of what the healthcare worker is viewing on the patient's computer system 390. In some embodiments, computer system 560 may be computer system 390 or a separate computer system.

In some embodiments, signals that have not been processed by the DAU 110 and/or computer system 390 can also be transferred to the cloud server 540 at the end of the monitoring session (e.g., as raw data). In some embodiments, a reviewer may then access the unprocessed signals via computer system 560 or mobile device 550 for subsequent processing and reviewing as described throughout this application. In some embodiments, alone or in combination, the cloud server 540 may include software comprising instructions that cause a processor to analyze unprocessed signals and/or reanalyze the signals for subsequent review. The cloud server 540 may also be able to apply additional algorithms, e.g., for the detection of seizure activity, prior to interpretation and editing. One non-limiting advantage of applying signal processing routines to the entire record stored on the cloud servers 540 is an ability to provide more sophisticated and complicated processing routines using additional computing resources. Whereas other implementations may process a subset of the data or process the data in real-time using limited computing resources thereby requiring less complicated algorithms to do so. While this may permit real-time monitoring, such advantage is a trade off with limited computing resources of the mobile device 550 and/or computer system 560.

Figure 6:
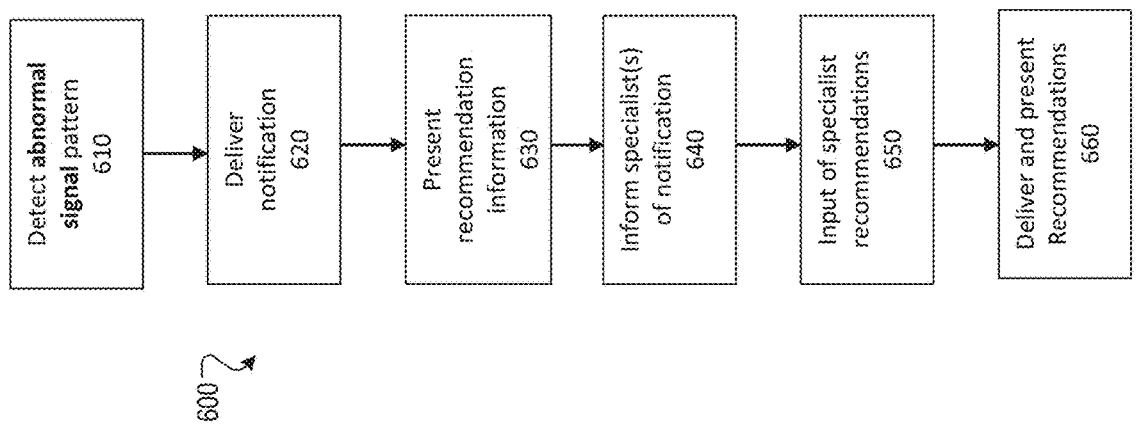
FIG. 6 illustrates a flowchart for an example process of detecting abnormal signal patterns, in accordance with various embodiments.

For example, FIG. 6 illustrates a flowchart for an example process 600 of detecting abnormal signal patterns in patients, according to an embodiment. Process 600 may be implemented by the integrated system of FIG. 5 described herein. The process 600 may be implemented to detect abnormal signal patterns or conditions as described herein for review by users and recommending for managing the patient sleep based on or in response to the detected condition.

At step 610, the process detects an abnormal signal pattern. In one embodiment, an abnormal pattern may be detected via DAU 110, for example, by a healthcare worker trained to use the computer system 390 to detect the abnormal patterns that require a specialist review. In some embodiments, automated algorithms can be employed to detect any one or more of or all of the conditions described in FIGS. 8-28 (e.g., through a comparison of power spectra waveforms representative of the physiological signals). Automated algorithms for detecting these conditions may reduce the occurrence that a user does not recognize when intervention is required and/or patient data should be reviewed by a specialist (e.g., burst suppression, sepsis associated encephalopathy, respiratory distress, etc. as described herein) for possible modification of treatment. Thus, in some embodiments, a notification (e.g., a message) or alarm may be initiated at step 620 via the DAU 110, computer system 390 or other external system. The alarm may be audible (e.g., a sound or noise indicting a detected condition), tactile feedback, visual (e.g., a light that is flashed or otherwise strobed), or a message sent via one or more of the computer systems 390 to a mobile device or other computer system (e.g., systems 550 and/or 560).

To avoid and/or minimize sounding false alarms, in some embodiments, various thresholds can be applied to each of the automated algorithm/detection rules. Each of the thresholds may be adjustable. For example, sleep is very important for the patient's recovery, thus a threshold may be based on the amount of sleep (e.g., amount of time spent sleeping). For example, an intervention notification or alarm could notify the hospital staff when the patient has had too little sleep (e.g., less than 6 hours in the previous 24 hours). The decision on whether to apply a threshold for 6, 7 or 8 hours of sleep, for example, may be dependent on the type and dose of medication being administered or other external factors. Other example thresholds may be based on the acute status or circumstance of the patient to avoid false alarms. For example, ambient noise thresholds may be based on the magnitude and duration of the ambient noise that would interrupt sleep, which may differ based on time of day and associated during circadian dips. For example, a hospital environment at one time during the day may have more ambient noise than a later time at night. An alarm would be appropriate with detection of loud sound coupled with an awake condition during the sleeping portion of the circadian rhythm. Conversely, a loud sound coupled with sleep may indicate sleep disordered breathing. In one embodiment, the sounding of an alarm could trigger a bedside review of the previously recorded study data to rule out the presence of abnormal physiological patterns (e.g., three or more consecutive minutes of abnormal slow wave activity as described below).

At step 630, recommendation information may be optionally presented for specific conditions. For example, recommendation information may be presented to a caregiver via computer system 390, mobile device 550, and/or computer system 560 for providing interventions with the patient's care. In some embodiments, the recommendation information may be stored locally on a device and/or stored in the cloud server 540 and transmitted to a device operated by the caregiver, for example, in the disease management recommendation data store described above. The recommendation information may comprise interventions designed to consolidate and/or manage sleep patterns of the patient. These interventions can be standardized and developed by, for example, key opinion leader(s), committee of hospital staff members, or consensus opinion of a professional society. In some embodiments, recommendation information may be stored and mapped with conditions, such that when a specific condition is identified the recommendation (and associated intervention) may be retrieved. Furthermore, the patient information in the patient data stored can be accessed, compared to information in the comparative data data store to identify differences between the patient in question and a health patient, and this comparison may be associated with a specific condition used to retrieve the recommendation information.

A graphical user interface installed and operated, for example, on the mobile device 550, computer system 390, and/or computer system 560 can be used by the caregiver to set or adjust alarm settings to their specifications based in part on the intervention recommendations. For example, if non-convulsive seizure activity is detected in the signal patterns, an example recommendation may be to intervene by placing the patient on anti-convulsive medications and initiate continuous EEG monitoring. Another example recommendation may also include a care giver intervening by reviewing and/or changing the type or dosage of administered medication(s) e.g., sedative.

At step 640, an optimal notification may be delivered to the designated user (e.g., specialist(s)). The presentation of the notification may be similar to the notification of step 620. For example, a notification may be automatically delivered via the computer system 390 or DAU 110 dependent on the condition detected by the DAU 110. The condition may be recognized by processing of the signals from the DAU 110 as described herein. The specialist may then use, for example, the system of FIG. 5 to review the signal data via, for example, a GUI (e.g., FIGS. 29-31) to identify and analyze the data for abnormal signal patterns.

In various embodiments, the specialist can use a mobile device 550 or computer system 560 to input confirm or other provide recommendations, instruct caregivers to intervene in accordance with the recommendations, and/or modify the recommendations (step 650). In some embodiments, the specialist may be able to instruct systems and device surrounding the patient to intervene, for example, modify a dosage and/or rate of medication supplied by an IV. Other interventions may be readily apparent in a hospital setting for remote control. Such inputs may be transmitted to the cloud server 540 for storage. Additionally, using the cloud server 540, the recommendations may be transmitted to the patient computer system 390 for presentation to the patient's healthcare worker, at step 660, and/or automated action by medical devices associated with the patient's care. One skilled in the art will recognize that these steps could be implemented in part, in total, or in any order. In some embodiments, the delivery of notifications and communication between the healthcare worker and the specialist, with respect to intervention recommendations, can be made via telephone, email, or other means of communication.

Alternatively, the integrated system of FIG. 5 may be automated, for example, by removing the need for a healthcare giver at the computer system 390. Accordingly, the systems and methods described herein may provide both diagnostic and therapeutic benefit. In some embodiments, the integrated system may be automated for example so to diagnosis patients without user intervention. For example, the DAU 110 may detect signals representative of an abnormal signal pattern processed by the computer system 390 and/or cloud server 540, e.g., such as the conditions described in FIGS. 8-28. The detected condition may trigger an intervention message sent by the computer system 390 to retrieve intervention recommendations related to the condition, as described above. In some embodiments, the computer system 390 and/or cloud server 540 may transmit a message to mobile device 550 and/or computer system 560 to notify the designated specialist or physician of the presence or absence of the condition for implementation of the recommendation. Thus, the need for a healthcare provider near the patient computer system 390 may be reduced or removed. In some embodiment, the computer 390 may select one or more recommendations, for example, by identifying, notifying, or displaying studies to a clinician that meet his/her or the hospital's designated criteria for review. Additionally or alternatively, in certain situations, the computer system 390 may, based on the patient's status, medical needs, and detected condition, retrieve and execute the recommendation without intervention by a healthcare giver or designated physician. Thus, the integrated system may be fully automated and reactive to the detected conditions in real-time.

For example, returning to FIG. 5, the integrated system may also comprise an optional sleep guidance system 530 coupled to the DAU 110 and/or computer system 390. For example, the DAU 110 (or other components of the integrated system of FIG. 5) may detect signals representative of the conditions describe herein and process the signals to trigger the above described recommendation and intervention messages. The intervention message may be transmitted directly or indirectly (e.g., from a specialist following the steps of FIG. 6) to the sleep guidance system 530. The sleep guidance system 530 can be configured to initiate a therapeutic action based on or in response to receiving the intervention message.

The sleep guidance system 530 may comprise one or more devices and/or systems for controlling peripheral equipment connected to and providing for the patient medical care (e.g., monitoring, administrating, and/or facilitating the patient's medical needs). For example, the sleep guidance system 530 may comprise a device for controlling medication provided to the patient via an IV. The device may be able to control dosage, timing, and type of medication administered to the patient. Other medical equipment and devices controlled thereby are possible.

In one example, the sleep guidance system 530 may include a stimulus generator that controls one or more peripherals for execute the therapeutic actions based on intervention recommendations (e.g., for staging sleep and/or managing the patients sleep cycle through the sleep stages). Some example peripherals include, but are not limited to, devices to generate and control light, sound, temperature, and tactile feedback based on the received signal. The DAU 110 may be communicatively coupled (e.g., via wired or wireless communication) to the sleep guidance system 530. In another embodiment, the sleep guidance system may be part of and/or embedded in a common device as the DAU 110. In some embodiments, alone or in combination with the above described embodiments, the sleep guidance system 530 may be communicatively coupled to the computer system 390, cloud server 540, computer system 560, mobile-device 550, or any combination thereof.

In various embodiments, the sleep guidance system 530 may be substantially similar to the systems and devices described in U.S. Pat. Nos. 8,628,462; 8,784,293; and 8,932,199, all of which are hereby incorporated by reference in their entirety. These patents describe systems and methods for optimization of sleep. For example, the physiological signals of a patient may be monitored to identify a current sleep state experienced by a patient, determine a desired sleep state that the patient should be experiencing based on sleep architecture data for the patient, identify sensory stimuli that may be applied to the patient to guide the patient to the desired sleep state from the current sleep state, and generate the sensory stimuli to guide the patient from the current sleep state to the desired sleep state. Such concepts may be applied to the present disclosure, for example, where guiding the patient to a desired sleep state (or away from an undesired sleep state) may be a form of therapeutic action. The sleep architecture data may be based, in part, on the methods and conditions described in connection to FIGS. 8-28. Continual monitoring of physiological signals as described herein of the patient allows the system to adapt to changes in the sleep state of the patient and to adjust the stimuli being generated based on intervention recommendations. Embodiments also provide for detection and protection of the patient from environmental disturbances, such as noise, light, and temperature changes. Thus, the patient may be guided to desired sleep states to improve recovery time and managing administration of medication.

Furthermore, the systems and methods may be implemented to achieve efficient sleep periods of a patient even where there is little sleep time available or when the sleep periods are interrupted, for example, due to ICU and/or other hectic environments, administering of medication, or aliments occurring during a sleep cycle as described herein. Thus, embodiments herein can be used to optimize the sleep cycles of a patient to allow the patient to experience more efficient sleep, to wake feeling more refreshed, to require less sleep than the patient may have required without the optimizations, and to reduce the impact of medication and improve recovery time.

In some embodiments, the sleep guidance system 530 may be a sleep mask as described in the above identified patents. Alternatively, or in addition, the sleep guidance system may be configured to control peripherals in the surrounding ambient environment in which the patient is sleeping. The peripherals may be communicatively coupled to the computer system 390, DAU 110, and/or other systems that may provide automated and/or commands for controlling such peripherals.

The sleep guidance system 530 may, for example, acquire and monitor one or more physiological signals, indicative of a sleep state of a patient (e.g., as described below step 805 and 810 of FIG. 8). According to an embodiment, the physiological signals can include, but are not limited to, electroencephalogram (EEG), electrooculogram (EOG), electromyogram (EMG), respiration, heart rate, body movement, galvanic skin reaction, blood pressure, blood flow, blood chemistry, behavioral responses, or some combination thereof.

A current sleep state of the patient can be determined using the physiological signals (e.g., as described below in step 815 of FIG. 8). According to an embodiment, the physiological signals may be processed using a set of basic signal conditioning algorithms (e.g., artifact recognition and rejection, band-pass filtering, and/or other signal conditioning algorithms). According to an embodiment, the sleep state of the patient may be determined using machine learning, pattern recognition, artificial intelligence, optical character recognition, or similar techniques to match the physiological signals obtained from the patient with one of the sleep stages as described herein.

The current sleep state information for the patient may then be added to a sleep state record associated with the patient. According to an embodiment, the sleep state record associated with the patient may be stored and include, for example, historical sleep data associated with aliments and abnormal sleep events. The sleep state record for the patient may also include a record of recent sleep information representing the sleep architecture of several most recent sleep episodes of the patient. The sleep architecture associated with the patient may be updated with the current sleep state for the patient at the end of each ongoing sleep episode.

A desired sleep state can then be determined by applying a set of rules to the current sleep information and the recent sleep information. The rules aid in optimizing the sleep performance of the patient by identifying a desired sleep state that the patient should be experiencing at a particular time, for example, as described in more detail in connection to FIGS. 8-28. A set of rules may be defined for a particular patient and/or a particular set of sleeping parameters. For example, a set of rules may be defined for a patient who is in the ICU for a given aliment, where irregular and abbreviated periods of sleep can occur due to environmental, illness, and/or medication conditions. According to an embodiment, the personalization of the rules to suit the needs of the particular sleeper can include evaluating which physiological characteristics most clearly indicate a change between the sleeper's sleep states, which patterns of physiological characteristics occur at which portions of the sleeper's sleep cycle or under which circumstances, how a sleeper's physiological characteristics or sleep patterns change when exposed to sensory stimuli and/or medication, how a sleeper's physiological characteristics respond when sleep is disrupted, optimal durations and patterns for a sleeper's sleep cycle, what sensory stimuli works most effectively to move the sleeper through the sleep stages, and/or other processes for calibrating the rules to the needs of a particular patient. For example, as described below, certain sleep states may be undesirable for certain aliments and thus one rule may be to avoid such states as undesirable and/or other states may be identified as desirable (e.g., as described below in connection to possible PTSD patients).

After the desired sleep state is determined using the rules, the desired sleep state may be compared to the current sleep state for the patient, and a determination can be made whether the current sleep state differs from the desired sleep state. If the current sleep state differs from the desired sleep state, a recommendation message may be generated and an intervention (e.g., therapeutic action) may be initiated in response thereto. For example, sensory stimuli can be generated to guide the sleep pattern of the patient toward the desired sleep state. Similarly, in some embodiments, an undesired sleep state may be determined, the sensory stimuli may be generated to guide the patient out or away from an undesired state. The sensory stimuli can be any stimuli that can be sensed by a sleeping patient. According to some embodiments, sensory stimuli may include light, sound, smell, vibration, heat or cold, moisture, electric shock, and/or other stimuli that can be sensed by a patient. As described below in connection to FIG. 7, the generated sensory stimuli may be based on a recommendation and/or intervention.

According to an embodiment, adjustments can be made to the sensory stimuli to lead the sleeping patient toward another sleep stage. These changes can include adjustments in the magnitude or quantity, tone, quality, pattern, frequency, application location, or any other adjustment to sensory stimuli. Even minute changes to sensory stimuli may be sufficient to lead the sleeping patient toward another sleep stage. The type, duration, intensity, and timing of generated stimuli depend on the current and desired sleep state and on whether a direct transition is physiologically possible or whether the sleeper needs to be led through some intermediate sleep state(s) prior to reaching the desired state. For example, if the sleeper is awake while the desired state is NREM Stage 2 sleep, soothing sounds may be generated to induce a transition from wakefulness through NREM Stage 1 sleep to NREM Stage 2. If for an example the sleeper is in NREM Stage 3 sleep while the desired state is NREM Stage 2 sleep, a combination of subliminal sounds and stroboscopic light flashes may be optimal. Continued monitoring of the physiological attributes of the patient can be used to determine whether the intended transition from one stage to sleep to another has taken place.

Accordingly to an embodiment, alone or in combination, adjustments can be made to the patient's medical care. These adjustments may include changes to medication dosage, medication type, rate of administration of dosage, and the like. The adjustments may be based on the ailment suffered by the patient, the environment of care (e.g., ambient light, sound, etc.), abnormal signal patterns identified by the system and/or experts, acute status of the patient, and the like.

According to some embodiments, if the current sleep state does not differ from the desired sleep state, then no stimuli (or therapeutic action/adjustment) may be generated to guide the sleep pattern of the patient, because the patient is already in an optimal sleep stage. According to other embodiments, if the current sleep state of the patient matches the desired sleep state, one or more stimuli may be generated to help maintain the current sleep state of the patient. For example, in a loud environment, a white noise may be maintained to keep the patient in a desired sleep state. Similarly, a light may be maintained in environments that have variance in ambient lighting.

Disturbances that may interrupt or negatively impact the sleep state of the patient may be identified, and a determination can be made as to whether any disruptive disturbances are present. Disturbances may include loud noise, strong light, temperature of the sleeping environment, and/or any other potential distracters which may cause the patient to wake up frequently or prematurely or prevent the patient from spontaneously entering into deeper stages of sleep (e.g., as is likely in a hospital or ICU environment). If disruptive disturbances are present and identified, the patient may be protected from the disturbances by taking or initiating remedial actions. For example, if too much ambient light is present in the environment, the sleep guidance system may be configured to control the lights in the sleeping environment so to be dimmed or the blinds closed to block sunlight or other light from outdoors from entering the room, or an eye mask or set of tinted glasses may be provided to block ambient light from reaching the patient's eyes. If the temperature of the room is too hot or too cold, a heating and ventilation system for the sleeping environment can be adjusted to adjust the temperature of the room to a more optimal sleeping temperature. If too much noise is present, a set of noise canceling headphones or earplugs may be provided, or white noise may be generated to block out the noise. If no disturbances are identified or the patient has been protected from the disturbances, the method returns to the monitoring step.

Figure 7:
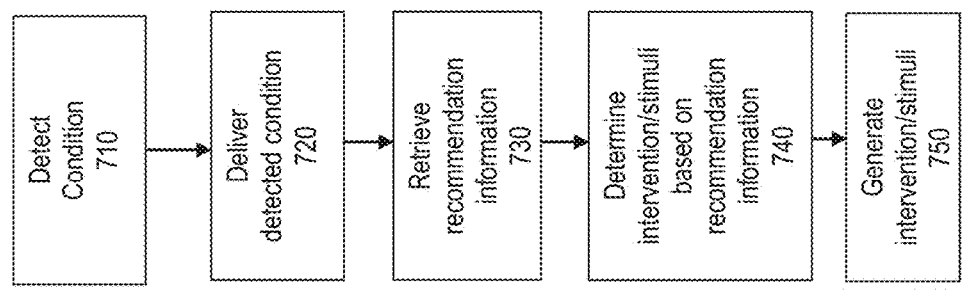
FIG. 7 illustrates a flowchart for an example process for diagnosis and therapeutic treatment of patients in accordance with various embodiments.

FIG. 7 illustrates a flowchart for an example process 700 for diagnosis and therapeutic treatment of patients in accordance with the embodiments described herein. Process 700 may be implemented by the integrated system of FIG. 5 described herein. The process 700 may be implemented to detect abnormal signal patterns or conditions in the patient's physiological signals as described herein and utilize a sleep guidance system to implement intervention recommendations (e.g., generate one or more stimuli to guide the patient's sleep) without the need for intervention by a user (e.g., medical personnel).

At step 710, an abnormal signal pattern or condition may be detected. For example, the DAU 110 may acquire physiological signals from a patient coupled thereto. The DAU 110 may then characterize the signals to detect a condition indicative of needing an intervention and/or transmit the acquired signals to computer system 390 or other computer systems for processing and detection. Such conditions may include, but are not limited to, the example conditions described below and in connection to FIGS. 8-28 (e.g., through a comparison of power spectra waveforms representative of the physiological signals). As described above, thresholds may be applied to the condition detection rules to avoid and/or minimize false detections. At step 720, the detected condition may be delivered to one or more components of the integrated system of FIG. 5 as a message, as described above. In some embodiments, the physiological signals may be transmitted as part of the notification message. The message may be delivered to the cloud server 540 or other devices of system for storage and additional processing. In some embodiments, the signals may be delivered or transmitted to the sleep guidance system 530 and processed thereon. The condition may be recognized by processing of the signals as described herein.

At step 730, recommendation information may be retrieved. As described above, the recommendation information may be based on at least one of a detected condition, the patient's medical history or current health concern, environmental surroundings (e.g., hospital environment, ICU, etc.), current and/or historical sleep stages, and/or other rules to improve sleep management. The recommendation information may be pre-determined and stored in the memory 324 of the DAU 110. In other embodiments, the recommendation information may be stored in the cloud server 540, the computer system 390, the computer system 560, the mobile-device 550, and/or a data storage accessible to the sleep guidance system 530. The recommendation information comprise one or more interventions for adjusting the patients case, for example, one or more stimuli and/or therapeutic action as described above.

At step 740, one or more intervention for application to the patient may be determined based on the recommendation information. In various embodiments, the intervention may be a stimuli or other therapeutic action determined by the sleep guidance system 530 for managing sleep quality and circadian rhythms as described herein. In some embodiments, the intervention may be determined by and controlled by the integrated system of FIG. 5. The intervention may include one or more of, but not to be limited to, tactile vibrations (e.g., vibrotactile), audible (e.g., sounds, music, etc.), visual (modifying ambient light such as adding blue light), changes in temperature (e.g., adding heat or applying a cooling sensation) to the patient, adjustments to medication administrated (e.g., increase/decrease dosage, administer different medications, increase/decrease rate of medication), adjustments to patient monitor peripherals, and the like.

At step 750, the sleep guidance system 530 may generate and/or other control medical equipment based on the determined one or more interventions to manage the sleep quality of the patient. For example, if non-convulsive seizure activity is detected in the signal patterns, a standard response may be to reduce the level of sedation, prescribe an anti-convulsive medication, and begin monitoring the EEG with a full 10-20 montage.

In other embodiments, an intervention may include generation or modification of stimuli to lead the patient toward a desired sleep state or away from an undesired sleep stage. For example, if irregular sleeping patterns are detected (e.g., insomnia and/or circadian rhythm disorder) in the signal patterns, one or more of the stimuli may be adjusted to lead the patient away from an awake state or toward a desired sleep stage. For example, if the patient is awake while the desired state is NREM sleep, soothing sounds, changes in heat or cold applied to the facial area, or light can be used to induce a transition from wakefulness to NREM. Continued monitoring of the physiological state of the patient can be used to determine whether the intended transition from one stage to sleep to another has taken place so to treat insomnia and other sleeping disorders.

In another example, the systems and methods described herein may be configured to stage sleep in real-time in combination with delivery of one or more stimuli to suppress an undesired sleep state. In some embodiments, such staging may be used to trigger an intervention recommendation for a disease state or abnormal condition. In some embodiments, detection of REM sleep and/or transitioning toward REM sleep may trigger the intervention notification.

For example, if the patient is in currently in REM, at step 740 and 750, one or more stimuli may be determined and generated so as to lead the patient out of REM and into NREM. If the patient is in NREM, at step 740 and 750, the one or more stimuli may be generated so to maintain NREM. For example, the one or more stimuli may include delivery of vibrotactile and/or blue light to suppress REM sleep.

In one embodiment, the applied intervention may be adaptive to the individual to deliver the least amount of intervention needed to shift the user from REM to non-REM sleep. For example, if the user does not respond to a stimuli based intervention within a minimum time duration (e.g., 1 min) the delivered stimuli may be adapted (i.e., frequency, intensity and/or duration increases). In various embodiments a REM avoidance intervention may enables the user to shift sleep stages without entering an awakened state. In other embodiments the intervention may cause the user to awaken as a means to avoid REM sleep. One skilled in the art will recognize that numerous approaches could be applied to shift a patient from REM to non-REM sleep while avoiding an awakening state including by modifying or adjusting a frequency, intensity and/or duration of the applied one or more stimuli. While the foregoing examples are described in connection with the sleep guidance system 530 and the integrated system of FIG. 5, it will be appreciated that the describe interventions and/or rules for leading the patient's sleep stage can be performed by an identified specialist and/or caregiver as described above in connection to FIG. 5. Furthermore, in some embodiments, the specialist and/or caregiver may optionally intervene with the automated process of FIG. 7, for example, by receiving the recommendation information and instructing the systems to apply the intervention remotely and/or modifying the intervention in accordance with improving patient care for special cases that may not be covered in standard rules.

Figure 8:
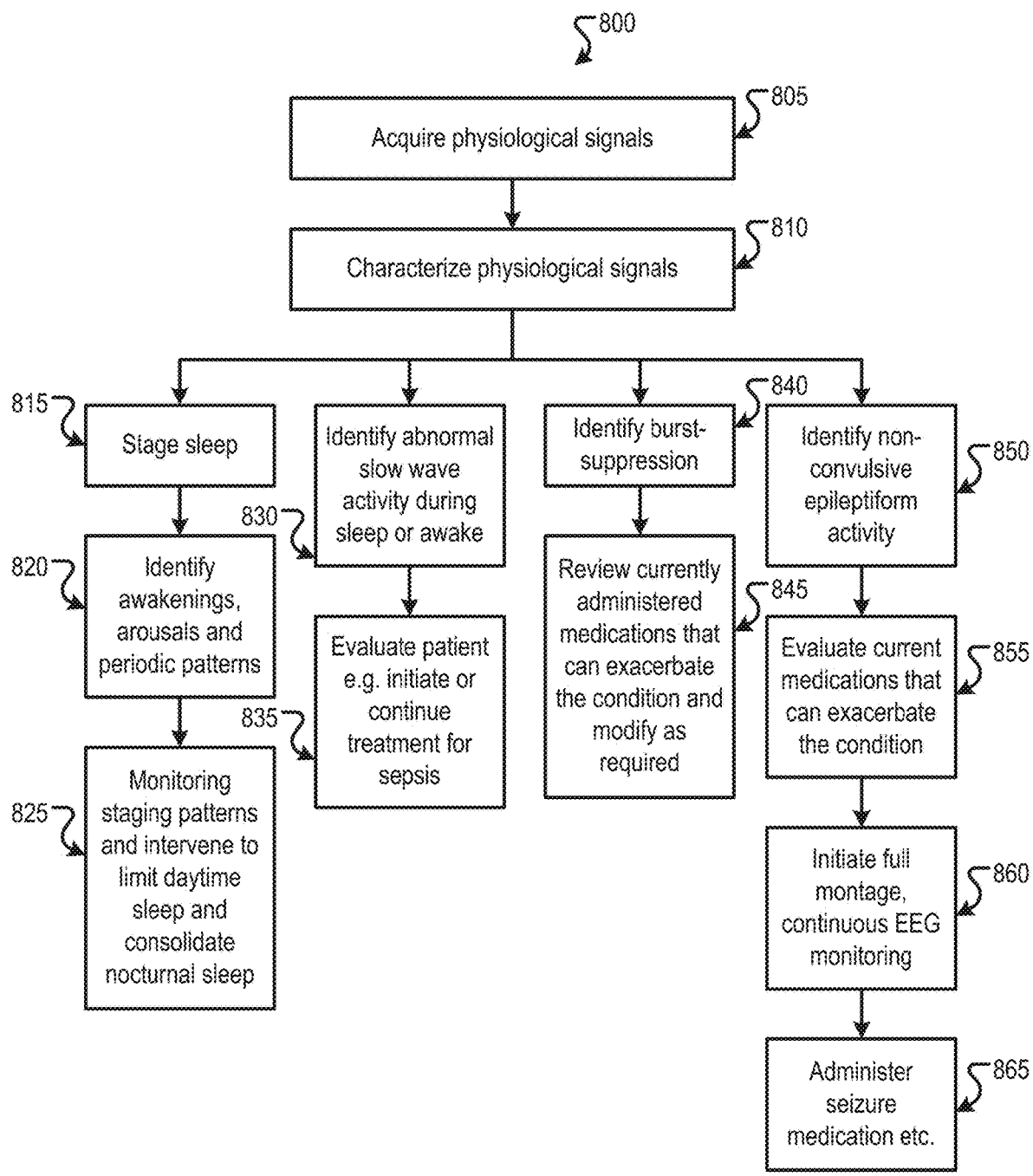
FIG. 8 is a flow chart of a method for monitoring physiological signals to speed recovery and improve outcomes, in accordance with embodiments herein.

FIG. 8 is a flow diagram of a process 800 for monitoring physiological signals according to embodiments herein. The process 800 may be used to monitor physiological signals from a patient to asses sleep quality of a patient. In some embodiments, process 800 may be implemented to detect and/or otherwise characterize the etiology of sleep quality of a patient. The process 200 may be used in coordination with providing medical services (e.g., treatment, medication, etc.) to increase recovery time of a patient and/or improve outcomes of medical treatment (e.g., increase in probability of successful treatment and/or improved results of treatment). For example, without subscribing to a particular scientific theory, it is believed that improved sleep quality and management may be advantageous in recover over aliments and injuries. A patient may be more likely to recover quicker if they are able to achieve necessary sleep quality (e.g., proper circadian rhythm and/or consolidating sleep to nocturnal hours). For example, process 200 may allow staff with limited neurophysiological training or expertise to detect abnormal patterns which slow patient recovery and/or increase mortality. FIG. 8 may be implemented using the various systems described above in FIGS. 1-5.

The process 800 begins at step 805 with the acquisition of physiological signals from a patient by a DAU (e.g., DAU 110). As described above, the DAU performs concurrent measurements of two categories of signal data: (1) signal data related to sleep states, and (2) signal data related to the type of sleep disruption. In an embodiment, the apparatus used to acquire the physiological signals ideally uses electrodes and sensors, such as sensor strap 120, that can be self-applied with limited skin or scalp preparation, and which monitors signal quality during use and provides user feedback when signal quality problems are detected. The collected physiological signals may include rhythmic activity as well as transients. In some embodiments, the physiological signals include any one or more of alpha signals, sigma signals, beta signals, delta signals, theta signals, EMG signals, EEG signals, and EOG signals. Additionally, the physiological signals made include or be provided with acoustic signal data and movement signal data. Each physiological signal may be representative of a frequency band, as described above, and represented by a power spectra waveform as described above and illustrated herein.

Once the physiological signals are obtained, these signals are characterized (step 810) for additional process steps to carried out in various implementations. In some embodiments, characterizing the physiological signals may comprise or otherwise be part of characterizing an etiology of sleep of the patient associated with the DAU 110. Characterization herein may include, for example, a comparison amongst the physiological signals acquired. For example, the power spectra waveform of a first physiological signal may be compared with one or more other power spectra waveforms of the physiological signals to characterize and identify disruptions to sleep quality. As described herein, these comparisons may be used by the systems (e.g., as illustrated in FIG. 5) and/or caregivers to manage a patient's sleep. Comparison of the power spectra waveforms of the various physiological signal data may be beneficial in detecting conditions that are external to the patient (e.g., due to the environment in which the patient is located, treatment plans, medicine administered, etc.) as well as for identification of sleep arousals and/or disruptions due to sleep disorders. Conventional systems that do not utilize the power spectra waveforms as described herein may not be capable of identifying such conditions.

For example, in one embodiment, the process 800 stages the patient's sleep at step 815 (e.g., FIG. 12); identifies awakenings, arousals and periodic patterns at step 820 (e.g., FIG. 13); and then monitors staging patterns and intervenes to limit daytime sleep and consolidate nocturnal sleep at step 825 (e.g., FIGS. 5, 7, 29 and 30). In another embodiment, alone or in combination, the process 800 identifies abnormal slow wave activity (ASWA) during sleep and/or awake at step 830 (e.g., FIG. 15) and evaluates patient (e.g., initiate or continues treatment) for sepsis at step 835 (e.g., FIGS. 6 and 7). In another embodiment, alone or in combination, the process 800 identifies burst-suppression at step 840 (e.g., FIGS. 21A-23B) and reviews currently administered medication that can exacerbate the condition and modify as required at step 845 (e.g., interventions of FIGS. 6 and 7). In another embodiment, alone or in combination, the process 800 identifies non-convulsive epileptiform activity at step 850 (e.g., FIGS. 24A-24C); evaluates current medications that can exacerbate the condition at step 855; initiates a full montage, continuous EEG monitor at step 860 (e.g., as an intervention of FIGS. 6 and 7); and administers anti-seizure medication at step 865 (e.g., as an intervention described in FIGS. 6 and 7). As described above, according to some embodiments, the acquired physiological signal data can be downloaded to an external computer system 390 for processing or, in some embodiments, by firmware included on DAU 110. Alternatively, or in combination, the data may be displayed by the external computer system 390 for visual inspection and identification by users.

In an embodiment, various automated algorithms can be applied to capture signal data. For example, the EEG signals may be subjected to a filter bank that decomposes the signals into the frequency bands commonly used in the EEG analyses: eye movements/artifacts (<1 Hz), delta (1-3 Hz), theta (4-7 Hz), alpha (8-12 Hz), sigma (12-16 Hz), beta (18-30 Hz), EMG/artifacts (>32 Hz). These power bands can be used to characterize sleep architecture and sleep continuity, as well as for visual and/or automated inspection of the relevant patterns. The frequency cutoffs for these power bands can be modified as needed to characterize sleep and wake. For example, further sub-characterization of the frequency bands/bins, and or sub-analysis of the signals above 40 Hz can be employed for this purpose. Those skilled in the art will recognize that any other frequency band can also be used where advantageous. Those skilled in the art will also recognize that the filter bank can be realized with FIR filters, IIR filters, wavelets, or any other similar technique for time-frequency decomposition of signals.

In one embodiment, once the physiological signals are acquired from the sensors, the signals may be analyzed to characterize the signals (step 810) and stage the sleep of the patient (step 820). For example, average power spectra analysis computed across stage N1, N2, N3 (SWS) and REM states in the delta, theta and alpha ranges can be used to identify abnormal characteristics associated with abnormal sleep characteristics. In at least one embodiment, the power spectra may be extracted from the frequency bands described above. In some embodiments, the extracted signal power spectra may be averaged into periodic epochs (e.g., (e.g., 30 seconds) for staging sleep. While 30 second epochs are described herein, these are merely illustrative and other periodic epochs may be utilized as necessary for a desired sensitivity and analysis range. Both the absolute and relative power between and cross bands may be used to extract useful information that accommodates between differences in the relative power of the signals detected from the patient. For feature extraction, power spectra values can be extracted at any resolution, for example a resolution greater than 16 Hz. In at least one embodiment, the power spectra are presented and/or processed to enable recognition of pattern changes associated with sleep and wake or abnormal neurological patterns. While the power spectra values may be collected at any frequency. In one embodiment, the spectra power values may presented and/or analyzed at a frequency based on matching the frequency to the pixel resolution of display (e.g., 1 hz).

Figures 9A, 9B, 9C:
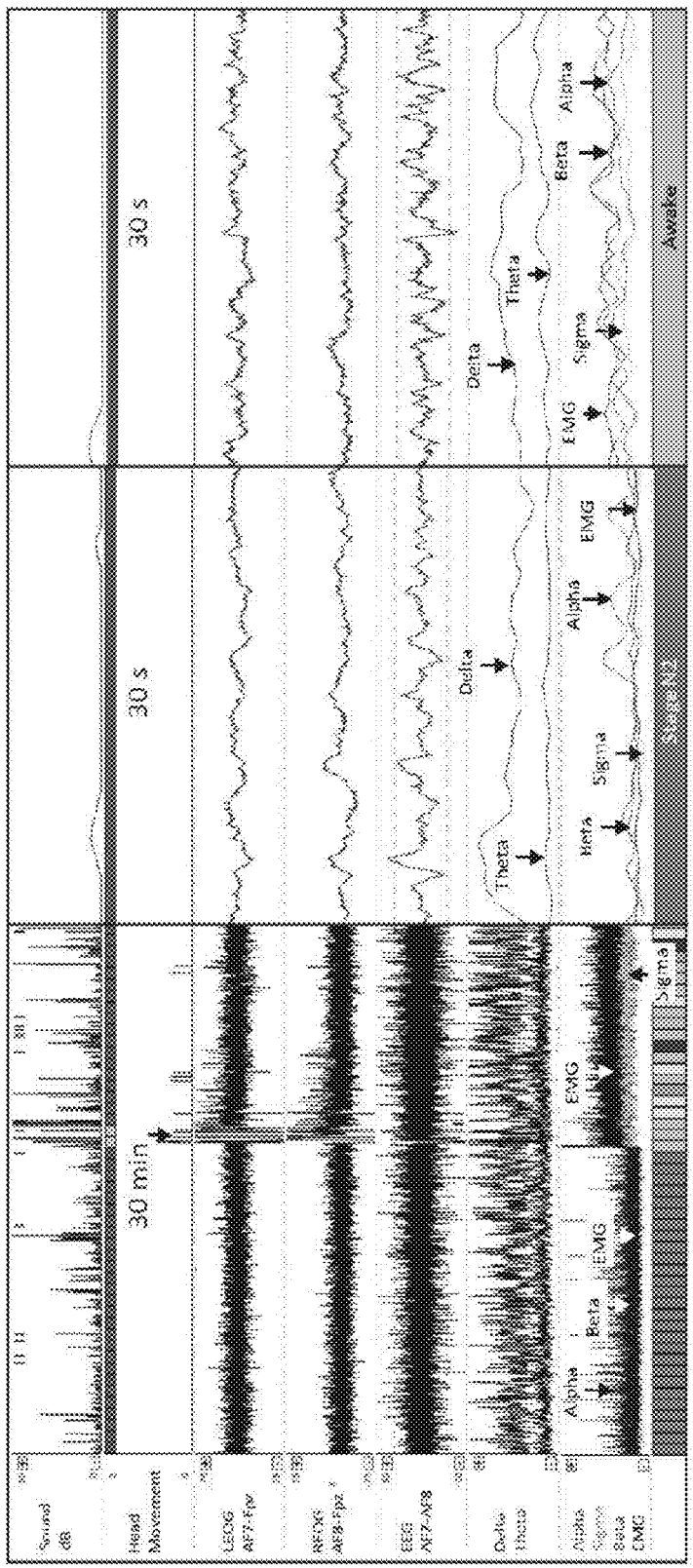

For example, FIGS. 9A-9C are an example of data illustrating acquired and characterized single patterns according to embodiments herein. FIG. 9A illustrates a 30 minute data acquisition of the plurality of frequency bands, while FIGS. 9B and 9C illustrate example 30 second epochs characterized as stage N2 and awake, respectively. Additionally, FIGS. 9A-9C illustrate a subtle decrease in frontal tone that may occur during sleep only, which can be difficult to detect visually in the EEG waveform. However, when the EMG power is lower than alpha, sigma, and beta waveforms, as shown in FIGS. 9A and 9B, the user is typically asleep. In some embodiments, the prominence and similarity of the EEG delta and theta waves in FIGS. 9Ba and 9C, even though the EMG power increased by, for example, six-fold, may suggest a high likelihood of visual misinterpretation of a sleep stage (e.g., as described below in connection to FIG. 12) of the patient without access to the relative power of all of the bands. In standard sleep stage, the number of awakenings (i.e., transitions between sleep, wake, and a return to sleep) may range from 2 to 5 occurrences per hour.

Figures 10A, 10B, 10C:
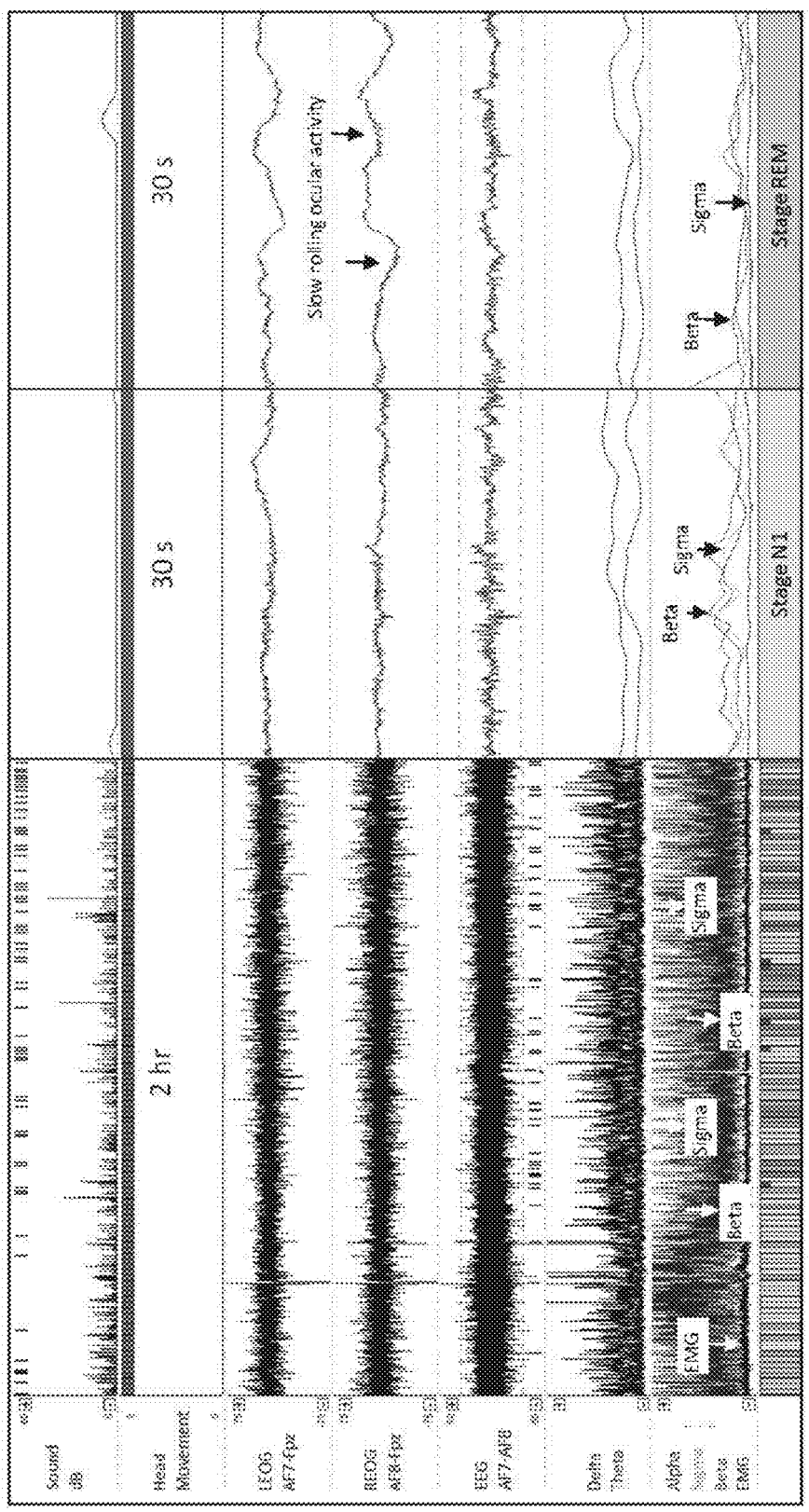

In some embodiments, identifying the patient sleep stage may be based a comparison of relative power spectra of one or more frequency bands. For example, where the EMG power is low, the magnitude of the beta power may indicate the user is in either Stage N1 or rapid eye movement (REM) sleep, for example, as shown in FIGS. 10A-10C. As another example, during REM (in patients not on medication), the sigma power may be typically lower relative to beta and alpha, as shown in FIG. 10C. During stage N1, the sigma power may typically be the approximately same in magnitude as the beta power, as shown in FIG. 10B. In some embodiments, to reduce the likelihood of a sleep stage misclassification resulting from medications (i.e., Stage N1 misclassified as REM), low rolling ocular activity as shown in FIG. 10C may be distinguished from a more sharp edged phasic ocular activity which occurs only during REM. Thus, various embodiments may characterize one or more of the plurality of physiological signals to minimize misclassification of sleep stages. Accordingly, FIGS. 10A-10C may include example signal patters of low voltage EEG compared with elevated beta power that may require modification to staging rules to avoid and/or minimize misclassification of staging rules as a result of medication(s) (e.g., FIG. 12 below).

Figures 11A, 11B, 11C:
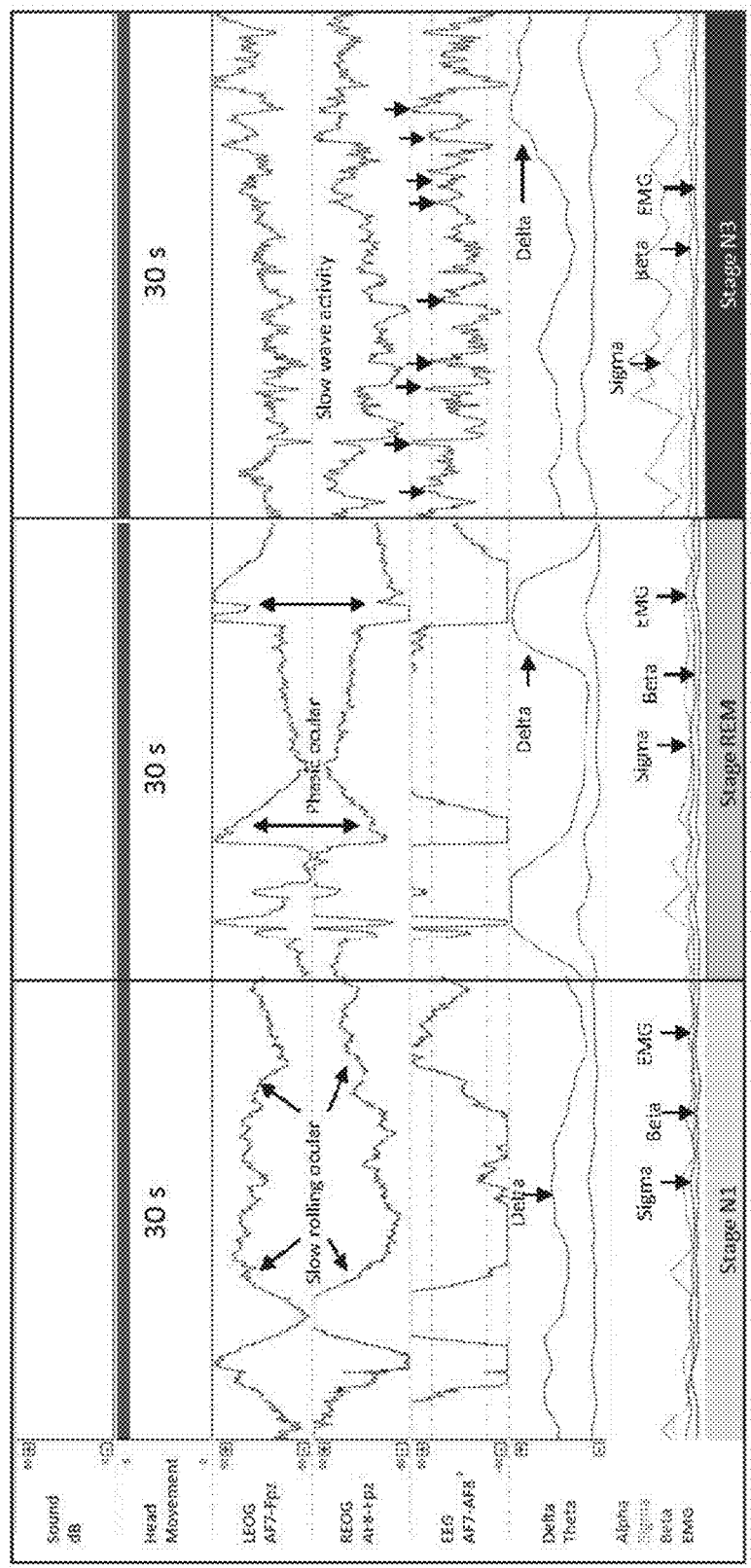

FIGS. 11A-11C provide example data of EEG waveforms that may impact delta power relative to one or more of the other frequency bands. Particularly, FIGS. 11A-11C may be at least on example of ocular and EEG waveforms having an impact on delta power relative to other frequencies. For example, delta power is illustrated relative to the theta, alpha, sigma, beta and EMG bands in a healthy adult during slow rolling ocular activity (stage N1, e.g., FIG. 11A), rapid eye movement sleep (stage REM, e.g., FIG. 11B), and slow wave sleep (stage N3, e.g., FIG. 11C). Delta power may be influenced by the negatively correlated ocular activity at sleep onset (stage N1) and during REM. Delta waves during slow wave sleep may be more asynchronous. In at least one embodiment, filters, as described above, may be applied to extract the delta power before and after removal of ocular activity. The detection of ocular activity can be achieved by comparing the phase of the signals containing left and right ocular activity. For example, the signals may be negatively correlated during both slow roller ocular activity (e.g., associated with sleep onset) and phasic ocular activity (e.g., REM). However, the magnitude and variability of the negative association may be much greater during REM, as shown in FIG. 11B. FIG. 11C illustrates that a slow roller or slow wave ocular activity and most other artifacts can be removed from the delta power via filtering, for example, a sharp filter at 1 Hz or less. In another embodiment, alone or in combination, changes in the median power of the delta activity can be used to detect sharp edges in the signal associated with ocular activity but not healthy slow wave sleep. Once this sharp edged ocular activity is detected, it can be used to decontaminate the delta power. True slow wave brain activity can be detected when the magnitude of delta power is sufficiently large and the differences in delta power before and after decontamination of ocular activity are minimal.

In some embodiments, the delta power may be interpreted relative to other EEG power characteristics. For example, since the magnitude of delta power can be influenced by both ocular (e.g., FIGS. 11A and 11B) and EEG activity (e.g., FIG. 11C), delta power may also need be interpreted relative to the other EEG power characteristics. During both stage N1 and REM the delta power can be interpreted relative to decreased theta and sigma power, and increased beta and EMG power (e.g., FIGS. 11A and 11B). During slow wave sleep (SWS) (e.g., FIG. 11C), sigma power may be more prominent as compared to beta and EMG power.

In certain implementations, when a hospitalized patient is administered a medication (e.g., sedative, analgesic, etc.) to manage agitation, pain, or other ICU condition or induce sleep, EEG power spectral characteristics used to stage sleep (e.g., step 820) may be influenced by the type and amount of medication. Medications typically administered in the ICU distort the relative power in the alpha, sigma, beta, and EMG bands, and suppress sleep spindle and slow wave activity which occurs in normal, healthy sleep. Epochs that are staged N2 with a combination of relatively low sigma power and/or increase alpha power can be indicative of a medication/sedation effect (e.g., the left half of FIG. 9A and/or FIG. 9B). Sedative-induced sleep may increase beta activity which can result in the misclassification of REM sleep. Additionally, critically ill patients can have abnormal EEG patterns which can contribute to incorrect sleep staging. Thus, embodiments herein may be configured to modify sleep staging rules based on abnormal signal patters due, in part, to administered medication.

Figure 12:
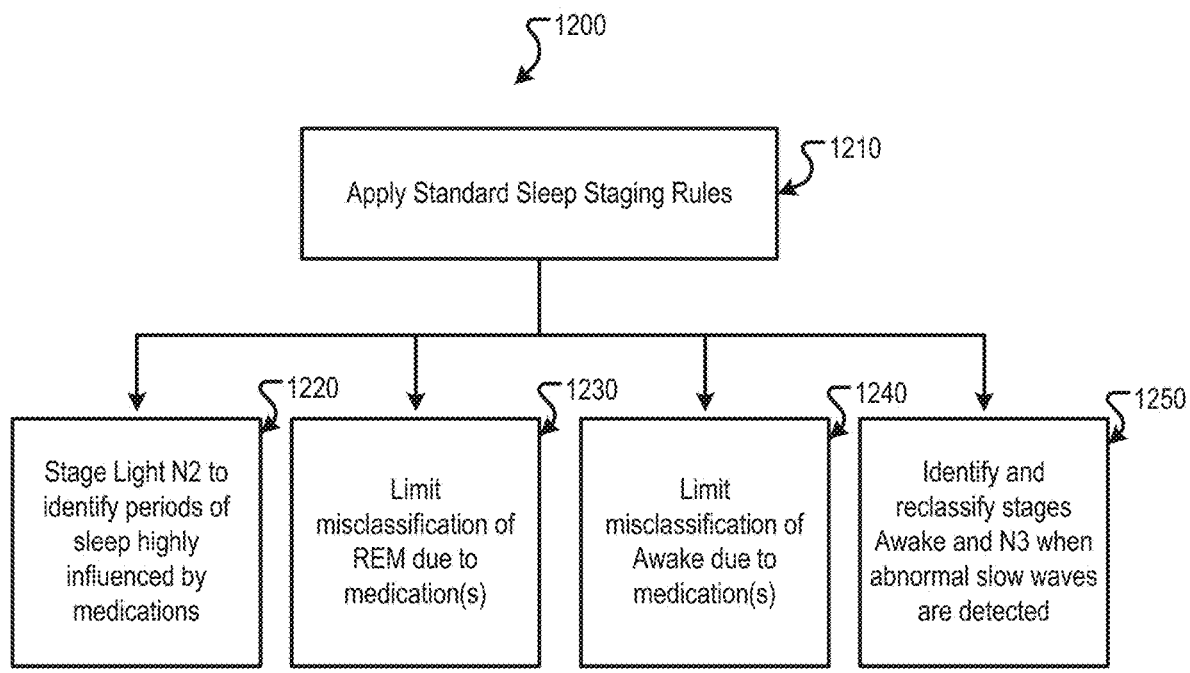
FIG. 12 is a flow chart of a method for modifying standard sleep staging rules, in accordance with embodiments herein.
Figure 13:
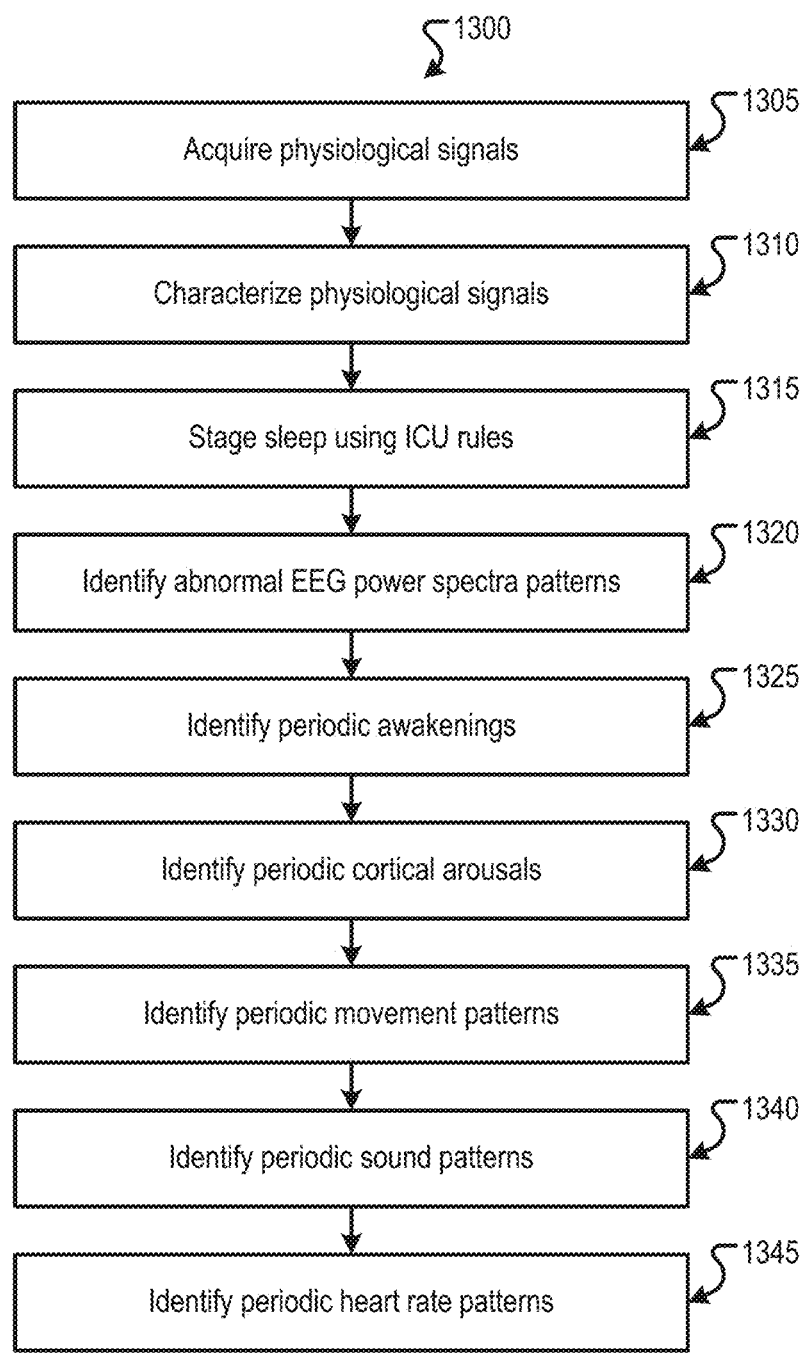
FIG. 13 is a flow chart of a method for monitoring physiological signal patterns to identify signal patterns resulting in poor quality sleep, in accordance with embodiments herein.

For example, FIG. 12 provides a flowchart of an example process 1200 for modifying standard sleep staging rules according to embodiments herein. For example, FIG. 12 may be implemented following step 810 of FIG. 8 (e.g., as part of step 820) or as a separate process. FIG. 13 may be implemented using the various systems described above in FIGS. 1-5. In some embodiments, the modification of sleep staging rules may be based, in part, on a hospitalized condition of a patient and/or medicated condition.

The process 1200 begins at step 1210 begins with automated analysis to define sleep by standard staging rules. For example, in some embodiments, once the physiological signals are obtained from the sensors, the signals may be analyzed to assess the sleep stage of the user (step 1210). As described above, according to some embodiments, the acquired physiological signal data can be downloaded to an external computer system 390 for processing or, in some embodiments, by firmware included on DAU 110. Alternatively, or in combination, the data may be displayed by the external computer system 390 for visual inspection and identification by users. According to an embodiment, the physiological signals acquired by the DAU 110 can be downloaded to external computer system 390 and stored in a memory.

In an embodiment, various automated algorithms can be applied to the captured signal data. For example, the EEG signals are subjected to a filter bank that decomposes the signals into the frequency bands commonly used in the EEG analyses: eye movements/artifacts (<1 Hz), delta (1-3 Hz), theta (4-7 Hz), alpha (8-12 Hz), sigma (12-16 Hz), beta (18-30 Hz), EMG/artifacts (>32 Hz). Those skilled in the art will recognize that any other frequency band can also be used where advantageous. Those skilled in the art will also recognize that the filter bank can be realized with FIR filters, IIR filters, wavelets, or any other similar technique for time-frequency decomposition of signals.

In some embodiments, REM sleep can be distinguished from non-REM sleep on the basis of ratios between beta EEG power (e.g., 18 to 32 Hz) and delta power (e.g., 1 to 3 Hz) within a pre-defined time window, or on the basis of a measure of agreement between the 2 EEG signals acquired simultaneously. The measures of agreement, when calculated over a short time window (e.g. 2-5 seconds) will behave markedly differently in case of eye movements than in case of delta waves (which can easily be confused with each other if only frequency analyses are used). According other embodiments, any statistical measure of agreement, such as Pearson's correlation coefficient or coherence, can be used for this purpose. Ratios of delta (e.g., 1 to 3.5 Hz) to beta (18-32 Hz) and theta (4-7 Hz) power are used to identify slow wave sleep.

In alternative embodiments, alone or in combination, the detection of sleep stages can be performed using more sophisticated linear or non-linear mathematical models (e.g., discriminant function, neural network, etc.) with variables that can be obtained from the EEG, EOG and ECG signals. Short duration fast-frequency EEG bursts are measured using one-second measures of power spectra to detect sleep spindles (that only appear during Stage 2 sleep) and EEG arousals (that appear in Stage 1 sleep). The distinction between the spindles and arousals can be made on the basis of their duration (spindles are shorter, arousals longer than 3 seconds). One skilled in the art will recognize that in addition to the techniques mentioned above, ratios of the power in various frequency bands, or linear combinations (weighted sums) of the power in various frequency bands can be used for separation of sleep states and waveforms. In addition to power spectra analysis of the EEG, one skilled in the art will recognize that variability in the ECG signal increases during rapid eye movement sleep. These patterns are different from the rapid bradycardia-tachycardia changes that occur as a result of an arousal or with the sinus arrhythmia that can be seen in children. In an embodiment, full-disclosure recording are optionally presented to allow the signals and automated sleep staging to be manually viewed and edited using a user interface provided by the data processing and visualization module of the external computer system 390. Standard sleep architecture parameters are then computed, including total sleep, REM and SWS times, sleep, REM and SWS latency, and sleep efficiency. Mean power spectra analysis computed across stage N1, N2, N3 (SWS) and REM states in the delta, theta and alpha ranges can be used to identify abnormal characteristics associated with abnormal sleep characteristics.

At step 1220, process 1200 stages Light N2 sleep to identify periods of sleep that are influenced by medications. Once these periods of sleep are identified, the process 1200 applies thresholds, describe below, to limit misclassification of REM (step 1230) and misclassification of awake (step 1240) due to medications. The process 1200 may then identify stages misclassified as awake and/or N3 and reclassify these stages as needed at step 1240, when abnormal slow wave activity (ASWA) is detected in the characterized physiological signals.

For example, process 1200 may be used to identify periods of sleeps that may be influenced by medication or external conditions (e.g., hospitalization). For example, a caregiver may determine when the medications are influencing the sleep/wake condition of a patient based on the reported sleep stage under conventional staging rules. Such medications can cause steady, elevated alpha power, that result in occasional cortical arousal(s) which may trigger an interruption in stage N2 toward stage N1 or awake. These cortical arousal(s) may not be easily detected. A medication effect that contributes to a steady elevation of either alpha or sigma activity can also reduce the capability to automatically detect alpha/sigma bursts associated with sleep spindle activity, which is a characteristic of healthy sleep. As a result, a trigger used to transition from stage N1 to N2 may be difficult to detect. Thus, classification of stages N1 and N2 may become more dependent on relative theta power, rather than use of arousals and sleep spindle events to trigger stage changes. As a result, long periods (e.g., >1 hour) of steady stage N2 in the absence of occasional awakenings, for example, may be an indication that medication levels can be reduced. In some embodiments, alone or in combination, medication effects can be further characterized by the classification of lighter stage N2 (e.g., Light N2) defined by elevated alpha or EMG activity in the absence of sleep spindle activity. Long periods of light N2 may indicate use of a medication that is disrupting healthy sleep. An abnormal neurological EEG pattern, called burst suppression (described below in connection to FIGS. 21A-23B), can be recognized by inspection of the EEG associated with long uninterrupted periods of stage N2 or Light N2. Such inspection may be done visually by a user and/or automated using one or more of the systems described herein.

In various implementations, identifying abnormal signal patterns based on sleep stage may be based, in part, on the influence of medications to avoid misclassification. Thus, algorithms used to stage sleep may be modified accordingly. As described above, FIGS. 10A-10C show an example low voltage EEG. The examples shown in FIG. 10A-10C also depict medication induced elevated beta power relative to the alpha and theta power, coupled with increased delta power resulting from slow fluctuations (e.g., less than 0.5 Hz), which may be used to avoid and/or minimize misclassification of stage REM. In other instances, medication could elevate the alpha power relative to theta and sigma power, also resulting in a staging misclassification. Such situations may also be identified in step 1220.

Medications can also increase the magnitude of power in the EMG band, providing another example of step 1220. This may result in epochs that may be visually staged as sleep, being classified by an automated means as awake.

FIGS. 9A-9C provide such an example. FIG. 9A depicts signal patterns collected on a 30 minute time scale and the EMG power increases inexplicably and remains high and steady throughout the remainder of the data collection. Whereas, on a 30 second time scale, the EEG signals look markedly similar despite the magnitude difference in EMG power used to assign the epoch as stage N2 vs. awake.

In one embodiment, the systems herein may identify a stage of awake and/or stage N3 when the patient is actually in another stage. Thus, based on detecting abnormal slow waves, the process 1200 may reclassify the stages as N2. Additionally, in the various embodiments, thresholds may be employed to account for influence due to medications. For example, thresholds used to stage sleep may be adjusted to accommodate the influence of medications to maintain the accuracy of the sleep/wake staging. In some embodiments, thresholds used ensure medications do not contribute to the misclassification of REM (e.g., step 1230) include, but are not limited to, the ratio between alpha/beta power, alpha/sigma power, theta/beta power, theta/EMG power, delta power, and/or the correlation between the left and right eye movements.

In at least one embodiment, when excessive EMG power is resulting in the EEG being staged as awake when the patient is asleep, the algorithm thresholds may be automatically adjusted or permit the caregiver to adjust the threshold to accommodate this condition. For example, if the caregiver visually detects elevated EMG and the patient is asleep, the systems described herein may enable the caregiver to increase the threshold so that the system stages the periods as light sleep. In some embodiments, the increase may be implemented by the system (e.g., computer system 390), for example based in part on a determination that the person is asleep (e.g., through an absence of body movement or the like).

FIG. 13 illustrates a flowchart of an example process 1300 for monitoring physiological signal patterns to identify patterns that may disrupt sleep and compromise sleep quality. FIG. 13 may be implemented as part of step 820 of FIG. 8 or as a separate process. FIG. 13 may be implemented using the various systems described above in FIGS. 1-5.

In some embodiments, monitoring physiological signal patterns may be based, in part, modified staging rules as described above in connection to FIG. 12. For example, the staging rules may be modified based on medication provided to the patient, hospitalization of the patient, and/or the patient being admitted to the ICU. Process 1300 begins with acquiring (step 1305) and characterizing (step 1310) physiological signals as described above (e.g., steps 805 and 810 of FIG. 8). The process 1300 then proceeds with staging sleep using modified staging rules at step 1315 (e.g., as modified according to FIG. 12). The process 1300 then identifies abnormal EEG power spectra patterns (step 1320), periodic awakenings (step 1325), periodic cortical arousals (step 1330), periodic movement patterns (step 1335), periodic sound patterns (step 1340), and periodic hear rate patterns (step 1345). In some embodiments, one or more of the identified patterns of steps 1320-1345 may be used, for example, as part of step 820 of FIG. 8 and/or to reclassify the stages in steps 1250 of FIG. 12.

In some embodiments, the systems herein may be configured to automatically identify conditions via the process 1300 that are affecting the patient's quality of sleep and utilize this information. One or more of the plurality of physiological channels may be utilized to identify and compare patterns to infer the presence of a condition and/or effect of medication. The systems may then utilize this information in, for example, modifying sleep staging rules (e.g., FIG. 12) or identifying interventions for improved care (e.g., FIGS. 6 and 7).

For example, an implementation of step 1340 may include a sound channel that can be monitored to recognize sound patterns (e.g., step 1340). Certain sounds may interfere with a patient's ability to fall asleep or cause the patient to arousal from sleep. Thus, the DAU 110 may utilize the acoustic microphone 314 to detect sounds above a predetermined limit that may cause such interference. In some embodiments, a sound over 40 dB may interfere with their ability to fall asleep or cause the patient to arousal from sleep. However, any limit may be applied based on the particular environment. For example, the limit in a hospital may be greater than the limit for a quiet room. In some embodiments, when the patient is mechanically ventilated, repetitive patterns of periodic awakening can suggest dyssynchronous breathing or an incorrect setting of respiratory frequency. In some embodiments, the periodicity may be set to <2 min intervals, however other limits may be applicable. If the patient is extubated, repetitive disruptions can be attributed to untreated obstructive sleep apnea (OSA) and/or sleep disordered breathing (SDB).

As many as 40% of patients over the age of 50 who undergo general anesthesia have undiagnosed SDB. SDB may only be observable when a patient attempts to spontaneously breath (i.e., is not mechanically ventilated). Thus, SDB is typically confirmed using nasal airflow and oximetry signals. However, by using the systems and methods described herein, SDB patterns may be distinguishable using other physiological signals (e.g., FIG. 13).

Figures 14A, 14B:
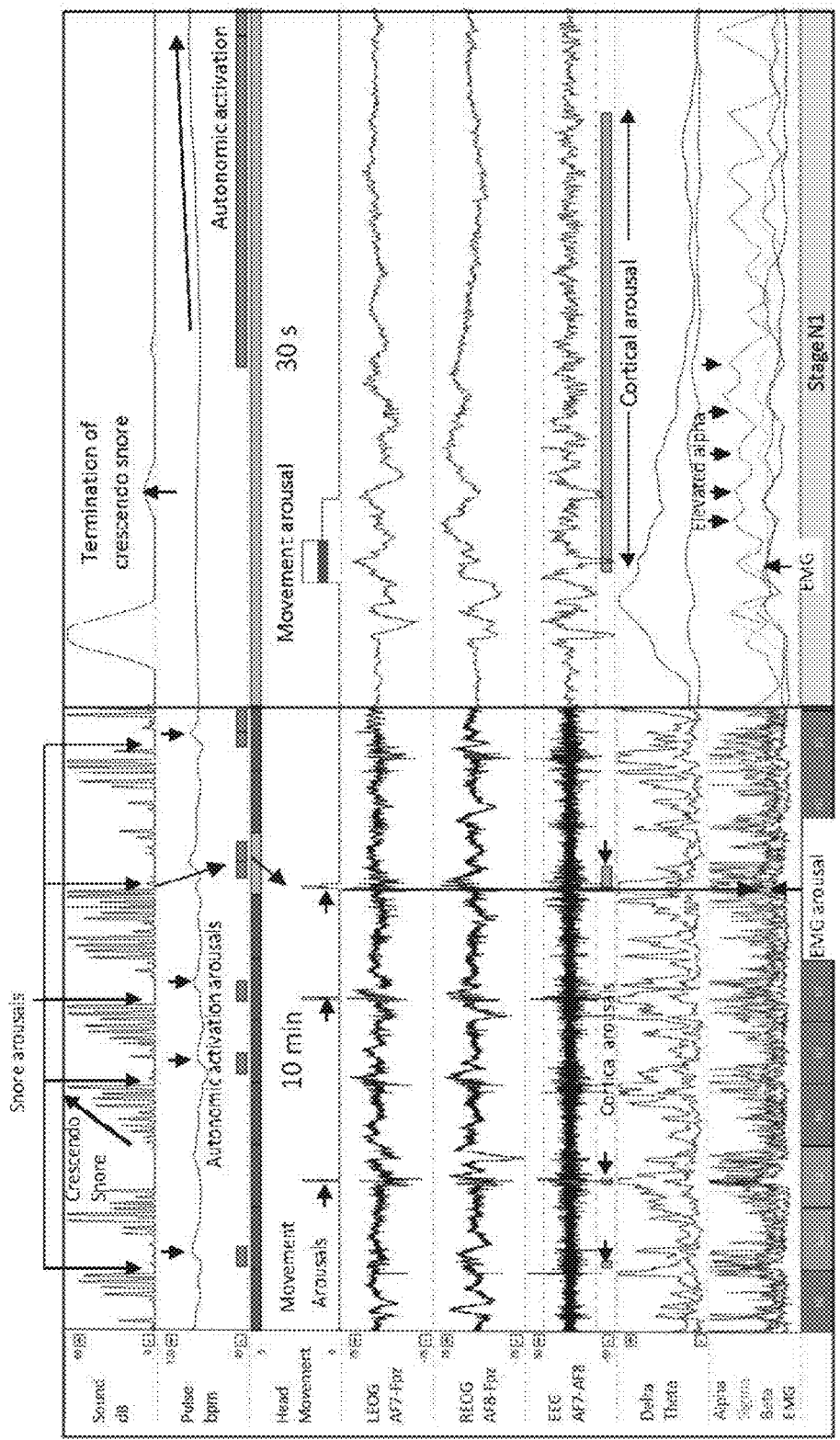
FIGS. 14A-14B include data illustrating an example of physiological signal patterns indicative of sleep disordered breathing, in accordance with embodiments herein.

For example, FIGS. 14A and 14B illustrate data of an example of signal patterns indicative of sleep disordered breathing. The sleep disordered breathing may be detected (e.g., visually or automatically using a computer) by the characterization of the physiological signals acquired with the DAU 110. For example, a crescendo pattern in snoring may be indicative of a collapsing airway (e.g., FIG. 14A). In some implementations, this crescendo pattern may be identified through step 1340. The abrupt termination of crescendo snoring may be indicative of the return of airway patency and resumption of breathing (e.g., FIG. 14B). The arousal (e.g., identified in step 1330) associated with the resumption in breathing may be identified in multiple physiological signals. For example, arousals may be identified in brief increases and decreases in autonomic activation appearing in the heart/pulse rate signal (e.g., step 1345), head movements (e.g., step 1335) associated with a gasp, and increases in alpha and EMG activity (e.g., step 1320) relative to the other power spectra corresponding to cortical or micro arousals (e.g., FIG. 14B). One or more or all of the SDB confirmatory patterns may be apparent with each SDB event (e.g., FIG. 14B). SDB may occur in repetitive patters of known durations (e.g., 30 sec to 120 sec durations), detection may be enhanced when the signals are viewed on a time scale greater than the shortest duration, for example, 30 sections (e.g., the standard time scale for staging sleep). Sleeping position may additionally be used to confirm SDB patterns given SDB and typically more severe when the patient is sleeping supine (e.g., the patient is on his/her back).

While an implementation of FIG. 13 is described above with reference to SDB, it will be appreciated that other conditions may be identified in accordance with the disclosure herein. For example, other ailments and/or medication effects on sleep have been and will be described in connection with FIGS. 8-28. Thus, one skilled in the art will understand how to implement each type of data to define rules for identifying conditions in accordance with FIG. 13.

In an embodiment, it may be advantageous to monitor for and/or identify abnormal EEG waveforms. These abnormal EEG waves may be polymorphic delta activity, triphasic waves, and/or sepsis-associated encephalopathy, which may be collectively referred to as abnormal slow wave activity (ASWA). As described above, according to some embodiments, the acquired physiological signal data can be downloaded to an external computer system 390 for processing and identification of the ASWA or, in some embodiments, by firmware included on DAU 110. Alternatively, or in combination, the data may be displayed by the external computer system 390 for visual inspection and identification by users.

Figure 15:
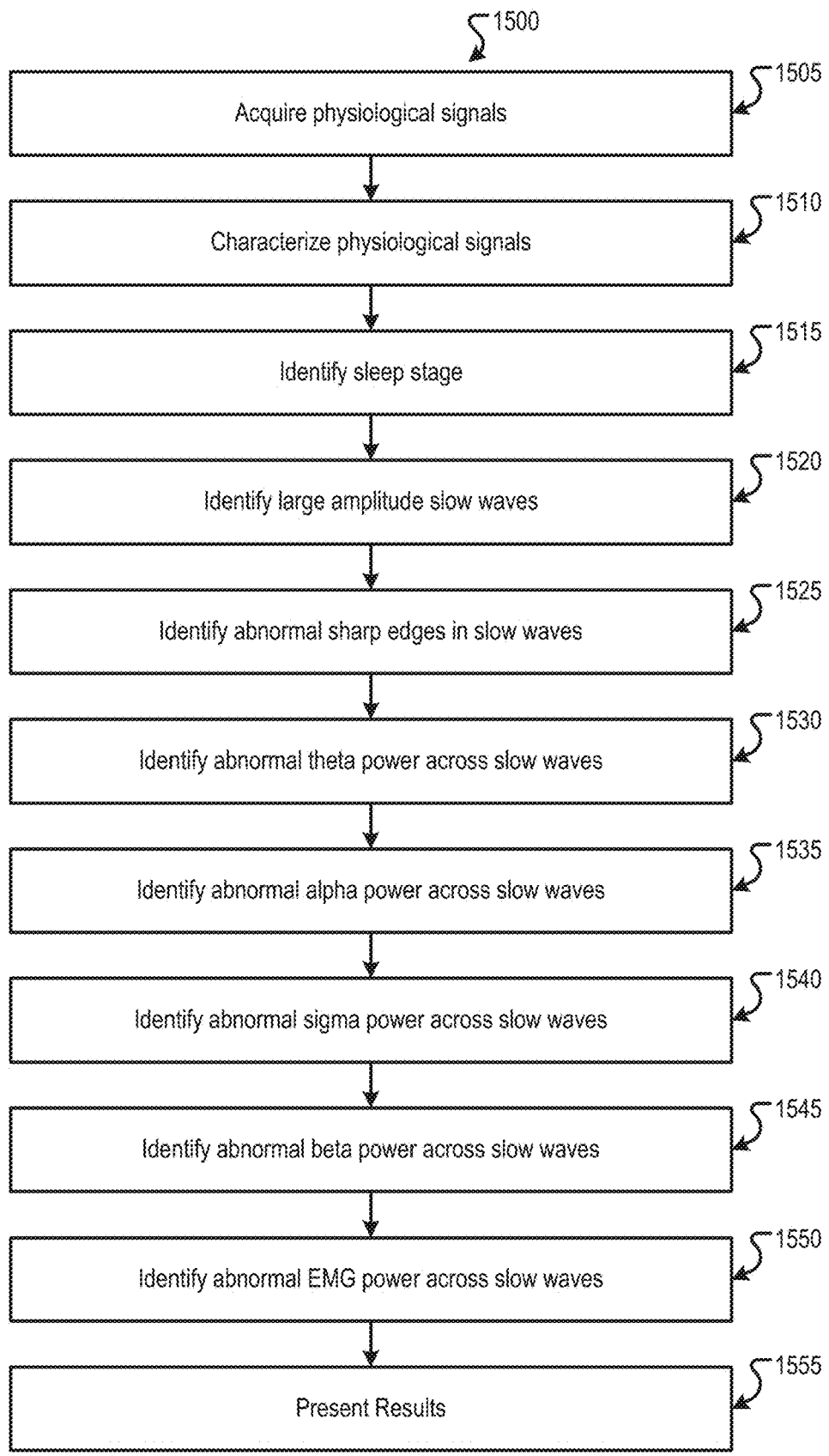
FIG. 15 is a flow chart of a method for detection of abnormal slow wave activity, in accordance with embodiments herein.

The representation of ASWA (either visually or in processing) is similar to slow wave sleep (i.e., large delta waves). However, ASWA can occur during sleep or wake with eyes open or closed. FIG. 15 illustrates a flow chart of an example process 1500 for the automated detection of ASWA. FIG. 15 may be implemented as part of step 830 of FIG. 8 or as a separate process. FIG. 15 may be implemented using the various systems described above in FIGS. 1-5.

In some embodiments, detection of ASWA may be based in part on identification of sleep stages of a patient. The sleep stages, in some embodiments, may be in accordance with convention sleep staging rules and/or otherwise modified as described in connection to FIG. 12 above. Process 1500 begins with acquiring (step 1505) and characterizing (step 1510) physiological signals as described above (e.g., steps 805 and 810 of FIG. 8). The process 1500 then proceeds with identifying a sleep stage at step 1515, identifies a plurality of abnormal characteristics of slow waves to detect and/or identify ASWA at steps 1520-1550, and then optionally presents the results at step 1555. In some embodiments, presenting results 1555 may comprise at least one of automatically identifying an intervention based, in part, on the ASWA as described herein (e.g., FIG. 5 and/or FIG. 7) and/or visually representing the results to a user to facilitate user action based thereon.

The flow chart in FIG. 15 provides one approach for the automated detection of ASWA. An elevated delta power (e.g., 1-4 Hz) can be attributed to numerous factors, including brain activity (slow wave sleep), ocular activity (e.g., slow roller and rapid eye movements, and blinks and saccades), and artifacts (e.g., respiratory, sweat, and movement). Thus, further characterization of the signal is needed to differentiate ASWA from other factors that increase delta power (i.e., ocular activity and artifact). Accordingly, in the example of FIG. 15, identifying ASWA may include at least one or more of: identifying large amplitude slow waves (step 1520), identifying abnormal sharp edges in slow waves (step 1525), identifying abnormal theta power across slow waves (step 1530), identifying abnormal alpha power across slow waves (step 1535), identifying abnormal sigma power across slow waves (step 1540), identifying abnormal beta power across slow waves (step 1545), and identifying abnormal EMG power across slow waves (step 1550).

In various embodiment, epochs can be first staged using algorithms designed to mimic the standard sleep staging rules (as described above in connection to step 1210 of FIG. 12), and only those periods detected as awake and stage N3 may be evaluated for ASWA (e.g., FIG. 15). The physiological signals are evaluated for ASWA without consideration of the sleep stage (e.g., between awake or N3 sleep), because ASWA may occur during both sleep and wake (e.g., with or without frontal muscle tone). In various embodiments, the method previously described to detect the sharp edges in ocular activity (e.g., FIGS. 10A-10C) can also be used to differentiate normal slow wave brain wave and ASWA. In another embodiment, sharp edged waveforms may be viewed on a predetermined time scale (e.g., 30 seconds) and the magnitude of the EMG may be viewed on a second predetermined time scale (e.g., 30 minutes) as a way to identify and detect ASWA. The time scales may be any desired time scale necessary to fully evaluate and identify ASWA, and need not be the same or different.

Figure 16:
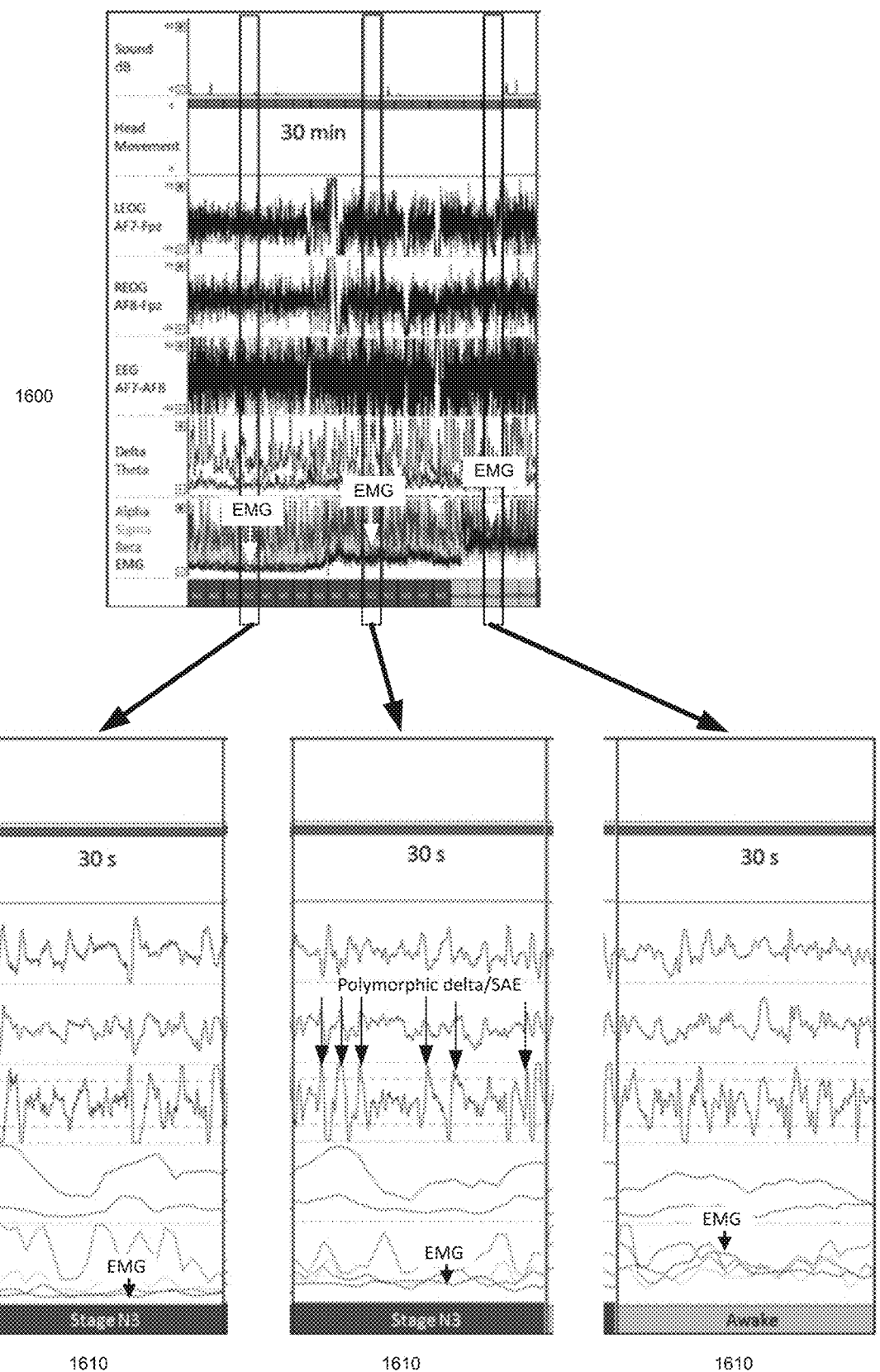
FIG. 16 includes data illustrating an example of physiological signal patterns indicative of abnormal slow wave activity, in accordance with embodiments herein.

FIG. 16 includes data illustrating example physiological signal patterns that may be used for detecting ASWA in accordance with FIG. 15. For example, FIG. 16 depicts a data signal 1600 measured on a long time scale (e.g., 30 minutes) including three ASWA periods with markedly similar EEG waveforms (e.g., 1610, 1620, and 1630, each shown on a shorter time scale of 30 seconds). FIG. 16 illustrates that it may be difficult to detect (e.g., visually) an increased frontal muscle tone that occurs when awake stage is difficult to detect, as is an increased EMG power relative to the other power bands. Without detection of the relative increase in EMG power (1600) on a longer time scale, it would be difficult to distinguish between an awake and sleep conditions on a traditional 30 second time scale. Although the characteristics of ASWA include suppressed theta and sigma relative to delta and alpha power, respectively, visual recognition of these patterns using only the EEG waveform (e.g., comparing the EEG waveform in FIG. 11C with that of 1610) is difficult, even with the presentation of the associated power bands. Manual or automated characterization of ASWA (i.e., abnormal brain activity) as stage N3 (i.e., healthy, deep sleep) my not only inaccurate, but also may compromise the possible early recognition of the onset of sepsis. Differentiating between ASWA from N1, N2, and N3 can be achieved by the characterization and identification of suppressed theta and sigma power relative to delta and alpha power, respectively (e.g., steps 1530-1550). The magnitude of EMG power may also be used to differentiate abnormal ASWA during sleep and awake.

Figure 17:
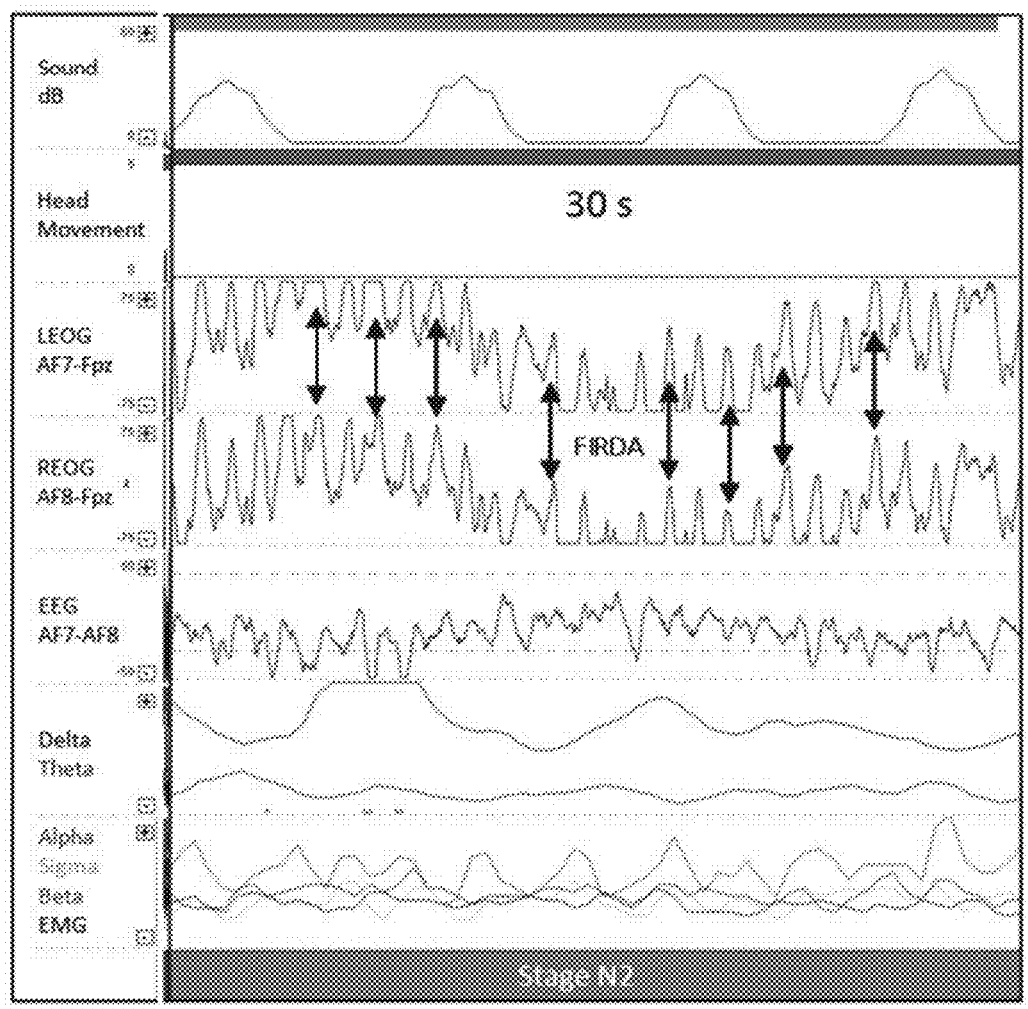
FIG. 17 includes data illustrating an example of physiological signal patterns indicative of frontal intermittent rhythmic delta activity, in accordance with embodiments herein.

The identification of sharp edged brain wave patterns (e.g., step 1525) can also be used to differentiate ASWA associated with polymorphic delta activity or sepsis-associated encephalopathy (SAE) from ASWA associated with frontal intermittent rhythmic delta activity (FIRDA). For example, FIG. 17 includes example data illustrated physiological signal patterns indicative of ASWA associated with FIRDA. The data of FIG. 17 is an illustrative example of physiological signal patterns with in-phase delta activity that may be an indication of FIRDA. FIRDA is another manifestation of abnormal brain activity that benefits from analysis of a 30 sec time scale as shown in FIG. 17. Recognition of FIRDA may benefit from access to both differential and referential EEG recordings, because the magnitude of the FIRDA activity is attenuated when amplifier common mode rejects differential signals with high coherence. FIG. 17 illustrates an example showing both an attenuated differential signal as well as referential signals presents in the LEOG and REOG channels.

In an embodiment, abnormal power in the theta, alpha, sigma, beta and EMG bands (e.g., as identified in steps 1530-1550) may be combined with a magnitude of decontaminated delta power and the sharp edged slow wave activity to further characterize and identify ASWA (e.g., differences in signals staged N3 in FIGS. 11A and 11B).

In various embodiments, machine learning techniques may be utilized to employ the remaining steps of FIG. 15 in order to differentiate ASWA from other conditions, e.g., ASWA vs. healthy slow wave activity, healthy awake, FIRDA, ocular activity, or artifact, etc. For example, the acquired physiological signal data can be downloaded to an external computer system 390 comprising machine learning software executed by a processor for processing and identification of the ASWA. For example, the external computer system 390 may be configured to build a database of physiological signals that have been differentiated from other conditions, which may be accessed as part of the identification of ASWA in subsequent implementations of FIG. 15. Alternative approaches to machine learning can be used for the purpose of ASWA detection, e.g., detection of values that exceed empirically defined thresholds. Both absolute and relative power values can be used for this step, and the ratio among the bands may also be useful in the characterization of ASWA.

While the use of machine learning is described in connection with detection of ASWA. It will be appreciated that machine learning techniques can be utilized to detect any of the abnormal physiological signals patterns described throughout this disclosure. For example, machine learning techniques may be implemented to recognize signal patterns indicative of any of the conditions described in FIGS. 8-28, and thus determine that the recognized pattern is indicative of an associated abnormal condition or pattern. That application to ASWA is merely intended as an illustrative example. Example machine learning algorithms include, but are not limited to, artificial intelligence, image processing techniques (e.g., machine vision, stitching, filtering, thresholding, pixel counting, segmentation, edge detection and tracking, color analysis, object recognition, pattern recognition, blob detection and extraction, optical character recognition, and the like), parsing of data objects and/or associated metadata, and the like. Thus, the computer systems described herein may be configured to automatically recognize an abnormal signal pattern, associate the recognized pattern with an abnormal condition thereby detecting the abnormal condition, and either report the presence of the abnormal condition and/or take action in response thereto as described above in connection with FIGS. 6 and 7.

In at least one embodiment, the alpha power can be normalized (e.g., divided by) the sum of the theta, alpha, sigma, beta and EMG power bands to accommodate individual differences in the generation of alpha power and the impact of medications on the absolute alpha power. Additional ratios useful in the detection of abnormal slow waves include the alpha/beta, theta/EMG, alpha/EMG, theta/sigma, delta/beta and sigma normalized to the sum of all six frequency bands. One skilled in the art will recognize that different ratio combinations can be computed and employed to improve the sensitivity and specificity of the signal pattern detector.

Figure 18:
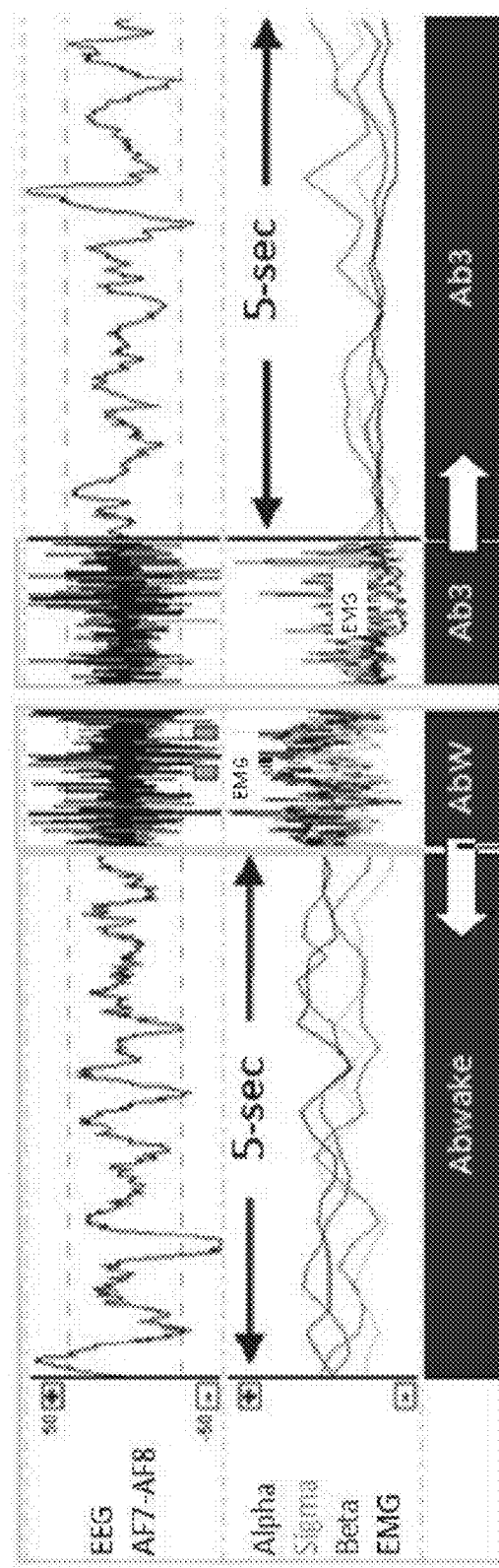
FIG. 18 includes data illustrating another example of physiological signal patterns indicative of abnormal slow wave activity, in accordance with embodiments herein.

Additionally, the cut off frequency and sharpness of the low pass filter applied to the EEG signal (e.g., at step 1510) may affect the magnitude of the power measured in the EMG range. For example, the difference in EMG power, when different low pass filters are applied, may be used to assist in differentiating elevated EMG associated with increased muscle tone when awake from elevated EMG power resulting from the influence of sharp edged ASWA. In an example embodiment, ASWA may be detected for both sleep and awake conditions, and annotated for visual detection in a manner similar to that illustrated in FIG. 18 with Ab3 (e.g., normalized sum of power bands in stage N3) when asleep and AbWake (e.g., normalized sum of power bands) when awake. FIG. 18 illustrates an example of ASWA, where EMG power may assist in the properly staging a current sleep stage as AbWake when awake and Ab3 when asleep.

Returning to FIG. 8, recovery during hospitalization may include, not only adequate quantity and quality of sleep, but also effective management of abnormal neurological activity (e.g., steps 825-265). Other than patients in a neurological intensive care unit or having witnessed convulsive seizures, the EEG is not routinely monitored, even though burst suppression and non-convulsive epileptiform activity is relatively common in hospitalized patients and is associated with less favorable outcomes (e.g., slow or non-recovery). One of the reasons that EEG is not routinely monitored in hospitalized patients is that a trained EEG technician typically is needed to apply the full montage, continuous EEG acquisition system. Additionally, these conventional EEG acquisition systems are large and expensive, and thus further limit routine monitoring on all patients as a precaution. Another limitation of conventional EEG is that an EEG technician and/or neurologist (e.g., expert) is needed to monitor the signals in real time to detect abnormal patterns.

Traditionally, conventional EEG systems were needed to detect the focal site of a seizure. Furthermore, recognizing the occurrence of non-convulsive seizure activity can only be detected in the vast majority of cases using a limited channel monitoring device such as these conventional EEG systems, which were only used intermittently due to complexity and costs. In contrast, the systems and methods disclosed herein (e.g., DAU 110 and the system of FIG. 5) provide a light, relatively inexpensive means for monitoring EEG in a form factor that can be affixed by any caregiver with very limited technical training. As described above, the DAU 110 is light and mobile, and with an external battery pack affixed, it can be used for continuous, wireless recording and monitoring of different combinations of physiological signals as described herein. The DAU 110 may provide voice messages to identify when signal quality is poor. Skin-sensor impedances can be acquired periodically to assist in the identification of poor signal quality. In various embodiments, the signals can be recorded to a memory in the DAU 110 (e.g., a memory of the DAU 110 or a removable memory card) and may be reviewed off-line by an expert. In some embodiments, alone or in combination, the EEG signals can be monitored remotely in real time by an expert. In at least one embodiment, the physiological signals are transmitted to small, tablet size computer (e.g., mobile device 550 or computer system 560). Software installed therein (or in the computer system 390) may be executed by a processor to characterize, analyze, and automatically execute interventions such that a caregiver need not be consulter or otherwise intervene with the sleep of the patient. Alternatively, or in combination, the software may be executed to also present the characterized signals in a manner that provides a caregiver having limited technical training the capability to monitor the physiological signal patterns. Based thereon, the caregiver may then be able to abnormal patterns similar to the monitoring of other vital signs, and to recognize when an expert is needed for a more careful review.

Mechanically ventilated patients are typically sedated and sedated patients generally have a sleep efficiency of at least 50% (i.e., asleep for at least 50% of the attempted time). Elevated EMG burst activity may cause epochs to be improperly staged awake, and elevated EMG burst activity can be attributed to ventilatory distress (e.g., incorrect pressure, problems with the breathing tube, asynchronous breathing, etc.). Thus, interpretation of EMG burst activity may require analysis multiple physiological signals, which may include any combination of the sound, power and LEOG, REOG and EEG signal panes, and time scales. For example, there may be a benefit to analyzing the signals on a time scale greater than 30 seconds, for example, to confirm the EMG bursts are not correlated with changes in the sound channel (e.g., snoring sounds).

Figures 19A, 19B:
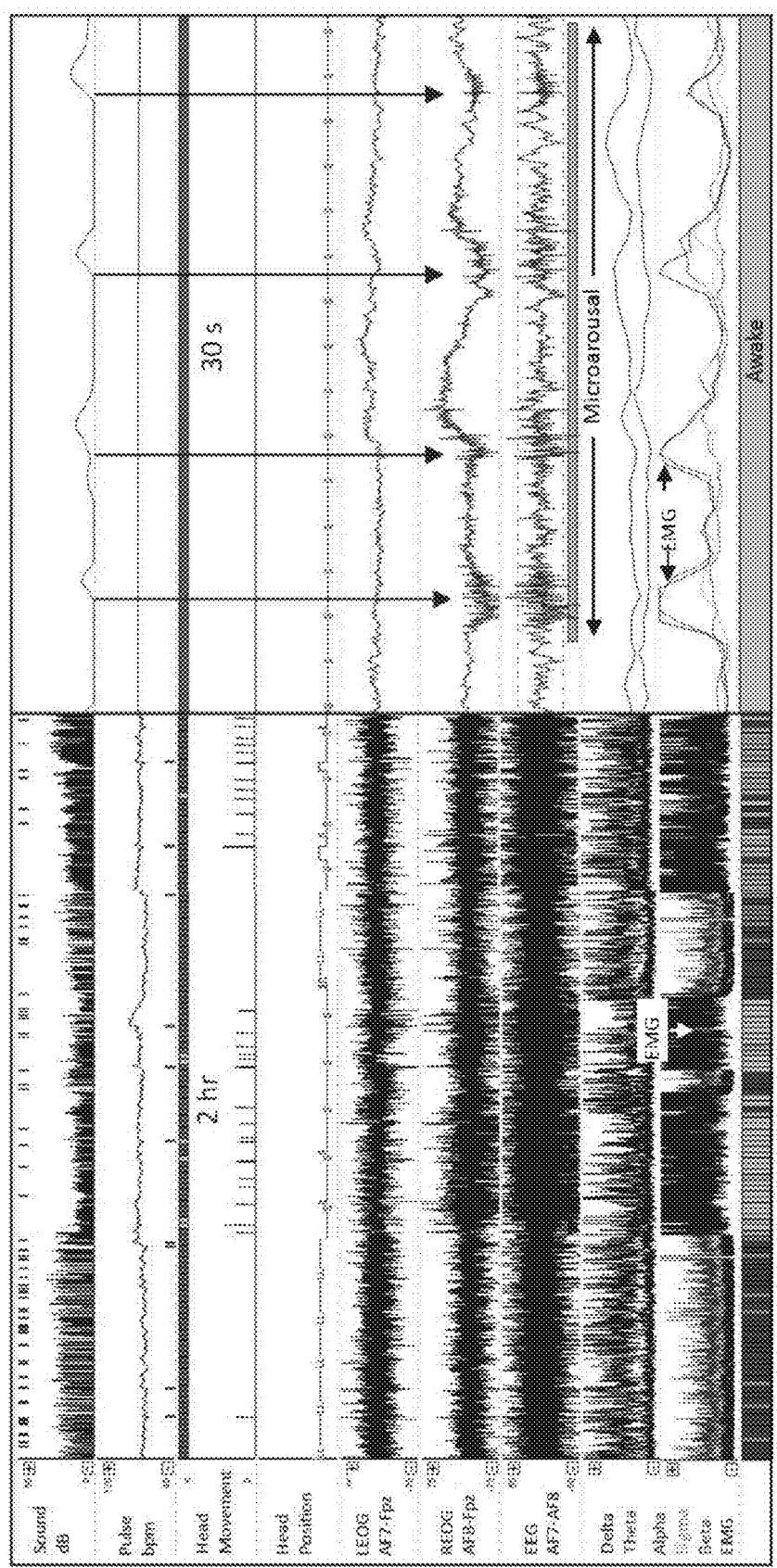
FIGS. 19A and 19B include data of an example of physiological signal patterns an elevated by steady sound experienced by the patient, in accordance with embodiments herein.

FIGS. 19A and 19B include data of an example physiological signal pattern of an elevated by steady sound experienced by the patient. FIG. 19 is an illustrative example of signal patterns having gross excursions of EMG power apparent only when the patient was in the supine position coupled with loud steady sound. The example data of FIG. 19 was collected over a 2 hour time scale (e.g., FIG. 19A), with a relatively large, steady sound that is recorded (e.g., at step 1340 of FIG. 13) throughout the time scale (e.g., nocturnal hours in one embodiment). Sustained, gross excursions of EMG power may be observed when the patient is in the supine position. FIG. 19B illustrates signal excerpts on a 30 second time scale including bursts in the EMG power corresponding to increases in sounds in, for example, a mechanically ventilated patient. The steady, elevated sound coupled with the surge in EMG associated in the supine position that results in awakenings from sleep may be an abnormal signal pattern (e.g., as identified by the method of FIG. 15) that can disrupt sleep continuity. These small bursts derived from the EEG sensors appear to be timed to respiration and are detected and marked in FIG. 19B as a relatively long microarousal in the epochs staged as sleep.

FIGS. 20A-20D include data of an example physiological signal pattern of an EMG power bursts. FIGS. 20A-20D may be illustrative of signal patterns of repetitively timed EMG power burst patterns that may be indicative of a ventilator distress (e.g., extreme ventilatory asynchrony) and/or central sleep apnea associated with arousals. For example, FIGS. 20A-20D depict EMG power burst patterns including multiple power bursts on time scales of 1 hour (FIG. 20A), 30 min (FIG. 20B), 10 min (FIG. 20C), and 30 s (FIG. 20D). FIGS. 20A and 20B identify consistent patterns of EMG bursts being automatically identified as microarousal events (e.g., shown as grey boxes in the EEG band). FIG. 20C illustrates that a shorter time scale (e.g., 10 minutes) may beneficially permit detection of the consistency of the EMG burst pattern. For example, the example EMG events of FIG. 20C are depicted at least 10 sec in duration and occur repetitively every 30 seconds. Thus, the systems herein may be configured to determine that the EMG bursts are not correlated with each breath (e.g., during loud snoring), because breathing occurs between 8 and 24 times per minute. The EMG power, when viewed on an even shorter time scale (e.g., 30 sec of FIG. 20D), presents four unique EMG excursions within each EMG event (e.g., 4 times in ~10 sec). In some embodiments, SDB may be ruled out based on previous knowledge or data indicating a patient is mechanically ventilated. The repetitive timing of the illustrated microarousals may be suggestive of an association with the mechanical ventilation, possibly extreme asynchrony, central sleep apnea related arousals, or irritation from the ventilation tube when swallowing. In this case, further investigation may be warranted (e.g., via recommendations and/or interventions in accordance with FIGS. 5 and/or 7) because the abnormal EMG patterns (e.g., as determined in FIG. 15) indicate the patient may be unable to fall asleep. Both of these examples of identified abnormal signal characteristics can be computationally detected and identified by a computer system 390, computer system 560, and/or mobile device 550 based on analysis physiological signal patterns. Similarly, these examples of identified abnormal signal characteristics can be visually detected by a caregiver based on the unexpected sleep stage, presentation of automated feature extractions, and/or how the signal information is presented by a graphical user interface (as described below in connection to FIGS. 29-31). Access to the staging of awake when the patient should be asleep and access to the signal patterns in near real time, while observing the patient, may facilitate determination of a cause of the EMG burst activity and implementation of the appropriate intervention.

Returning to FIG. 8, in some embodiments, undetected abnormal neurological signal patterns, such as burst suppression (e.g., step 840) and non-convulsive epileptiform activity (e.g., step 850) may contributes to a slower recovery or increased risk of mortality to patients. In conventional EEG systems, these abnormal patterns are not generally detected because EEG is not routinely monitored. Advantageously, the DAU 110 may provide inexpensive and ease of use for non-experts to affix the sensors to the patient (as described above) to achieve the continuous monitoring of these abnormal neurological activities, as well as for monitoring circadian rhythm and other sleep activity described herein. One skilled in the art will recognize that acquisition of EEG from a limited number of sensor sights (e.g., frontopolar EEG) does not replace the topographic information obtained from a dense sensor array (e.g., standard 10-20 montage). Although some abnormal neurological activity will not be detectible with a limited sensor montage depicted in FIG. 1 and source localization is not possible, the described system capable of or continuous monitoring for gross abnormal neurological activity, in addition to monitoring sleep/wake.

Burst suppression is an epileptiform signal pattern that can be associated with poor recovery outcomes as well as with heavy doses of sedatives. FIGS. 21A-23B illustrate data of example physiological signal patterns of abnormal burst suppressions. In some embodiments, FIGS. 21A-23B may be indicative of the burst-suppressions identified, for example, at step 840 of FIG. 8. For example, these examples may be indicative of abnormal burst suppression obtained from the frontopolar sites and readily detectible in one or more of the various power band patterns (e.g., as identified in FIG. 15). As described above, according to some embodiments, the acquired physiological signal data can be obtained by the DAU 110 and downloaded to an external computer system 390 for processing and identification or, in some embodiments, by firmware included on DAU 110. Alternatively, or in combination, the data may be displayed by the external computer system 390 for visual inspection and identification by users.

FIGS. 21A-21D illustrate example signal patterns of burst suppression increasing smaller time scales, for example, of 1 hour (FIG. 21A), 30 min (FIG. 21B), 10 min (FIG. 21C), and 30 s (FIG. 21D). Such burst suppression may be present in alpha and sigma power bands characterized by automated scoring as cortical arousals and sleep spindles. During burst suppression and/or isoelectric activity, the power across all bands may approach zero with subsequent bursts of alpha and sigma power measurements. These abnormal EEG burst patterns can be can be misclassified as either sleep spindles or cortical arousals (e.g., as shown in FIG. 21D) and result in an epoch being auto-staged non-REM, because the prominent characteristic of such burst suppression are alpha and sigma power excursions. The combination of low power interspersed with detected arousals and spindles may be utilized to identify burst suppressions (e.g., step 840). In some embodiments, alpha burst and/or sigma bursts (or both) can be identified by the systems described herein and used to detect arousals and sleep spindles. Thus, such bursts in alpha and/or sigma power may be combined with one or more additional identifications (e.g., detect rapid increases and/or decreases of power bands as well as periods of suppressed) to facilitate burst suppression detection. In some embodiments, for example, the systems and devices (or caregivers in some embodiment's) may be configured to recognize repetitive cortical arousals and spindles coupled with power spectra patterns showing high voltage bursts that alternate with coma-like brain activity may facilitate detection of burst suppression activity. In some embodiments, the presence of such identifying characteristics over a time equal to or greater than a pre-determined threshold time (e.g., 30 seconds, 40 seconds, or other as desired time scale for the specific application) may be further indicative of detected burst suppression activity.

Figures 22A, 22B:
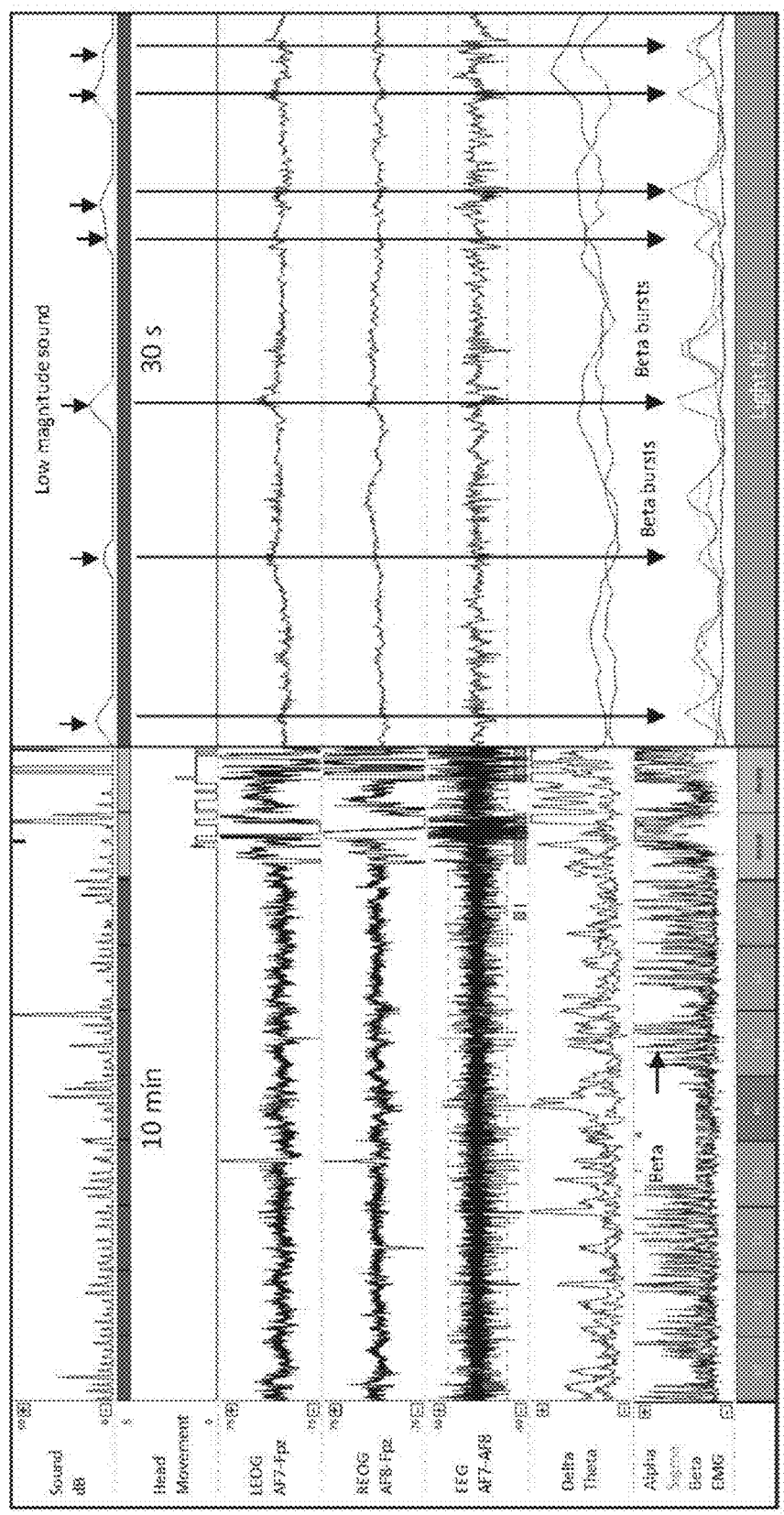

In another embodiment, alone or in combination, abnormal EEG activity (e.g., as identified in FIG. 15) can manifest as burst patterns of beta power. Recognition of beta bursts during visual inspection of the EEG signal may be more difficult than evaluating the relative power characteristics on different time scales. In some embodiments, burst oscillations may be most noticeable in beta power that coincides with low amplitude bursts in sound. For example, FIGS. 22A and 22B illustrate data of example physiological signal patterns that may be used to identify burst patterns of beta power. FIG. 22A illustrate that the magnitude of the beta bursts, relative to the sigma power (which influenced the staging as Light N2), may be recognizable when viewed on a 10 min time scale opposed to a shorter time scale (e.g., 30 seconds of FIG. 22B). When viewed on the shorter scale, beta bursts synchronized with the breathing can be detected. The temporal synchrony of beta power bursts and snoring (in the sound signal) can indicate a neurophysiological response to pain.

Figures 23A, 23B:
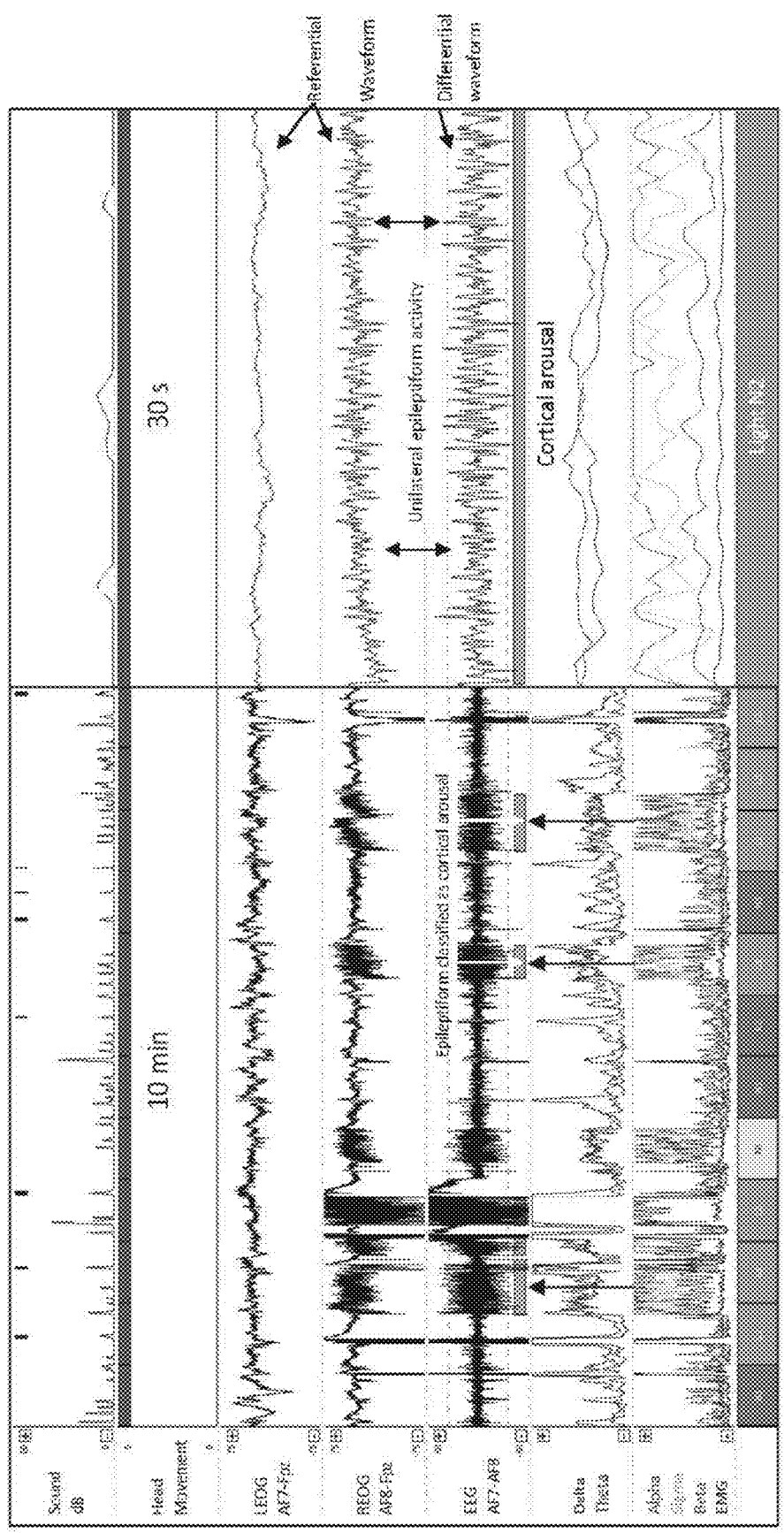

In some embodiments, the systems and methods herein may be configured to detect when epileptiform burst activity occurs in only one side of the brain (e.g., one of the three EEG waveforms is substantially different from the other two). In some embodiments, patterns of large unilateral amplitude bursts of sigma and alpha power may be characterized as long cortical arousals. For example, FIGS. 23A and 23B include data of example physiological signal patterns that may be indicative of unilateral burst oscillations. In some implementations, unusual unilateral burst oscillations can be detected by comparing one or more of the power bands with one or more of the other power bands, where such comparison indicates burst activity in only some of the bands. For example, unusual unilateral burst oscillations can be apparent in the beta, alpha and sigma power bands (e.g., as shown in 10 min time scale of FIG. 23A). These aberrant patterns may be visible in the differential EEG channel and in one or more of the other referential channels. For example, FIG. 23B shows that the REOG referential band is substantially similar to the aberrant patter of the differential EEG channel, while the LEOG signal does not. However, the reverse may also be detected or other bands may lack the aberrant pattern. In some cases, this pattern may be detectible by the abrupt increase in alpha and sigma power when viewed on the longer time scale (e.g., 10 minutes of FIG. 23A) and on shorter time scale (e.g., 30 seconds of FIG. 23B). Depending on the frequency characteristics of the epileptiform activity, the aberrant pattern can be auto-detected as a cortical arousal (e.g., >3 secs of elevated alpha activity) as show in FIG. 23B. In various embodiments, automated detection algorithms to be applied to the patient in response to the periodicity of these power bursts, thereby identifying the bursts and initiating a corresponding intervention (e.g., FIG. 7). Alternatively, the signal patterns may be detectible by visual inspection based on the capability to review the power signals on different time scales and/or the information provided with the characterization of the signals for sleep staging (e.g., FIG. 6).

Normal, artifact free EEG activity typically includes delta power that begins at 2 and beta power that ends at 40 Hz with a maximum amplitude of approximately less than or equal to 75 µV. As much as 70% of non-convulsive seizure activity is detectable from frontal EEG leads. Epileptiform seizure activity is typically high frequency and large amplitude (e.g., >100 µV), similar to EEG artifact that can be recognized by automated detection of large amplitude, short duration changes in the signal waveform.

Figures 24A, 24B, 24C:
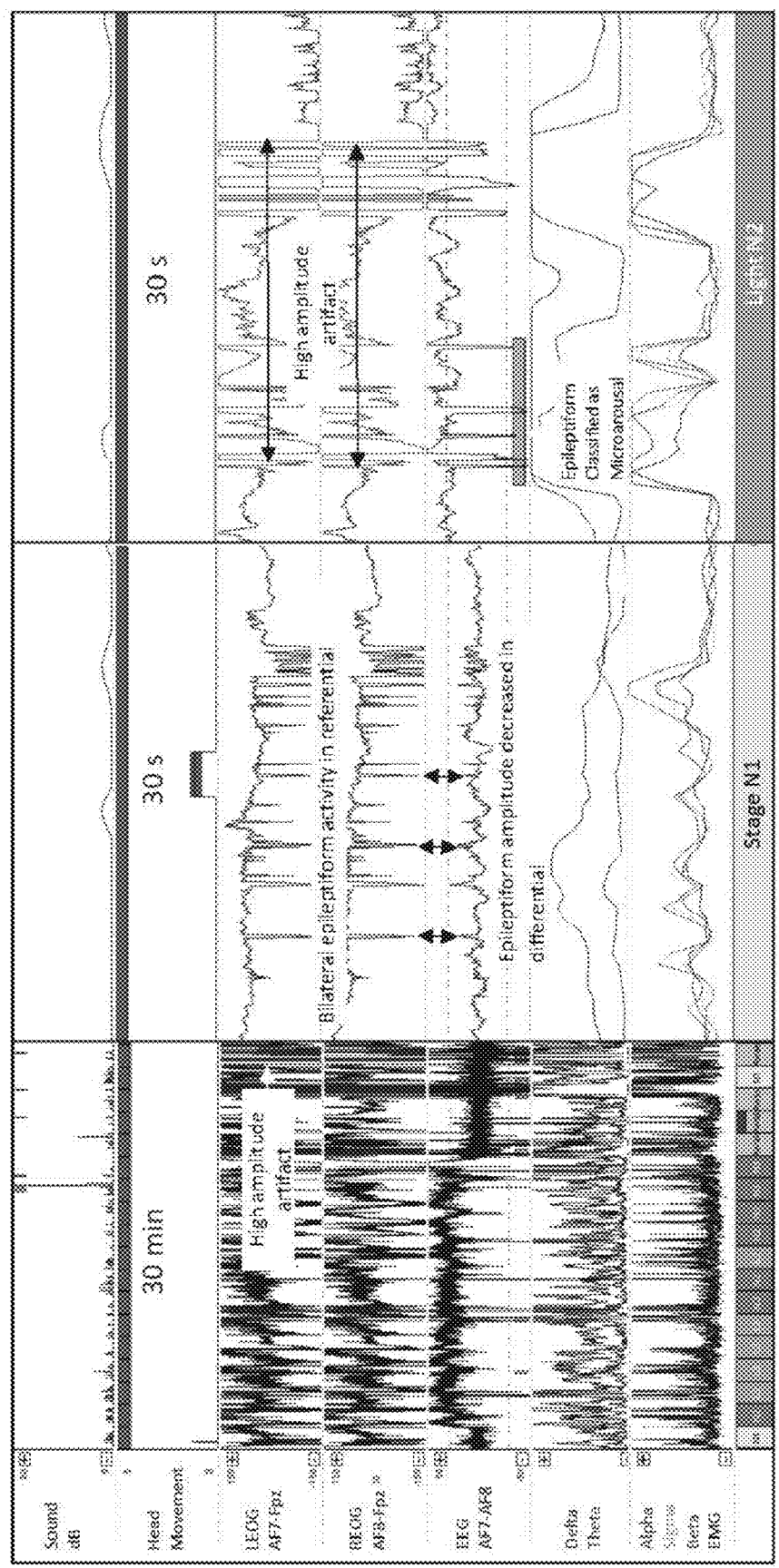
FIGS. 24A-24C include data of example physiological signal patterns indicative of non-convulsive seizure activity, in accordance with embodiments herein.

In some embodiments, large amplitude epileptiform activity may be detected as artifacts and marked (e.g., FIGS. 24A-24C below), with the remaining spikes characterized as bursts in EMG (and other bands) and autoscored as microarousals. FIGS. 24A-24C include data of example physiological signal patterns that may be used to identify non-convulsive seizure activity. In some embodiments, FIGS. 24A-24C may be indicative of the non-convulsive seizure activity identified, for example, at step 850 of FIG. 8. For example, FIGS. 24A-24C illustrate examples of seizure spikes determined to be non-convulsive based in part on an absence of gross head movement. FIG. 24A provides an example of waveforms on a 30 min time scale identified as an artifact detection in combination with very large bursts of EMG power (e.g., high amplitude artifact). Furthermore, as shown in FIG. 24A, there is little to no head movement detected corresponding to the artifact. Thus, in one embodiment, visual inspection of the waveforms on a short time scale (e.g., 30 second of FIG. 24C) and at +/−150 µV scale may confirm the identified artifact is seizure activity. Similarly, automated inspection executed by the external computer system 390 may identify the artifact and a corresponding time of the event, compare this with head movement data associated with that same time period, and if no head movement is detected, identify the artifact as seizure activity. Generally, the amplitude of the signal in the EEG channel is greater than the power in either the LEOG or REOG channels (due to inter-electrode distance and common mode rejection). When the EEG signal is of lower magnitude, as compared to the LEOG and REOG signals, it's likely a result of abnormal neurological activity or artifact.

In some embodiments, seizure activity may be further identified based in part on a bilateral characteristic of the epileptiform activity. For example, FIG. 24B illustrates seizure activity apparent in the referential signals (e.g., labeled LEOG and REOG in this example) but not in the differential channel (e.g., labeled EEG) due to amplifier common mode rejection. Furthermore, despite the attenuated differential signal, the seizure activity causes a wide spectrum of burst activity (e.g., affects the alpha, sigma, beta and EMG power bands). Thus, the presence of one or more of these identified features may be indicative that the epileptiform activity is bilateral.

Healthy sleep is comprised of cycles typically ranging from 60 to 120 minutes in length, and each sleep cycle is typically comprised of 30 sec epochs transitioning from non-REM sleep (Stages N1, N2 and N3) and REM sleep. The systems and methods described herein may be used to monitor physiological signals during acquisition, for example, by the DAU 110 (e.g., a monitor mode) to evaluate either sleep or abnormal neurophysiology. In a second mode the systems and methods herein may be used offline for inspection and/or staging of sleep after the signals have been acquired (e.g., a review mode). In some embodiments, the review mode may be automated using the integrated system of FIG. 5 as described herein. In some embodiments, these modes are independent, e.g., it may not be possible to simultaneously monitor and review the acquired physiological signals. This may be, in part, because abnormal brain activity is much more variable, thereby necessitating an extended period of data collection. In some embodiments, abnormal signals may be present in extended periods of similar abnormal activity (e.g., ASWA) or brief episodes of different types of abnormal activity (e.g., convulsive or non-convulsive seizure activity). Recognizing brief episodes of abnormal brain/sleep activity that would benefit from an intervention requires the capability to simultaneously compare the wave forms as they are being acquired (monitor) in the context of previously recorded signals (review).

Figure 25A:
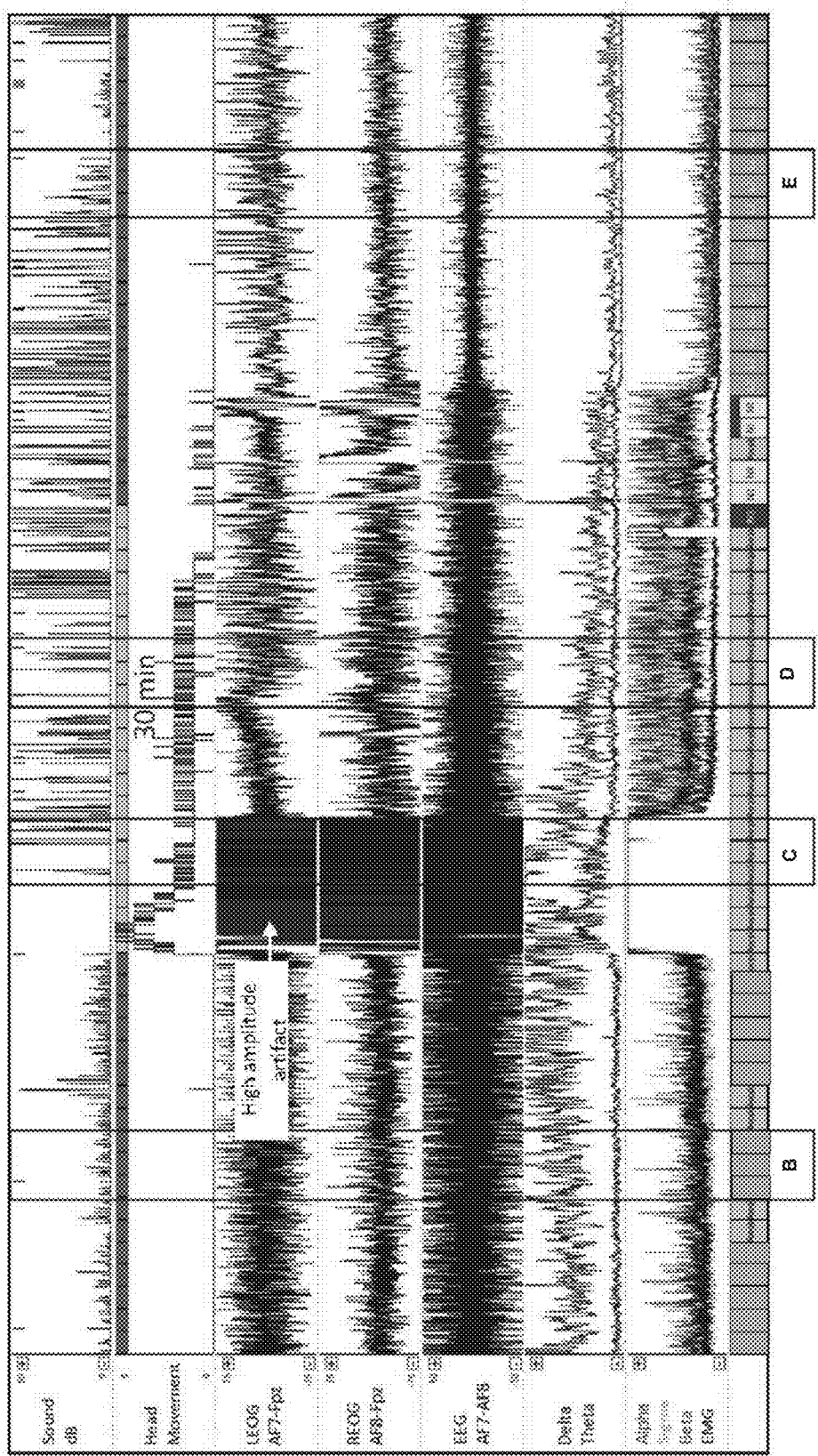
FIGS. 25A-25E illustrates data of an example of physiological data with transitions across different abnormal physiological signal patterns, in accordance with embodiments herein.
Figures 25B, 25C, 25D, 25E:
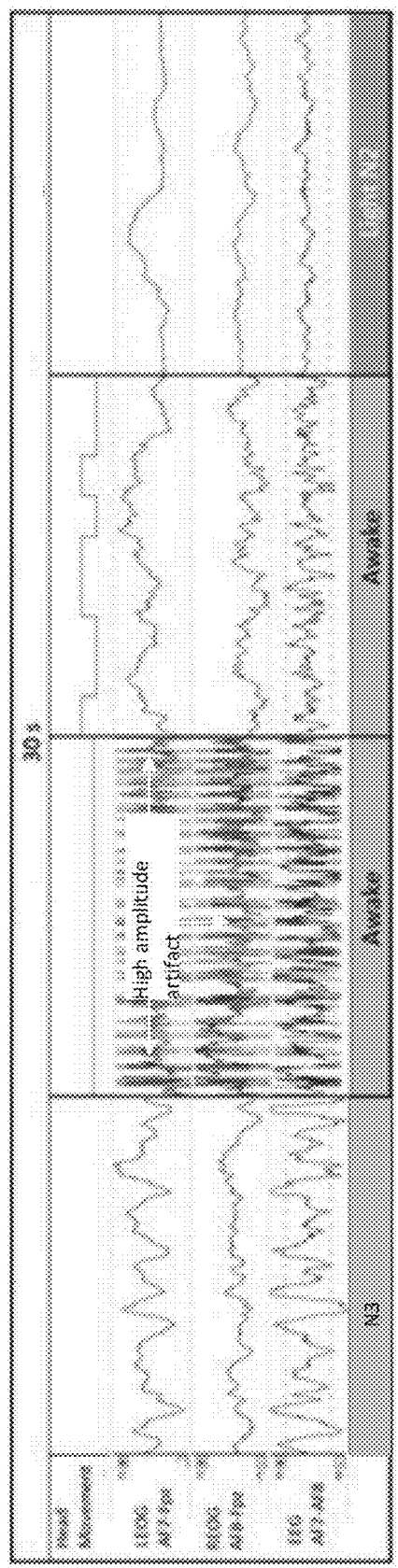

FIG. 25A-25E illustrates data of an example of physiological data with transitions across different abnormal physiological signal patterns. FIG. 25 presents a sequence associated with convulsive seizure activity detected by the signal patterns associated with head movement. FIG. 25A illustrates a 30 min epoch with four segments 2510, 2520, 2530, and 2540. FIGS. 25B-E illustrate the segments 2510-2540 extracted and displayed at a 30 s time scale. FIG. 25B illustrates an extended period of ASWA which is staged abnormal N3. The period is followed by an episode of convulsive seizure activity, observed by large amplitude artifact spikes in the frontal EEG wave forms which are illustrated and coupled with extreme gross movement (e.g., FIG. 25C). FIG. 25D illustrates signals associated with the end of the ictal phase. The electrical seizure activity in the brain has ended, but visible symptoms (e.g., head movement) may persist. FIG. 25E illustrates a postictal period comprised of slow waves and low amplitude EEG indicative of light N2.

FIGS. 25A-25D provide an example as to why it may be beneficial to view the current and previous power signals, sleep staging and wave form data simultaneously while also transitioning among and between different time scales. Furthermore, a capability to be monitor and review on selectable time scales would be beneficial. Once a potentially abnormal period is detected on a long duration time scale, the user may then zoom in to confirm the pattern type. Accordingly, a graphical user interface (GUI) is provided herein, as described in greater detail below in connection to FIGS. 29-31, that provides user interactions for quickly and efficiently searching through currently and/or previously acquired data to determine the frequency and duration of these types of abnormal conditions. In various embodiments, it may be beneficial to use longer duration time scales when searching for abnormal patterns across, for example, an 8 or 12 hour hospital shift or across a 24 hour circadian cycle.

In some embodiments, the physiological signals acquired by the DAU 110 may be used to identify sleeping disorders affecting a patient's ability sleep normally. For example, the signals characterized and identified in FIG. 13 may be indicative of such sleeping disorders. Hospitalized patients may be at greater risk for developing insomnia and/or a circadian rhythm disorder, which in turn can contribute to the onset of delirium. Both of these sleep disorders can be impacted by interrupted sleep during the night and/or intermittently during the day and night, rather than having sleep consolidated during nocturnal hours. Furthermore, such disorders may interrupt the normal progression through the various sleep stages (e.g., awake to NREM into REM and back). Thus, the DAU 110 in combination with the methods described in, for example FIGS. 8-27 may facilitate continuous and real-time monitoring of the patient's sleep patterns. For example, the DAU 110 may collect data from the EEG sensors 310 and process the signals, as described throughout this disclosure, to assist with monitoring the patients sleep cycle. The DAU 110 may detect transitions between the sleep stages that are irregular when compared with a normal sleep cycle. Thus, caregivers (or other automated systems as described herein) may utilize the measurements to identify when a patient is not sleeping enough or experiencing an interruption of their normal sleep cycle. In some embodiments, an appropriate physician may be consulted to administer sedatives or other means to induce and/or steer the patient into a desired sleep stage. Alternatively, the systems described herein may be configured to administer (e.g., automated release of a sedative in accordance with recommendations of FIG. 7) or otherwise steer the patient into a desire sleep stage. Example devices and methods of steering a patients sleep stage is described in greater detail, for example, in U.S. Pat. Nos. 8,628,462; 8,784,293; and 8,932,199, all of which are hereby incorporated by reference in their entirety.

Figure 26:
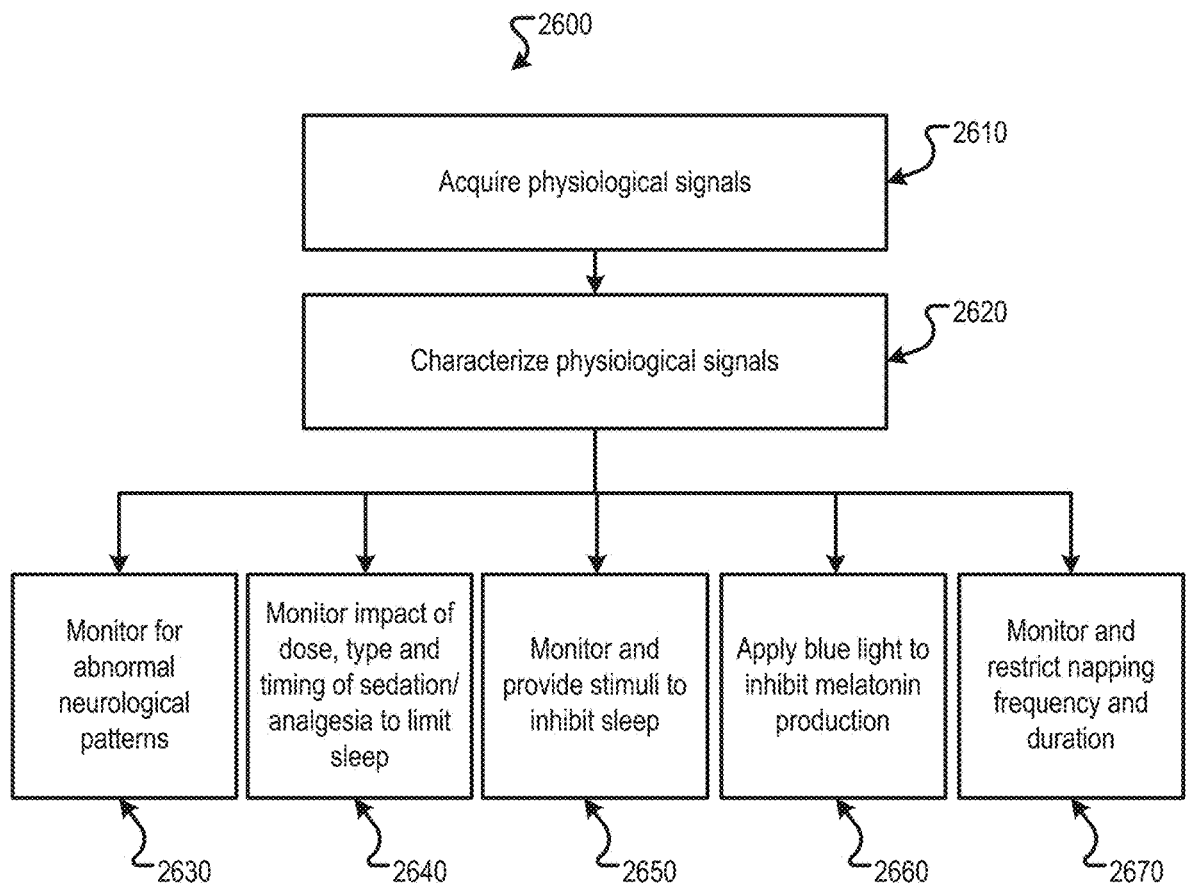
FIGS. 26 and 27 are flow charts of example methods for monitoring a patient's circadian rhythm to improve the quality of sleep, in accordance with embodiments herein.
Figure 27:
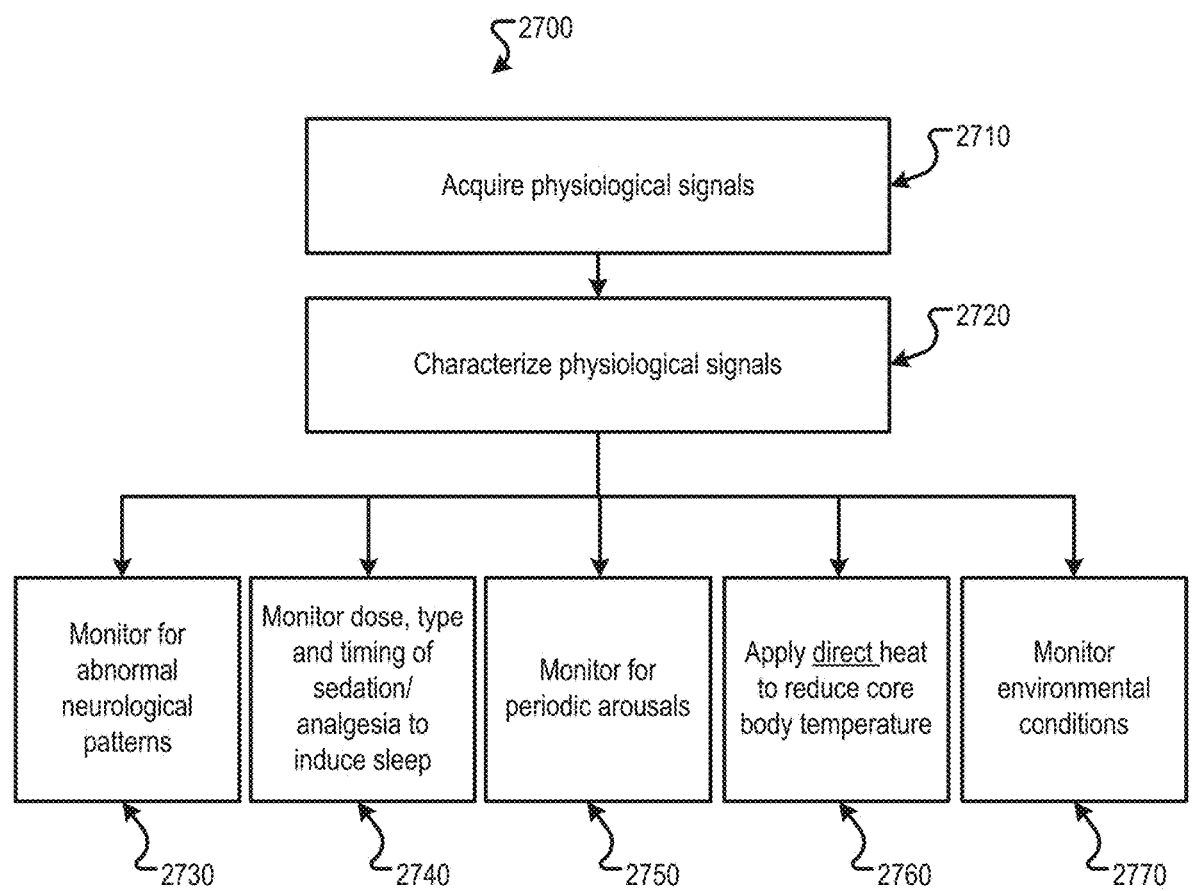

FIGS. 26 and 27 provide flow charts of example processes 2600 and 2700, respectively, for monitoring a patient's circadian rhythm to improve the quality of sleep. For example, the process 2600 and/or 2700, either alone or in combination, may be implemented using, for example, the DAU 110 and/or the integrated system of FIG. 5 in a hospital, ICU, or other environment that may impact a patient's ability to sleep to reduce the risk of delirium and speeds recovery by hospitalized patients by monitoring sleep/wake patterns so that natural circadian rhythms can be maintained. In some embodiments, either of process 2600 and/or 2700 may be implemented as part of step 825 of FIG. 8 or as a separate process.

In several embodiments, the systems described herein may be capable of monitoring a current sleep state, previous sleep states, and arousals from sleep, and implement the any one or more of the features described throughout this disclosure to, for example, discourage sleep during the daytime, restrict daytime naps to the hours of 2 and 4 PM, and/or encourage consolidated sleep during the nighttime, or a combination thereof.

For example, process 2600 may be implemented to discourage and/or restrict sleep during the day. Process 2600 beings by acquiring (step 2610) and characterizing (step 2620) physiological signals of a patient. In some embodiments, steps 2610 and step 2620 may be similar to steps 805 and 810 of FIG. 8, respectively. The characterized signals of step 2620 are then monitored for abnormal neurological patterns (step 2630) and treat accordingly. For example, abnormal neurological patterns may be any one or more of the abnormal features identified in either FIG. 13 and/or FIG. 15. At step 2640, the impact of the medication on sleep stages may be monitored. For example, the DAU 110 may monitor sleep stages as described above and correlated with the medication (e.g., sedative and/or analgesia) type, dosage, and/or timing of administrating such to derive an impact thereof. In some embodiments, to reduce the likelihood of daytime napping in a hospitalized environment the, dosage of sedative can be decreased. Alternatively or additionally, at step 2650, the environmental stimuli that inhibit or otherwise affect sleep may be monitored. For example, environmental conditions can be modified to discourage sleep during daytime hours, for example, by allowing environmental noise, timing of visitations and/or human interactions. In some embodiments, light exposure may be modified (e.g., step 2660) to affect the patient's sleep. For example, exposure to certain wavelengths of light (e.g., blue light) may be used to inhibit melatonin production in the patient. Furthermore, in some embodiments, the frequency and/or duration of napping may be monitored and modified to control daytime napping (step 2670).

During nocturnal hours, process 2700 may be utilized to improve the quality and quantity of sleep. For example, when it is nocturnal hours, process 2700 begins by acquired (step 2710) and characterized (step 2720) physiological signals of a patient. In some embodiments, steps 2710 and step 2720 may be similar to steps 805 and 810 of FIG. 8, respectively. The characterized signals of step 2720 are then monitored for abnormal neurological patterns (step 2730) and treat accordingly. For example, abnormal neurological patterns may be any one or more of the abnormal features identified in either FIG. 13 and/or FIG. 15. At step 2740, the impact of the medication on sleep stages may be monitored. For example, the DAU 110 may monitor sleep stages, as described above, and correlated with the medication (e.g., sedative and/or analgesia) type, dosage, and/or timing of administrating such to derive an impact thereof. In some embodiments, to increase the likelihood of sleeping in a hospitalized environment the, dosage of sedative can be increased. At step 2750, periodic arousals of the patient may be monitored. For example, periodic patterns identified in FIG. 13 may be indicative of arousals. In some embodiments, combining modification of sleeping position with and/or in response to certain arousals may be used to intervene and otherwise reduce the severity period waking (e.g., reducing the severity of SDB in patients sleeping in supine position. At step 2760, temperature changes may be applied to the patient (e.g., directly and/or indirectly) to control core body temperature and improve comfortability. For example, the application of heat or cooling temperatures to the frontal regions of the patients face may affect the patient's core temperature to induce sleep. At step 2770, the environmental stimuli that induce or otherwise affect sleep may be monitored. For example, environmental conditions can be modified to encourage sleep during nocturnal hours, for example, by restricting environmental noise, human interactions, and exposure to light to provide environmental conditions more conducive to sleep.

While processes 2600 and 2700 are described as a series of steps

In various embodiments of the systems and methods described herewith, the detected physiological signals may be used to assess an amount of REM sleep or detect early onset of REM. These assessments may be used to help with diagnosis of various ailments that may affect sleep. For example, assessment of the amount of REM sleep of a patient may be used to diagnose depression while detecting early onset of REM may be useful to diagnose narcolepsy. In some embodiments, physiological signals detected, for example, by the DAU 110 can also be used to minimize long term traumatic stress syndrome (PTSD) symptoms. For example, suppression of REM sleep immediately following a traumatic event may limit the capability of the brain to encode the traumatic event into memory and thus impacts (e.g., reduce and/or minimize) the severity of the symptom(s). As described above, it may advantageous to steer such patient's sleep stages out of or away from REM and into NREM without waking the patients. In some embodiments, steering a patient's sleep may be implemented using the systems and method described herein in conjunction with sleep guidance systems described above in connection to FIG. 5 above.

As an example, a patient may be admitted to the hospital following a traumatic event (e.g., a car accident or the like), and identified by caregivers as at risk for PTSD. The DAU 110 can be applied to the patient during their first night following the event, in either an in-patient or out-patient setting, to steer or otherwise control the patient's sleep, for example, by shifting the patient out of REM sleep and into NREM sleep without causing the patient to wake up. By suppressing and/or avoiding REM, the effects of PTSD may be minimized, reduced, avoided, and/or treated without affecting the patient's sleep and, which could otherwise cause sleep deprivation.

In some embodiments, a patient identified as at risk for PTSD may be admitted for overnight monitoring by hospital staff, and the DAU 110 may be used to monitor the sleep stages of the patient. Upon detecting REM sleep or detecting a transition into REM sleep as described herein, a caregiver or an automated system (e.g., the sleep guidance system 530) may intervene as described above to lead the patient away from REM and into NREM. In some embodiments, one or more stimuli may be applied to the patient by, for example, the sleep guidance system 530 to induce the desired the transition. For example, the stimuli may include, but not limited to light, sound, smell, vibration, heat or cold, moisture, electric shock, and/or other stimuli that can be sensed by a sleeper. For example, in some embodiments, delivery of vibrotactile and/or blue light may suppress REM sleep.

Figure 28:
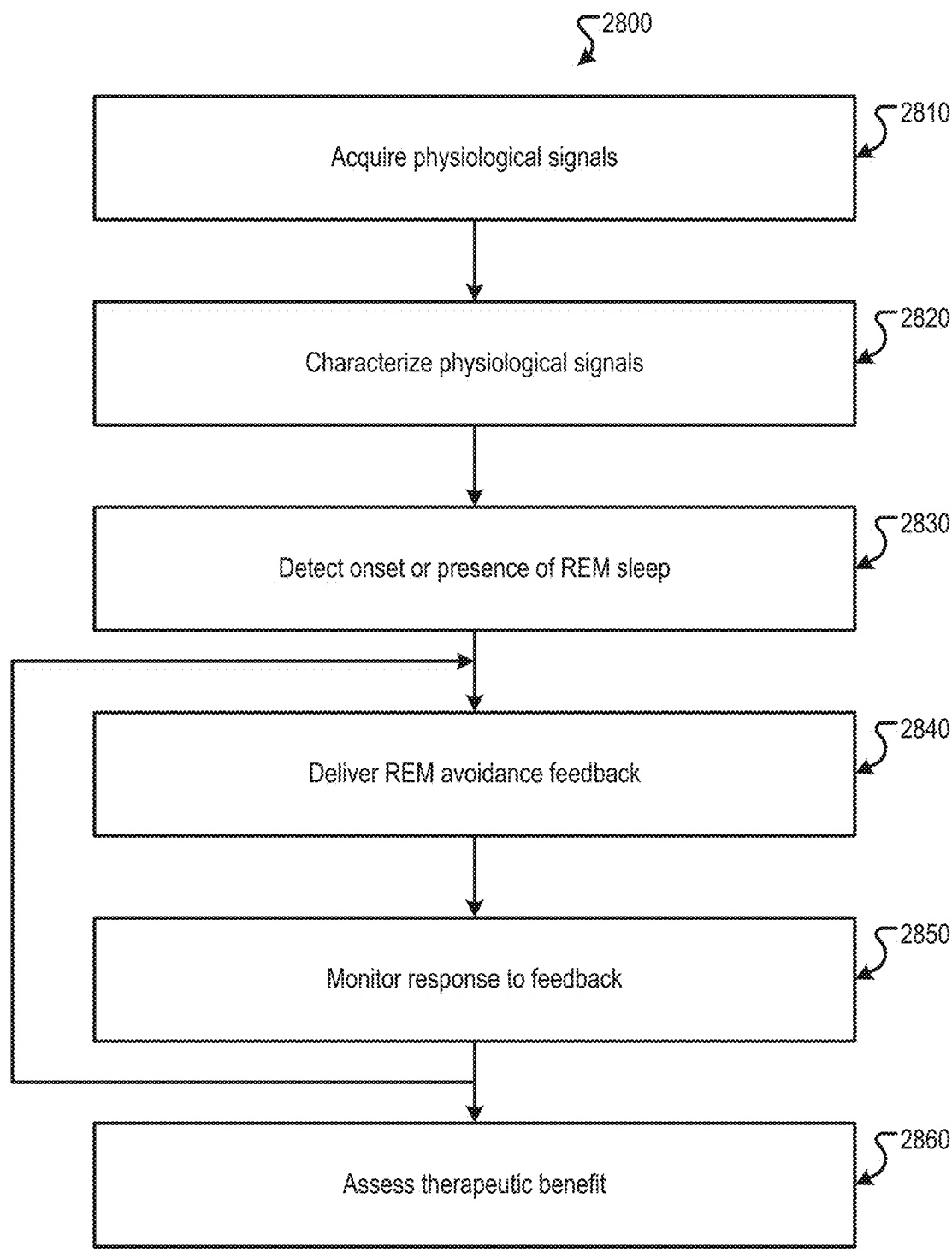
FIG. 28 is a flow chart of an example method for reducing the likelihood of developing symptoms of post-traumatic stress syndrome, in accordance with embodiments herein.

FIG. 28 provides a flow chart of an example process 2800 for reducing the likelihood of developing symptoms of PTSD. For example, the process 2800 may be implemented using, for example, the DAU 110 and/or the integrated system of FIG. 5 in a hospital, ICU, in-patient setting, out-patient setting, or other environment that may impact a patient's ability to sleep to reduce the risk of sleep deprivation and reduce onset of PTSD.

In some embodiments, the process 2800 may be implemented following identification of a patient at-risk of PTSD. For example, process 2800 may be implemented using the integrated system of FIG. 5 once a patient has been admitted for overnight monitoring based, in part, on experiencing a traumatic event.

Process 2800 beings by acquiring (step 2810) and characterizing (step 2820) physiological signals of a patient. In some embodiments, steps 2810 and step 2820 may be similar to steps 805 and 810 of FIG. 8, respectively. The characterized signals of step 2820 are then monitored to detect the onset and/or presence of REM sleep stag (step 2830). For example, the DAU 110 may acquire physiological signals of the patient and, either alone or in combination with other components of integrated system of FIG. 5, may characterize the signals to detect and monitor the sleep stages of the patient. The monitored sleep stages may be based in part on standard sleep staging rules and/or modified sleep staging rules (e.g., as described above in connection to FIG. 12). The process 2800 monitors the sleep stages to detect the onset of and/or presence of REM sleep.

If either of onset of REM and/or presence of REM sleep is detected in step 2830, the process 2800 generates one or more feedback signals to avoid REM and delivers these signals to patient (step 2840). For example, the integrated system of FIG. 5 may determine feedback signals in the form of stimuli as described above, and may generate the stimuli (e.g., light, sound, heat, smell, etc.) to steer the patient away from and avoid REM sleep. Generating the stimuli may include deliver of the stimuli via the sleep guidance system as described above in connection to FIG. 5 above.

At step 2850, the process 2800 monitors the patient's response to the delivered feedback. For example, at step 2850, the patient's physiological signals may be monitored to ensure that the patient's sleep stage has been successfully steered away from and/or out of REM sleep. In some embodiments, the monitoring of step 2850 may be done using the DAU 110 and/or integrated system of FIG. 5. In some embodiments, monitoring the response to the delivered feedback may be similar to monitoring the patient for onset and/or presence of REM sleep (e.g., step 2830). If the patient begins to enter REM and/or is currently in REM during the monitoring step 2850, the process 2800 returns to step 2840 to steer the patient out of and/or away from REM. Thus, the patient is continuously monitored for sleep stages and steered accordingly.

At step 2860, the therapeutic benefit may be assessed. For example, the DAU 110 may communicate physiological signals to one or more computer systems that may be used to assess the therapeutic benefit of process 2800. In some embodiments, a medical care giver may be capable of reviewing physiological signal data via, for example, a graphic user interface such as the interface described below in FIGS. 29-31. In some embodiments, step 2860 is performed once the patient is successfully steered away from and/or out of REM sleep. In some embodiments, alone or in combination, step 2860 may be performed in conjunction with either of steps 2840 and/or 2850 as well as during the feedback loop following step 2850.

Figure 29:
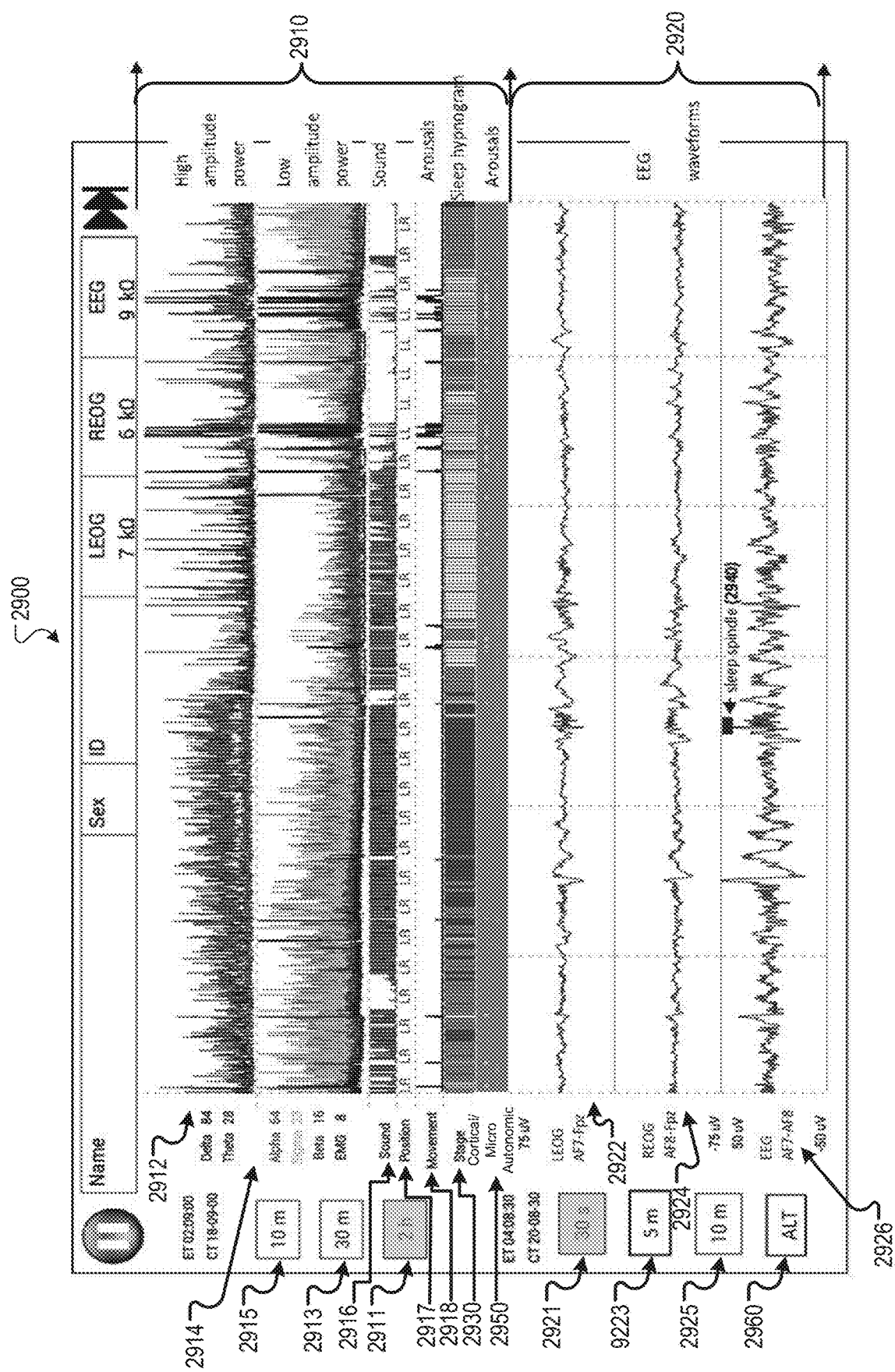
FIGS. 29-31 illustrate embodiments of a graphical user interface for displaying physiological signal patterns, in accordance with embodiments herein.
Figure 30:
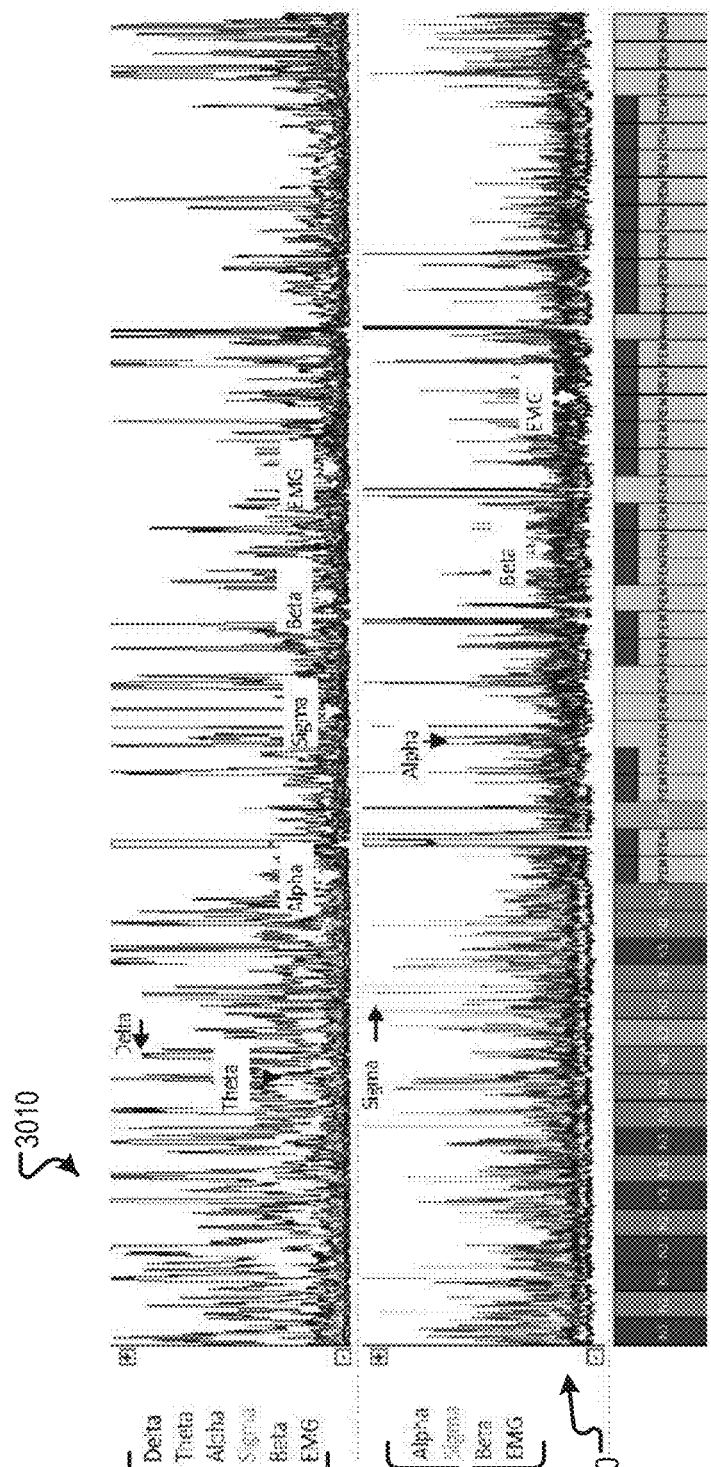
Figure 31:
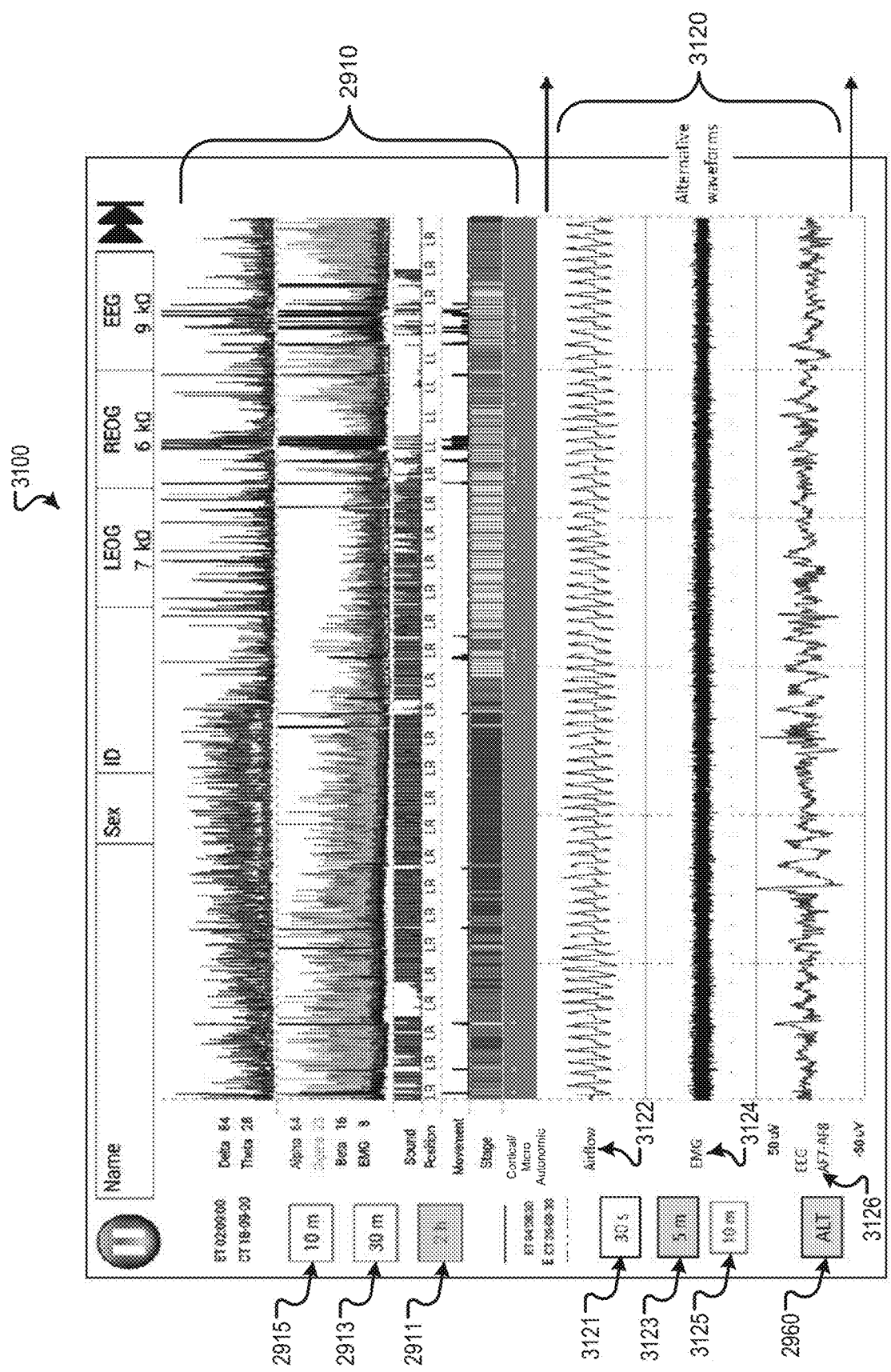

FIGS. 29-31 illustrate embodiments of graphical user interfaces (GUI) for simplifying the presentation of and improving readability of physiological signals for use of monitoring such signal for abnormal signal patterns and/or conditions. The embodiments of the GUIs described herein may be used by users (e.g., caregivers, medical personnel, experts, etc.) to view physiological signals of a patient for use in monitoring, interacting with, diagnosing, and otherwise performing the processes described in, for example, FIGS. 8-28 and throughout this application. The GUI may be generated by one or more software modules of the DAU 110, computer systems 390, 550, and/or mobile device 550 of the integrated system of FIG. 5, and may be displayed on a physical display (e.g., a touch panel display) of the computer systems 390, 550 and/or mobile device 550. The graphical user interface may comprise one or more displayable screens, such as the screens illustrated in FIGS. 29-31, as well as other screens described and/or implied herein. While many of the screens of the GUI will be individually described, the described screens simply represent non-limiting, exemplary embodiments of the GUI. The GUI may be implemented in a different manner, with fewer or more of the described screens and/or a different arrangement, ordering, and/or combination of the described screens.

The GUI may be different for different systems, depending on one or more characteristics of the particular system used to view the GUI (e.g., device type, display size, availability of particular input devices, processor speed, network speed, etc.). For example, the GUI displayed on a mobile device 550 and/or tablet computer may be simpler and/or more compact than the GUI displayed on a computer system 560, in order to accommodate the generally smaller display sizes on mobile devices. As another example, the GUI displayed on a computer system having a touch panel display, configured to accept touch operations from a user's finger and/or stylus (e.g., touches/presses, long touches/ presses, swipes, flicks, pinch-in operations, pinch-out operations, etc.), may be different than the GUI displayed on a system that does not have a touch panel display. Alternatively, the GUI may be identical across all systems and/or device displays.

While user operations on the GUI will primarily be described herein using touch operations, it should be understood that analogous non-touch operations may be used in place of any of the described touch operations. For example, a short touch or tap may be replaced by a click-and-release (e.g., by a mouse or other pointing device), a long touch may be replaced by a click-and-hold or a hover, a swipe may be replaced by a click-and-drag, a flick may be replaced by a click-and-drag-and-release, and so on and so forth.

In addition, any of the user operations described herein, including the selection of icons or buttons or menu options, navigation (e.g., scrolling, zooming in and/or out, transitioning between abnormal signal identifiers, etc.), and/or the like, may be performed via voice input. For example, the computer system may receive a speech input via a microphone, convert the speech input to a text representation via speech-to-text processes, and provide the text representation to the GUI as an operation input. For example, the computer system may match the text representation to a command and execute the matched command.

It should also be understood that many, if not all, of the screens, regions, and/or panes described herein may be scrollable (e.g., by swiping up or down). Thus, if the time scale of a given epoch and/or sleeping event is too long to be viewable in a single region and/or pane, only a portion of the epoch and/or sleeping event may be initially displayed, and the user may scroll through the signal data to view previously collected data and scroll back to return to currently acquired data.

FIG. 29 illustrates an embodiment of a display screen 2900 of EEG activity displayed using the GUI described herein. The information presented in the GUI may be representative of the physiological signals of a patient and may be useful in monitoring normal and abnormal sleep and EEG activity as described throughout this disclosure. The GUI may segment the display screen into a plurality of regions. As illustrated in the example shown in FIG. 29, the display screen is segmented into an upper half region 2910 and a lower half region 2920. The upper half region 2910 may include power spectra characteristics displayed on a first time scale selected to optimize the visual recognition of normal and abnormal signal patterns. Similarly, the lower half region 2920 may include other channels displayed on a second time scale selected to optimize the recognition of normal and abnormal signal patterns in those channels. In some embodiments, the first and second time scales may different as described below.

Additionally, in some embodiments, the upper half region 2910 and/or lower half region 2920 may be further segmented into a plurality of panes 2912, 2914, 2916, 2917, and 2918 in the upper half region 2910 and a plurality of pans 2922, 2924, and 2926 in the lower half region 2920. For example, FIG. 29 illustrates the delta and theta power signals (e.g., high amplitude power signals) are presented in pane 2912 and the alpha, sigma, beta and gamma/EMG signals (e.g., lower amplitude power signals) are presented in pane 2914. The delta, theta, alpha, sigma, beta and EMG power can be displayed in a plurality of time scales via selectable icons 2911, 2913, and 2915 in conjunction with recorded sound (e.g., pane 2916), position (e.g., pane 2917), movement (e.g., pane 2918) and the classified sleep stage in pane 2930. For example, the display screen 2900 includes an icon 2913 for displaying the upper half region at a 10 min time scale, an icon 2913 for displaying on a 30 min time scale, and an icon 2915 for displaying on a 2 hour time scale. In some embodiments, the signal data displayed in each of the panes may be changed and otherwise modified to fit the particular application and/or screen sizes used to view the data.

The lower half region 2920 may include the LEOG, REOG and EEG channels displayed in one or more panes. For example, as shown in FIG. 29, the LEOG is displayed in the pane 2922, REOG in pane 2924, and EEG in pane 2926. Similar to upper half region 2910, the lower half region may display each pan in the 30 sec epoch (e.g., via selectable icon 2921), 5 min (e.g., via selectable icon 2923) or 10 min (e.g., via selectable icon 2925) time scales.

The upper and lower half regions 2910 and 2920 may be independent with respect to function (e.g., time scale and visual inspection). In some embodiments (not shown), the plurality of panes within each region may be independent with respect to the other panes (e.g., displayed at different amplitude ranges and/or time scales). The GUI may be configured to include a plurality of identifiers of patterns generated based the physiological signal as described throughout this disclosure used to stage sleep (e.g., identifiers 2930), including sleep spindles (e.g., identifier 2940) and/or cortical arousals (e.g., identifier 2950). Thus, the user of the system may be able to view the various physiological signals at different time scales so to more easily identify normal and abnormal signal patterns. Furthermore, the GUI provides an ease of switching between selectable time scales for ease of comparison between the various signals and analysis of previous physiological signals so to identify prior or worsening patterns.

While a specific example is illustrated in FIG. 29, it will be appreciated that other arrangement are possible. For example, the number of regions may be increased as desired to ease the display and identification of abnormal patterns. Furthermore, the number of panes within each region may be increased and/or decreased as desired. For example, each power signal may be displayed in its own pane for separate analysis and comparison. In some embodiments, the number of regions and/or panes may be based in part on the device on displaying the GUI. For example, a mobile device may have a smaller screen than a computer monitor, thus fewer panes may be displayed as compared with the larger screen. Furthermore, the time scales of icons 2911-2925 are for illustrative purposes only, and any desired time scale may be utilized (e.g., 8 hour, 12 hour, 10 s, etc.) as desired for the specific application.

FIGS. 30A and 30B illustrate example display screens 3010 and 3020 for presenting power spectral densities on a first time scale (e.g., 30 minutes in this example). FIG. 30A illustrates all power values (e.g., delta, theta, alpha, sigma, beta, and EMG) presented in one display screen 3010, while FIG. 30B illustrates a subset of power bands (alpha, sigma, beta, and EMG) having similarly scaled amplitude magnitudes in a different display screen 3020. As illustrated in FIG. 30B, displaying the subset of power bands having similar amplitude magnitudes permits improved detection of sleep stage transitions. Whereas, when all power bands are combined and presented in a single screen (e.g., FIG. 30A) the magnitude of power in the delta and theta frequency ranges is so much greater than the alpha, sigma, beta and EMG power bands that may be difficult to detect differences in the relative power characteristics. When the relationship between the alpha, sigma, beta and EMG is undetectable, it reduces the benefit of displaying the physiological signals to help distinguish between non-REM from REM sleep. When the delta and theta are presented in one pane and the remaining power frequencies are presented in a second pane (e.g., FIG. 30B), it my easier to recognize the relative changes in sigma and beta power during transitions between non-REM and REM sleep and EMG power during sleep and wake. In one embodiment, FIG. 30B may be similar to pane 2914 of FIG. 29.

FIGS. 30A and 30B may be illustrative of a non-limiting advantage of the GUI as described herein. For example, it may be advantages that power bands with low amplitude values be displayed in a separate display screen (FIG. 30A) or separate pane (FIG. 29) than relatively higher amplitude values. In one embodiment, the signals may be separated and scaled into separate panes (e.g., FIG. 29), with the values in each pane automatically scaled to accommodate the values of the individual being monitored. In another embodiment, alone or in combination, a user may be able to selectably switch between the presentations of the two sets of signals. In various embodiments the power spectra signals are displayed in combinations with alternative means for scaling the signals to enable visual detection of normal and abnormal patterns.

To further assist with monitoring, the magnitude of the sound and movement, head position, patterns of sleep stages, and cortical and sympathetic arousals may be presented on a selectable time scale (e.g., pane 2916 of FIG. 29). For example, three frontopolar EEG signals are illustratively displayed with the signals from AF7-Fpz and AF8-Fpz, which contain the left and right ocular activity are default scaled to +75 µV to accommodate the typical range of the ocular signal amplitude. The signal obtained from AF7-AF8, labeled EEG, is presented with a default of +50 µV. The values obtained from routine acquisition of the skin-sensor impedances from each site are presented to permit the user to be sure the device is properly affixed and collecting high quality signals. The automated detection of sleep spindles 2940 may be presented as one or more stripes above the detected region of the EEG signal. Cortical arousals or other EEG feature characteristics (e.g., ocular activity, detected sharp edges in the waveform, etc.) can be identified in accordance with the embodiments described herein and marked in the display.

Mobile devices, such as tablets and mobile telephones, may be limited in screen size and many physiological signals may need to be scaled sufficiently to allow visual interpretation. To accommodate both requirements, multiple screen presentations can be used to present the standard signal information as well as alternative signal information (e.g., airflow or EMG signals). For example, the airflow signal may permit a user to identify when an extubated patient has undiagnosed OSA. An EMG signal obtained from sensors affixed near the submental muscle may assist in the differentiation of REM from non-REM, or REM without atonia. An EMG signal obtained with sensors affixed near the diaphragm muscle would enable a critical care worker identify acute respiratory distress syndrome or identify ventilator asynchrony.

Accordingly, in some embodiments, an ALT icon 2960 may be provided in the GUI for selectable switching presentation configurations. A first display screen may be set as a default configuration and an alternative display screen may be set as an ALT configuration. Each configuration may be used to display one or more of the physiological signals as described herein. In an example embodiment, the first display screen may be display screen 2900 and the user may interact with the ALT icon 2960 to switch to a second display screen. An example second display screen is illustrated in FIG. 31, which includes upper half region 2910 and alternative lower half region 3020. The alternative lower half region 3020 includes pane 3022 illustrating an airflow signal, pane 3024 illustrating an EMG signal, and pane 3026 illustrating an EMG signal. Alternative lower half region 3020 may be similar to lower half region 2920, but displaying a different configuration of signals. The signals displayed in each region 2910, 2920, and 3020 may be different than those shown in the illustrative examples.

Thus, the ALT icon 2960 may enable presentation of a configurable alternative segment of signals. In one configuration, the ALT icon 2960 may not appear in the upper half region 2910 because there is may not be an alternative configuration defined. For the lower half region 2920, the ALT icon 2960 may be used to select presentation of the airflow signal in pane 3022, acquired by the DAU 110 configured with a nasal pressure transducer 280 and nasal cannula 160, in patients who are not intubated and mechanically ventilated. The pane 3024 may be selected for presentation of an EMG signal. In one embodiment, the EMG signal is acquired from the submentalis muscles for use in visually confirming the differentiation of REM from non-REM sleep. One skilled in the art will recognize that different combinations of signals can be presented and/or adjusted to different time scales. The device settings to configure the DAU 110 can be made locally on a tablet sized computer used to present the signals, or when interfaced to a desktop computer or a web-based portal.

In one embodiment, time scales can be applied individually to the presentation of the physiological signal for the upper and lower half regions. For the signals in the upper half region 2910, the characteristics which differentiate normal from abnormal patterns may be optimally viewed in long time windows, while the signals and signal characteristics useful in confirming abnormal frontopolar EEG may be presented on a shorter duration time scale (e.g., lower half regions 2920 and/or 3020). In an alternative embodiment, alone or in combination, the ratios of the power values sensitive to the differentiation of normal and abnormal neurophysiological patterns are presented. Alternative embodiments alone or in combination, include the use of machine learning techniques to incorporate other physiological patterns, e.g., sound, heart rate, movement and/or position, to assist in the automated and/or visual differentiation of normal and abnormal patterns.

A number of other features can be added to the GUI to assist in the detection, monitoring or inspection of abnormal event periods. Because ASWA is associated with sepsis, delirium and mortality, the percentage of recording time detected with ASWA can be tallied, summarized, and presented in the GUI. Other feature characteristics can also be summarized to assist in the detection of abnormal conditions, e.g., percentage of rejected signal time by channel, total and percentage of sleep time, sleep spindle and cortical arousal event duration and/or events per hour, etc.

A number of touch screen features may be used to scale the regions and/or panes. The GUI may be configured to permit a user to interaction with any one or more displayed panes independent from or without impacting other panes. Thus, signals displayed in any one or more pane may be individually reviewed. For example, a user may interact with a pane, for example, displaying the sleep stage information by swiping the pane to the left to cause the illustrated information shift or otherwise transition to a selected point in the record of sleep stages (e.g., to a past or previous sleep stage relative to the current time). Similarly, a user may interact with a given pane to zoom in or zoom out using, for example, a pinching or reverse pinching motion on a given pane. Thus, any of these signals can be presented on a shorter or longer duration time windows, or in different combinations of signal panes to enable visual monitoring and detection of normal and abnormal patterns.

In another embodiment, alone or in combination, another icon may be provided to enable the presentation on the screen to immediately transition back in time to a period with ASWA or other auto-detected abnormal period for more careful inspection. The icon(s) may also be used to transition back to periods based on other signal patterns, e.g., excessively loud sounds, artifact, etc. Each time the icon is interacted with, the presentation may transition back further in time in the record to the next or earlier detected period. This may improve usability by providing an alternative to having the user scroll sequentially back through the record during visual inspection. In one embodiment, thresholds, as described above for detecting the various abnormal signal patterns, applied to the signal patterns used to detect the transition points may be automatically applied by the software. In an alternative embodiment, the thresholds can be manually set or selected using the same approach described above for setting the device settings for the DAU 110.

The capability of the DAU 110 to acquire and the GUI to present different combinations of physiological signals may advantageously provide caregivers a way to detect a source of an underlying problem. For example, in one embodiment a pitot tube may be used to extract an airflow signal from a mechanical ventilator for input into the nasal pressure transducer and surface electrodes placed over the diaphragm can be used to acquire an EMG signal (e.g., shown in FIG. 31). Asynchrony between the airflow signal and voluntary contraction observed in the EMG may indicate ventilator timing issues. Synchronous patterns, on the other hand, may indicate central sleep apnea. Steady sound can indicate more subtle breathing issues (e.g., discomfort from the endotracheal tube). In an alternative embodiment, the DAU 110 can be configured to acquire respiratory effort signals whereby the differences in the signal patterns between the torso and abdomen belts are used to identify central sleep apnea. In each of these examples, the signal patterns can alert the caregiver of a previously undetectable problem that can compromise the comfort or recovery of the patient.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Furthermore, while each of the methods and processes described herein are illustrated as a specific sequence of steps, in alternative embodiments, any of the processes may be implemented with more, fewer, or a different arrangement and/or ordering of steps. Various modifications to these processes and methods will be readily apparent to those skilled in the art, and the general principles described herein can be applied to other embodiments described herein without departing from the spirit or scope of the invention.

What is claimed is:

1. A method for managing sleep quality of a patient in a hospital environment, the method comprising:
    collecting physiological signal data of the patient using a data acquisition unit electrically coupled to at least one sensor affixed to the patient that generates the physiologic signal data;
    using one or more hardware processors executing instructions stored in a storage device:
        filtering the physiological signal data into a plurality of frequency bands corresponding to a plurality of power spectra waveforms;
        extracting features in the plurality of power spectra waveforms to identify a plurality of sleep stages of the patient over a time period;
        generating a graphical user interface comprising a plurality of panes, the plurality of panes comprising,
            a first pane displaying:
                at least one physiological signal needed to stage sleep corresponding to a first portion of the time period on a first time scale, and
            a second pane displaying:
                a second portion of the time period on a second time scale that is longer than the first time scale, the second portion of the time period comprising at least a portion of the time period previous to the first portion of the time period,
                a subset of sleep stages corresponding to the second portion of the time period, and
                at least one power spectra waveform of the plurality of power spectra waveforms corresponding to the second portion of the time period, and
        characterizing an etiology of sleep quality of the patient based on a comparison of the at least one physiological signal on the first time scale against the at least one power spectra waveform on the second time scale, wherein the sleep quality of the patient is managed based on the characterized etiology of sleep.

2. The method of claim 1, further comprising detecting one or more abnormal conditions indicative of a disruption to sleep quality of the patient based on a comparison of the at least one physiological signal on the first time scale against the at least one power spectra waveform on the second time scale.

3. The method of claim 2, wherein the one or more abnormal conditions comprises characteristics within one or more of the plurality of power spectra waveforms indicative of at least one of abnormal slow wave activity, disordered breathing, frontal intermittent rhythmic delta activity, abnormal burst suppressions, and non-convulsive seizure activity.

4. The method of claim 2, wherein the patient is associated with a therapeutic treatment, the method further comprises performing an action by a sleep guidance system based on the detected one or more abnormal conditions to modify the therapeutic treatment.

5. The method of claim 1, wherein the plurality of power spectra waveforms comprises at least one of rhythmic activity and transients.

6. The method of claim 1, wherein the plurality of power spectra waveforms comprises at least one or more of an alpha power spectra waveform, a sigma power spectra waveform, a beta power spectra waveform, a delta power spectra waveform, a theta power spectra waveform, an electromyographic (EMG) power spectra waveform, a electroencephalographic (EEG) power spectra waveform, at least one electroocular (EOG) power spectra waveform, acoustic signal data, and movement signal data.

7. The method of claim 1, further comprising:
    identifying the plurality of sleep stages of the patient over the time period;
    determining at least one sleep stage of the plurality of sleep stages does not match an expected sleep stage of the patient; and
    in response to said determination, comparing the at least one physiological signal on the first time scale against the at least one power spectra waveform on the second time scale to identify an abnormal signal pattern indicative of a disruption to sleep quality of the patient.

8. The method of claim 7, wherein the sleep stage of the plurality of sleep stages does not match an expected sleep stage due, in part, to at least one of an acute status of the patient, medication administered to the patient, and a therapeutic treatment for the patient.

9. The method of claim 1, wherein the collected physiological signal data is communicated by the data acquisition unit to an external computer system comprising the one or more hardware processors, the method further generating the graphical user interface on a display communicatively coupled to the external computer system, wherein the plurality of panes are provided for separately interacting with the physiological signal data.

10. The method of claim 9, wherein the external computer system is configured to receive physiological signal data of a plurality of patients from a plurality of data acquisition units electrically coupled to a plurality of sensors affixed to the plurality of patients.

11. The method of claim 9, wherein the external computer system is associated with a specialist.

12. The method of claim 1, further comprising, using a sleep guidance system:
    determining a current sleep state of the patient based on the collected physiological signal data;
    determining a desired sleep state for the patient based on one or more sleep staging rules, the current sleep state, and an acute status of the patient, wherein the one or more sleep staging rules are configured to determine a desired sleep state that improves recovery time from the acute status; and
    executing an action to guide the patient toward the desired sleep state if desired sleep state is different from the current sleep state.

13. The method of claim 1, wherein the hospital environment is one of at least an intensive care unit and an emergency room.

14. The method of claim 1, further comprises:
    streaming the collected physiological signal data to a computer system; and
    rendering the collected physiological signal data on a display using the graphical user interface, the physiological signal data presented in the plurality of panes.

15. The method of claim 14, wherein the first and second time scales are selected to facilitate comparison of at least the first power spectra waveform with the second power spectra waveform.

16. The method of claim 1, wherein the at least one sensor comprises a plurality of sensors less than a full 10-20 montage of sensors.

17. A system for managing sleep quality of a patient, the system comprising:
    a data acquisition unit electrically coupled to at least one sensor configured to affix to the patient, wherein the data acquisition unit collects physiological signal data of the patient generated by the at least one sensor;

at least one hardware processor; and a storage device coupled to the at least one hardware processor and the data acquisition unit, the storage device storing instructions that, when executed by the at least one hardware processor, are operable to:

filter the physiological signal data into a plurality of frequency bands corresponding to a plurality of power spectra waveforms;

extract features in the plurality of power spectra waveforms to identify a plurality of sleep stages of the patient over a time period, generate a graphical user interface comprising a plurality of panes, the plurality of panes comprising:

a first pane displaying:
at least one physiological signal needed to stage sleep corresponding to a first portion of the time period on a first time scale, and a second pane displaying:
a second portion of the time period on a second time scale that is longer than the first time scale, the second portion of the time period comprising at least a portion of the time period previous to the first portion of the time period,
a subset of sleep stages corresponding to the second portion of the time period, and at least one power spectra waveform of the plurality of power spectra waveforms corresponding to the second portion of the time period, and characterize an etiology of sleep quality of the patient based on a comparison of the at least one physiological signal on the first time scale against the at least one power spectra waveform on the second time scale, wherein the sleep quality of the patient is managed based on the characterized etiology of sleep.

18. The system of claim 17, wherein the instructions are further operable to detect one or more abnormal conditions indicative of a disruption to sleep quality of the patient based on a comparison of the at least one physiological signal on the first time scale against the at least one power spectra waveform on the second time scale.

19. The system of claim 17, further comprising an external computer system communicatively coupled to the data acquisition unit and comprising a display, wherein the collected physiological signal data is communicated to the external computer system, and the instructions further operable to generate a graphical user interface on the display, the graphical user interface comprising a plurality of panes for separately interacting with the physiological signal data.

20. The system of claim 19, further comprising a cloud server communicatively coupled to the data acquisition unit for receiving the physiological signal data, the cloud server accessible by one or more remote computer systems for retrieving at least a portion of the physiological signal data.

* * * * *